United States Patent
Kadowaki et al.

(10) Patent No.: US 8,252,584 B2
(45) Date of Patent: Aug. 28, 2012

(54) ADIPONECTIN RECEPTOR AND GENE ENCODING THE SAME

(75) Inventors: Takashi Kadowaki, Kanagawa (JP); Toshimasa Yamauchi, Tokyo (JP); Ryozo Nagai, Tokyo (JP); Junji Kamon, Saitama (JP)

(73) Assignees: Toudai TLO, Ltd., Tokyo (JP); Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 13/153,017

(22) Filed: Jun. 3, 2011

(65) Prior Publication Data
US 2012/0027760 A1 Feb. 2, 2012

Related U.S. Application Data

(60) Division of application No. 12/322,111, filed on Jan. 29, 2009, now Pat. No. 7,977,459, which is a division of application No. 11/598,474, filed on Nov. 13, 2006, now Pat. No. 7,501,490, which is a division of application No. 10/799,943, filed on Mar. 11, 2004, now abandoned, which is a continuation of application No. PCT/JP03/07515, filed on Jun. 12, 2003.

(30) Foreign Application Priority Data

Dec. 29, 2002 (JP) ................................. 2002-383738

(51) Int. Cl.
C12N 5/07 (2010.01)
C12N 5/16 (2006.01)
C07K 16/00 (2006.01)
C12P 21/08 (2006.01)

(52) U.S. Cl. .............. 435/334; 530/388.22; 530/388.15; 530/388.1; 530/387.9; 530/389.1; 435/326; 435/331; 435/344.1

(58) Field of Classification Search .......................... None
See application file for complete search history.

(56) References Cited

U.S. PATENT DOCUMENTS

| 7,435,808 B2 * | 10/2008 | Wu et al. ...................... 536/23.5 |
| 2002/0182671 A1 | 12/2002 | Lal et al. |
| 2004/0067490 A1 | 4/2004 | Zhong et al. |

FOREIGN PATENT DOCUMENTS

| EP | 1074617 A2 | 2/2001 |
| JP | 2002-191363 | 7/2002 |
| JP | 2002/383738 | 12/2002 |
| WO | 01/12662 A2 | 2/2001 |
| WO | 01/57190 A2 | 8/2001 |
| WO | 01/90304 A2 | 11/2001 |
| WO | 2004-061108 A1 | 7/2004 |
| WO | 2004/087874 A2 | 10/2004 |
| WO | 2005/001061 A2 | 1/2005 |

OTHER PUBLICATIONS

Arita, Yukio et al., "Adipocyte-Derived Plasma Protein Adiponectin Acts as a Platelet-Derived Growth Factor-BB-Binding Protein and Regulates Growth Factor-Induced Common Postreceptor Signal in Vascular Smooth Muscle Cell," Circulation, vol. 105:2893-2898 (2002).

Barger, P.M., et al. "p38 mitogen-activated protein kinase activates peroxisome proliferator-activated receptor alpha: a potential role in the cardiac metabolic stress response." J Biol Chem. Nov. 30, 2001; 276(48):44495-501.

Berg, A.H., et al. "The adipocyte-secreted protein Acrp30 enhances hepatic insulin action." Nat. Med. Aug. 2001; 7(8):947-53.

Bowie, James U. et al., "Deciphering the Message in Protein Sequences: Tolerance to Amino Acid Substitutions," Science, vol. 247:1306-1310 (1990).

Combs, Terry P., et al. "Endogenous glucose production is inhibited by the adipose-derived protein Acrp30," The Journal of Clinical Investigation, vol. 108(12):1875-1881 (2001).

EMBL AC No. BC024094, Mus musculus (2002).
EMBL AC No. AF151803, Homo sapiens (1999).
EMBL AC No. AK012847, Mus musculus (2001).
EMBL AC No. AK025085, Homo sapiens (2000).

Friedman, J.M. "Obesity in the new millennium." Nature. Apr. 6, 2000; 404(6778):632-4.

Fruebis, J., et al. "Proteolytic cleavage product of 30-kDa adipocyte complement-related protein increases fatty acid oxidation in muscle and causes weight loss in mice." Proc Natl Acad Sci USA. Feb. 13, 2001; 98(4):2005-10.

Hotamisligil, G.S. "The role of TNFalpha and TNF receptors in obesity and insulin resistance." J Intern Med. Jun. 1999; 245(6):621-5.

Hu, E., et al. "AdipoQ is a novel adipose-specific gene dysregulated in obesity." J Biol Chem. May 3, 1996; 271 (18):10697-703.

Karpichev, I.V., et al. "Multiple regulatory roles of a novel Saccharomyces cerevisiae protein, encoded by YOL002c, in lipid and phosphate metabolism." J Biol Chem. May 31, 2002; 277(22):19609-17.

Matsuzawa, Y., et al. "Molecular mechanism of metabolic syndrome X: contribution of adipocytokines adipocyte-derived bioactive substances." Ann NY Acad Sci. Nov. 18, 1999; 892:146-54.

Michael, L.F., et al. "Restoration of insulin-sensitive glucose transporter (GLUT4) gene expression in muscle cells by the transcriptional coactivator PGC-1." Proc Natl Acad Sci USA. Mar. 27, 2001; 98(7):3820-5.

Ngo, J. Thomas et al., "Computational Complexity, Protein Structure Prediction, and the Levinthal Paradox," The Protein Folding Problem and Tertiary Structure Prediction, K.M. Merz, Jr., ed., Chapt. 14, pp. 492-495 (1994).

Okazaki, Y., et al. "Analysis of the mouse transcriptome based on functional annotation of 60,770 full-length cDNAs." Nature. Dec. 5, 2002; 420(6915):563-73.

(Continued)

Primary Examiner — Shulamith H Shafer
(74) Attorney, Agent, or Firm — Nelson Mullins Riley & Scarborough LLP; Jeanne M. DiGiorgio, Esq.

(57) ABSTRACT

The object is to isolate and identify human and mouse adiponectin receptors, to provide a novel protein having adiponectin binding ability, and to provide a screening method and screening kit for a ligand, agonist and antagonist to an adiponectin receptor using such protein. To achieve this object, a protein is used, as novel protein having adiponectin binding ability, that is (a) a protein comprising an amino acid sequence according to Seq. No. 2, 4, 6 or 8, or (b) a protein comprising an amino acid sequence according to Seq. No. 2, 4, 6 or 8 with one or more amino acids deleted, replaced or added, and having adiponectin binding ability.

12 Claims, 39 Drawing Sheets

OTHER PUBLICATIONS

Ouchi, N., et al. "Adipocyte-derived plasma protein, adiponectin, suppresses lipid accumulation and class A scavenger receptor expression in human monocyte-derived macrophages." Circulation. Feb. 27, 2001; 103(8):1057-63.

Puigserver, P., et al. "Cytokine stimulation of energy expenditure through p38 MAP kinase activation of PPARgamma coactivator-1." Mol Cell. Nov. 2001; 8(5):971-82.

Reaven, G.M. "The fourth musketeer—from Alexandre Dumas to Claude Bernard." Diabetologia. Jan. 1995; 38 (1):3-13.

Ruderman, N.B., et al. "Malonyl-CoA, fuel sensing, and insulin resistance." Am J Physiol. Jan. 1999; 276(1 Pt 1):E1- E18.

Scheer, A., et al. "Constitutively active mutants of the alpha 1B-adrenergic receptor: role of highly conserved polar amino acids in receptor activation." EMBO J. Jul. 15, 1996; 15(14): 3566-78.

Shimomura, I., et al. "Enhanced expression of PAI-1 in visceral fat: possible contributor to vascular disease in obesity." Nat Med. Jul. 1996; 2(7):800-3.

Shulman, G.I., et al. "Cellular mechanisms of insulin resistance." J Clin Invest. Jul. 2000; 106(2):171-6.

Spiegelman, B.M., et al. "Adipogenesis and obesity: rounding out the big picture." Cell. Nov. 1, 1996; 87(3):377-89.

Steppan, C.M., et al. "The hormone resistin links obesity to diabetes." Nature. Jan. 18, 2001; 409(6818):307-12.

The C. elegans Sequencing Consortium, "Genome Sequence of the Nematode C. elegans: A Platform for Investigating Biology," Science, vol. 282:2012-2018 (1998).

Waterston, R.H., et al. "Initial sequencing and comparative analysis of the mouse genome." Nature. Dec. 5, 2002; 420(6915):520-62.

Wells, James A., "Additivity of Mutational Effects in Proteins," Biochemistry, vol. 29(37:8509-8517 (1990).

Wess, J. "G-protein-coupled receptors: molecular mechanisms involved in receptor activation and selectivity of G-protein recognition." FASEB J. Apr. 1997; 11(5):346-54.

White, R.T., et al. "Human adipsin is identical to complement factor D and is expressed at high levels in adipose tissue." J Biol Chem. May 5, 1992; 267(13):9210-3.

Yamauchi, Toshimasa et al., "Cloning of adiponectin receptors that mediate antidiabetic metabolic effects," Nature, vol. 423:762-769 (2003).

Yamauchi, T., et al. "The fat-derived hormone adiponectin reverses insulin resistance associated with both lipoatrophy and obesity." Nat Med. Aug. 2001; 7(8):941-6.

Yamauchi, T., et al. "Adiponectin stimulates glucose utilization and fatty-acid oxidation by activating AMP-activated protein kinase." Nat Med. Nov. 2002; 8(11):1288-95.

Yamauchi, T., et al. "Globular adiponectin protected ob/ob mice from diabetes and ApoE-deficient mice from atherosclerosis." J Biol Chem. Jan. 24, 2003; 278(4):2461-8.

Yokomizo, T., et al. "A G-protein-coupled receptor for leukotriene B4 that mediates chemotaxis." Nature. Jun. 5, 1997; 387(6633):620-4.

Yokota, T., et al. "Adiponectin, a new member of the family of soluble defense collagens, negatively regulates the growth of myelomonocytic progenitors and the functions of macrophages." Blood. Sep. 1, 2000; 96(5):1723-32.

International Search Report for Application No. PCT/JP03/07515, dated Sep. 16, 2003.

* cited by examiner

LPS:

SEQUENCE LISTING

<160> NUMBER OF SEQ ID NOS: 32

<210> SEQ ID NO 1
<211> LENGTH: 1128
<212> TYPE: DNA
<213> ORGANISM: Homo sapiens
<220> FEATURE:
<221> NAME/KEY: CDS
<222> LOCATION: (1)..(1125)

<400> SEQUENCE: 1

```
atg tct tcc cac aaa gga tct gtg gtg gca cag ggg aat ggg gct cct        48
Met Ser Ser His Lys Gly Ser Val Val Ala Gln Gly Asn Gly Ala Pro
1               5                   10                  15 gcc agt aac agg gaa gct gac acg gtg gaa ctg gct gaa ctg gga ccc        96
Ala Ser Asn Arg Glu Ala Asp Thr Val Glu Leu Ala Glu Leu Gly Pro
            20                  25                  30 ctg cta gaa gag aag ggc aaa cgg gta atc gcc aac cca ccc aaa gct       144
Leu Leu Glu Glu Lys Gly Lys Arg Val Ile Ala Asn Pro Pro Lys Ala
        35                  40                  45 gaa gaa gag caa aca tgc cca gtg ccc cag gaa gaa gag gag gtg           192
Glu Glu Glu Gln Thr Cys Pro Val Pro Gln Glu Glu Glu Glu Val
    50                  55                  60 cgg gta ctg aca ctt ccc ctg caa gcc cac cac gcc atg gag aag atg       240
Arg Val Leu Thr Leu Pro Leu Gln Ala His His Ala Met Glu Lys Met
65                  70                  75                  80 gaa gag ttt gtg tac aag gtc tgg gag gga cgt tgg agg gtc atc cca       288
Glu Glu Phe Val Tyr Lys Val Trp Glu Gly Arg Trp Arg Val Ile Pro
                85                  90                  95 tat gat gtg ctc cct gac tgg cta aag gac aac gac tat ctg cta cat       336
Tyr Asp Val Leu Pro Asp Trp Leu Lys Asp Asn Asp Tyr Leu Leu His
            100                 105                 110 ggt cat aga cct ccc atg ccc tcc ttt cgg gct tgc ttc aag agc atc       384
Gly His Arg Pro Pro Met Pro Ser Phe Arg Ala Cys Phe Lys Ser Ile
        115                 120                 125 ttc cgc att cat aca gaa act ggc aac atc tgg acc cat ctg ctt ggt       432
Phe Arg Ile His Thr Glu Thr Gly Asn Ile Trp Thr His Leu Leu Gly
    130                 135                 140 ttc gtg ctg ttt ctc ttt ttg gga atc ttg acc atg ctc aga cca aat       480
Phe Val Leu Phe Leu Phe Leu Gly Ile Leu Thr Met Leu Arg Pro Asn
145                 150                 155                 160 atg tac ttc atg gcc cct cta cag gag aag gtg gtt ttt ggg atg ttc       528
Met Tyr Phe Met Ala Pro Leu Gln Glu Lys Val Val Phe Gly Met Phe
                165                 170                 175 ttt ttg ggt gca gtg ctc tgc ctc agc ttc tcc tgg ctc ttt cac acc       576
Phe Leu Gly Ala Val Leu Cys Leu Ser Phe Ser Trp Leu Phe His Thr
            180                 185                 190 gtc tat tgt cat tca gag aaa gtc tct cgg act ttt tcc aaa ctg gac       624
Val Tyr Cys His Ser Glu Lys Val Ser Arg Thr Phe Ser Lys Leu Asp
        195                 200                 205 tat tca ggg att gct ctt cta att atg ggg agc ttt gtc ccc tgg ctc       672
Tyr Ser Gly Ile Ala Leu Leu Ile Met Gly Ser Phe Val Pro Trp Leu
    210                 215                 220 tat tat tcc ttc tac tgc tcc cca cag cca cgg ctc atc tac ctc tcc       720
Tyr Tyr Ser Phe Tyr Cys Ser Pro Gln Pro Arg Leu Ile Tyr Leu Ser
225                 230                 235                 240 atc gtc tgt gtc ctg ggc att tct gcc att att gtg gcg cag tgg gac       768
Ile Val Cys Val Leu Gly Ile Ser Ala Ile Ile Val Ala Gln Trp Asp
                245                 250                 255 cgg ttt gcc act cct aag cac cgg cag aca aga gca ggc gtg ttc ctg       816
```

```
gga ctt ggc ttg agt ggc gtc gtg ccc acc atg cac ttt act atc gct    864
Gly Leu Gly Leu Ser Gly Val Val Pro Thr Met His Phe Thr Ile Ala
        275                 280                 285 gag ggc ttt gtc aag gcc acc aca gtg ggc cag atg ggc tgg ttc ttc    912
Glu Gly Phe Val Lys Ala Thr Thr Val Gly Gln Met Gly Trp Phe Phe
    290                 295                 300 ctc atg gct gtg atg tac atc act gga gct ggc ctt tat gct gct cga    960
Leu Met Ala Val Met Tyr Ile Thr Gly Ala Gly Leu Tyr Ala Ala Arg
305                 310                 315                 320 att cct gag cgc ttc ttt cct gga aaa ttt gac ata tgg ttc cag tct   1008
Ile Pro Glu Arg Phe Phe Pro Gly Lys Phe Asp Ile Trp Phe Gln Ser
                325                 330                 335 cat cag att ttc cat gtc ctg gtg gtg gca gca gcc ttt gtc cac ttc   1056
His Gln Ile Phe His Val Leu Val Val Ala Ala Ala Phe Val His Phe
            340                 345                 350 tat gga gtc tcc aac ctt cag gaa ttc cgt tac ggc cta gaa ggc ggc   1104
Tyr Gly Val Ser Asn Leu Gln Glu Phe Arg Tyr Gly Leu Glu Gly Gly
        355                 360                 365 tgt act gat gac acc ctt ctc tga                                    1128
Cys Thr Asp Asp Thr Leu Leu
370                 375

<210> SEQ ID NO 2
<211> LENGTH: 375
<212> TYPE: PRT
<213> ORGANISM: Homo sapiens

<400> SEQUENCE: 2

Met Ser Ser His Lys Gly Ser Val Val Ala Gln Gly Asn Gly Ala Pro
1               5                   10                  15

Ala Ser Asn Arg Glu Ala Asp Thr Val Glu Leu Ala Glu Leu Gly Pro
            20                  25                  30

Leu Leu Glu Glu Lys Gly Lys Arg Val Ile Ala Asn Pro Lys Ala
        35                  40                  45

Glu Glu Glu Gln Thr Cys Pro Val Pro Gln Glu Glu Glu Glu Val
    50                  55                  60

Arg Val Leu Thr Leu Pro Leu Gln Ala His His Ala Met Glu Lys Met
65                  70                  75                  80

Glu Glu Phe Val Tyr Lys Val Trp Glu Gly Arg Trp Arg Val Ile Pro
                85                  90                  95

Tyr Asp Val Leu Pro Asp Trp Leu Lys Asp Asn Asp Tyr Leu Leu His
            100                 105                 110

Gly His Arg Pro Pro Met Pro Ser Phe Arg Ala Cys Phe Lys Ser Ile
        115                 120                 125

Phe Arg Ile His Thr Glu Thr Gly Asn Ile Trp Thr His Leu Leu Gly
    130                 135                 140

Phe Val Leu Phe Leu Phe Leu Gly Ile Leu Thr Met Leu Arg Pro Asn
145                 150                 155                 160

Met Tyr Phe Met Ala Pro Leu Gln Glu Lys Val Val Phe Gly Met Phe
                165                 170                 175

Phe Leu Gly Ala Val Leu Cys Leu Ser Phe Ser Trp Leu Phe His Thr
            180                 185                 190

Val Tyr Cys His Ser Glu Lys Val Ser Arg Thr Phe Ser Lys Leu Asp
        195                 200                 205

Tyr Ser Gly Ile Ala Leu Leu Ile Met Gly Ser Phe Val Pro Trp Leu
    210                 215                 220
```

```
Tyr Tyr Ser Phe Tyr Cys Ser Pro Gln Pro Arg Leu Ile Tyr Leu Ser
225                 230                 235                 240

Ile Val Cys Val Leu Gly Ile Ser Ala Ile Val Ala Gln Trp Asp
            245                 250                 255

Arg Phe Ala Thr Pro Lys His Arg Gln Thr Arg Ala Gly Val Phe Leu
                260                 265                 270

Gly Leu Gly Leu Ser Gly Val Val Pro Thr Met His Phe Thr Ile Ala
            275                 280                 285

Glu Gly Phe Val Lys Ala Thr Thr Val Gly Gln Met Gly Trp Phe Phe
    290                 295                 300

Leu Met Ala Val Met Tyr Ile Thr Gly Ala Gly Leu Tyr Ala Ala Arg
305                 310                 315                 320

Ile Pro Glu Arg Phe Phe Pro Gly Lys Phe Asp Ile Trp Phe Gln Ser
                325                 330                 335

His Gln Ile Phe His Val Leu Val Ala Ala Ala Phe Val His Phe
            340                 345                 350

Tyr Gly Val Ser Asn Leu Gln Glu Phe Arg Tyr Gly Leu Glu Gly Gly
            355                 360                 365

Cys Thr Asp Asp Thr Leu Leu
    370                 375

<210> SEQ ID NO 3
<211> LENGTH: 900
<212> TYPE: DNA
<213> ORGANISM: Homo sapiens
<220> FEATURE:
<221> NAME/KEY: CDS
<222> LOCATION: (1)..(897)

<400> SEQUENCE: 3 atg gaa aaa atg gaa gaa ttt gtt tgt aag gta tgg gaa ggt cgg tgg    48
Met Glu Lys Met Glu Glu Phe Val Cys Lys Val Trp Glu Gly Arg Trp
1               5                   10                  15 cga gtg atc cct cat gat gta cta cca gac tgg ctc aag gat aat gac    96
Arg Val Ile Pro His Asp Val Leu Pro Asp Trp Leu Lys Asp Asn Asp
                20                  25                  30 ttc ctc ttg cat gga cac cgg cct cct atg cct tct ttc cgg gcc tgt   144
Phe Leu Leu His Gly His Arg Pro Pro Met Pro Ser Phe Arg Ala Cys
            35                  40                  45 ttt aag agc att ttc aga ata cac aca gaa aca ggc aac att tgg aca   192
Phe Lys Ser Ile Phe Arg Ile His Thr Glu Thr Gly Asn Ile Trp Thr
        50                  55                  60 cat ctc tta ggt tgt gta ttc ttc ctg tgc ctg ggg atc ttt tat atg   240
His Leu Leu Gly Cys Val Phe Phe Leu Cys Leu Gly Ile Phe Tyr Met
65                  70                  75                  80 ttt cgc cca aat atc tcc ttt gtg gcc cct ctg caa gag aag gtg gtc   288
Phe Arg Pro Asn Ile Ser Phe Val Ala Pro Leu Gln Glu Lys Val Val
                85                  90                  95 ttt gga tta ttt ttc tta gga gcc att ctc tgc ctt tct ttt tca tgg   336
Phe Gly Leu Phe Phe Leu Gly Ala Ile Leu Cys Leu Ser Phe Ser Trp
            100                 105                 110 ctc ttc cac aca gtc tac tgc cac tca gag ggg gtc tct cgg ctc ttc   384
Leu Phe His Thr Val Tyr Cys His Ser Glu Gly Val Ser Arg Leu Phe
        115                 120                 125 tct aaa ctg gat tac tct ggt att gct ctt ctg att atg gga agt ttt   432
Ser Lys Leu Asp Tyr Ser Gly Ile Ala Leu Leu Ile Met Gly Ser Phe
    130                 135                 140 gtt cct tgg ctt tat tat tct ttc tac tgt aat cca caa cct tgc ttc   480
Val Pro Trp Leu Tyr Tyr Ser Phe Tyr Cys Asn Pro Gln Pro Cys Phe
```

```
                145                 150                 155                 160
atc tac ttg att gtc atc tgt gtg ctg ggc att gca gcc att ata gtc        528
Ile Tyr Leu Ile Val Ile Cys Val Leu Gly Ile Ala Ala Ile Ile Val
                165                 170                 175 tcc cag tgg gac atg ttt gcc acc cct cag tat cgg gga gta aga gca        576
Ser Gln Trp Asp Met Phe Ala Thr Pro Gln Tyr Arg Gly Val Arg Ala
        180                 185                 190 gga gtg ttt ttg ggc cta ggc ctg agt gga atc att cct acc ttg cac        624
Gly Val Phe Leu Gly Leu Gly Leu Ser Gly Ile Ile Pro Thr Leu His
            195                 200                 205 tat gtc atc tcg gag ggg ttc ctt aag gcc gcc acc ata ggg cag ata        672
Tyr Val Ile Ser Glu Gly Phe Leu Lys Ala Ala Thr Ile Gly Gln Ile
    210                 215                 220 ggc tgg ttg atg ctg atg gcc agc ctc tac atc aca gga gct gcc ctg        720
Gly Trp Leu Met Leu Met Ala Ser Leu Tyr Ile Thr Gly Ala Ala Leu
225                 230                 235                 240 tat gct gcc cgg atc ccc gaa cgc ttt ttc cct ggc aaa tgt gac atc        768
Tyr Ala Ala Arg Ile Pro Glu Arg Phe Phe Pro Gly Lys Cys Asp Ile
                245                 250                 255 tgg ttt cac tct cat cag ctg ttt cat atc ttt gtg gtt gct gga gct        816
Trp Phe His Ser His Gln Leu Phe His Ile Phe Val Val Ala Gly Ala
        260                 265                 270 ttt gtt cac ttc cat ggt gtc tca aac ctc cag gag ttt cgt ttc atg        864
Phe Val His Phe His Gly Val Ser Asn Leu Gln Glu Phe Arg Phe Met
            275                 280                 285 atc ggc ggg ggc tgc agt gaa gag gat gca ctg tga                        900
Ile Gly Gly Gly Cys Ser Glu Glu Asp Ala Leu
    290                 295

<210> SEQ ID NO 4
<211> LENGTH: 299
<212> TYPE: PRT
<213> ORGANISM: Homo sapiens

<400> SEQUENCE: 4

Met Glu Lys Met Glu Glu Phe Val Cys Lys Val Trp Glu Gly Arg Trp
1               5                   10                  15

Arg Val Ile Pro His Asp Val Leu Pro Asp Trp Leu Lys Asp Asn Asp
            20                  25                  30

Phe Leu Leu His Gly His Arg Pro Pro Met Pro Ser Phe Arg Ala Cys
        35                  40                  45

Phe Lys Ser Ile Phe Arg Ile His Thr Glu Thr Gly Asn Ile Trp Thr
    50                  55                  60

His Leu Leu Gly Cys Val Phe Phe Leu Cys Leu Gly Ile Phe Tyr Met
65                  70                  75                  80

Phe Arg Pro Asn Ile Ser Phe Val Ala Pro Leu Gln Glu Lys Val Val
                85                  90                  95

Phe Gly Leu Phe Phe Leu Gly Ala Ile Leu Cys Leu Ser Phe Ser Trp
            100                 105                 110

Leu Phe His Thr Val Tyr Cys His Ser Glu Gly Val Ser Arg Leu Phe
        115                 120                 125

Ser Lys Leu Asp Tyr Ser Gly Ile Ala Leu Leu Ile Met Gly Ser Phe
    130                 135                 140

Val Pro Trp Leu Tyr Tyr Ser Phe Tyr Cys Asn Pro Gln Pro Cys Phe
145                 150                 155                 160

Ile Tyr Leu Ile Val Ile Cys Val Leu Gly Ile Ala Ala Ile Ile Val
                165                 170                 175

Ser Gln Trp Asp Met Phe Ala Thr Pro Gln Tyr Arg Gly Val Arg Ala
```

```
                     180                 185                 190
Gly Val Phe Leu Gly Leu Gly Leu Ser Gly Ile Ile Pro Thr Leu His
            195                 200                 205

Tyr Val Ile Ser Glu Gly Phe Leu Lys Ala Ala Thr Ile Gly Gln Ile
            210                 215                 220

Gly Trp Leu Met Leu Met Ala Ser Leu Tyr Ile Thr Gly Ala Ala Leu
225                 230                 235                 240

Tyr Ala Ala Arg Ile Pro Glu Arg Phe Phe Pro Gly Lys Cys Asp Ile
            245                 250                 255

Trp Phe His Ser His Gln Leu Phe His Ile Phe Val Val Ala Gly Ala
            260                 265                 270

Phe Val His Phe His Gly Val Ser Asn Leu Gln Glu Phe Arg Phe Met
            275                 280                 285

Ile Gly Gly Gly Cys Ser Glu Glu Asp Ala Leu
            290                 295

<210> SEQ ID NO 5
<211> LENGTH: 1128
<212> TYPE: DNA
<213> ORGANISM: Mus musculus
<220> FEATURE:
<221> NAME/KEY: CDS
<222> LOCATION: (1)..(1125)

<400> SEQUENCE: 5 atg tct tcc cac aaa ggc tct gcc ggg gca caa ggc aat ggg gct cct      48
Met Ser Ser His Lys Gly Ser Ala Gly Ala Gln Gly Asn Gly Ala Pro
1               5                   10                  15 tct ggt aac aga gaa gct gac aca gtg gag ctg gct gag ctg ggg ccc      96
Ser Gly Asn Arg Glu Ala Asp Thr Val Glu Leu Ala Glu Leu Gly Pro
                20                  25                  30 ctg ctg gag gag aag ggc aag cgg gca gcc agc agc cca gcc aag gct     144
Leu Leu Glu Glu Lys Gly Lys Arg Ala Ala Ser Ser Pro Ala Lys Ala
            35                  40                  45 gag gaa gat caa gca tgc ccg gtg cct cag gaa gag gag gag gtg         192
Glu Glu Asp Gln Ala Cys Pro Val Pro Gln Glu Glu Glu Glu Val
        50                  55                  60 cgg gtg ctg acg ctt cct ctg caa gcc cac cat gcc atg gag aag atg     240
Arg Val Leu Thr Leu Pro Leu Gln Ala His His Ala Met Glu Lys Met
65                  70                  75                  80 gag gag ttc gtg tat aag gtc tgg gag gga cgt tgg aga gtc atc ccg     288
Glu Glu Phe Val Tyr Lys Val Trp Glu Gly Arg Trp Arg Val Ile Pro
                85                  90                  95 tat gat gtg ctt cct gac tgg ctg aaa gac aac gac tac ctg cta cat     336
Tyr Asp Val Leu Pro Asp Trp Leu Lys Asp Asn Asp Tyr Leu Leu His
                100                 105                 110 ggc cac aga cca cct atg ccc tcc ttt cgg gct tgc ttc aag agc atc     384
Gly His Arg Pro Pro Met Pro Ser Phe Arg Ala Cys Phe Lys Ser Ile
            115                 120                 125 ttc cgc atc cac aca gag act ggc aac atc tgg aca cat ctg ctt ggt     432
Phe Arg Ile His Thr Glu Thr Gly Asn Ile Trp Thr His Leu Leu Gly
        130                 135                 140 ttt gtg cta ttt ctc ttt ctg gga atc ttg acg atg ctg aga cca aat     480
Phe Val Leu Phe Leu Phe Leu Gly Ile Leu Thr Met Leu Arg Pro Asn
145                 150                 155                 160 atg tac ttc atg gct ccc ctg cag gag aag gtg gtc ttc ggg atg ttc     528
Met Tyr Phe Met Ala Pro Leu Gln Glu Lys Val Val Phe Gly Met Phe
                165                 170                 175 ttc ctg ggc gcg gtg ctc tgc ctc agt ttc tcc tgg ctc ttc cac act     576
Phe Leu Gly Ala Val Leu Cys Leu Ser Phe Ser Trp Leu Phe His Thr
```

```
                  180                 185                 190
gtc tac tgt cat tca gag aag gtc tct cgg act ttt tcc aaa ctg gac    624
Val Tyr Cys His Ser Glu Lys Val Ser Arg Thr Phe Ser Lys Leu Asp
                  195                 200                 205 tat tca ggg att gct cta ctg att atg ggg agc ttc gtt ccc tgg ctc    672
Tyr Ser Gly Ile Ala Leu Leu Ile Met Gly Ser Phe Val Pro Trp Leu
    210                 215                 220 tat tac tcc ttc tac tgc tcc cca cag ccg cgg ctc atc tac ctc tcc    720
Tyr Tyr Ser Phe Tyr Cys Ser Pro Gln Pro Arg Leu Ile Tyr Leu Ser
225                 230                 235                 240 atc gtc tgt gtc ctg ggc atc tct gcc atc att gtg gca cag tgg gac    768
Ile Val Cys Val Leu Gly Ile Ser Ala Ile Ile Val Ala Gln Trp Asp
                245                 250                 255 cgg ttt gcc act ccc aag cac cgg cag aca aga gca gga gtg ttc ctg    816
Arg Phe Ala Thr Pro Lys His Arg Gln Thr Arg Ala Gly Val Phe Leu
            260                 265                 270 gga ctt ggc ttg agt ggt gtt gta ccc acc atg cac ttt act atc gct    864
Gly Leu Gly Leu Ser Gly Val Val Pro Thr Met His Phe Thr Ile Ala
        275                 280                 285 gag ggc ttt gtc aag gcc acc acg gtg ggc cag atg ggc tgg ttc ttc    912
Glu Gly Phe Val Lys Ala Thr Thr Val Gly Gln Met Gly Trp Phe Phe
    290                 295                 300 ctc atg gct gtg atg tac atc acc ggc gcc ggc ctg tat gct gct cgg    960
Leu Met Ala Val Met Tyr Ile Thr Gly Ala Gly Leu Tyr Ala Ala Arg
305                 310                 315                 320 att cct gag cgc ttc ttc cct gga aaa ttt gac atc tgg ttc cag tct   1008
Ile Pro Glu Arg Phe Phe Pro Gly Lys Phe Asp Ile Trp Phe Gln Ser
                325                 330                 335 cat cag att ttc cac gtc ctg gtg gtg gca gca gct ttc gtc cac ttc   1056
His Gln Ile Phe His Val Leu Val Val Ala Ala Ala Phe Val His Phe
            340                 345                 350 tat ggt gtg tcc aac ctt cag gaa ttc cgt tat ggc cta gaa ggt ggc   1104
Tyr Gly Val Ser Asn Leu Gln Glu Phe Arg Tyr Gly Leu Glu Gly Gly
        355                 360                 365 tgt acc gac gac tcc ctt ctc tga                                   1128
Cys Thr Asp Asp Ser Leu Leu
    370                 375

<210> SEQ ID NO 6
<211> LENGTH: 375
<212> TYPE: PRT
<213> ORGANISM: Mus musculus

<400> SEQUENCE: 6

Met Ser Ser His Lys Gly Ser Ala Gly Ala Gln Gly Asn Gly Ala Pro
1               5                   10                  15

Ser Gly Asn Arg Glu Ala Asp Thr Val Glu Leu Ala Glu Leu Gly Pro
            20                  25                  30

Leu Leu Glu Glu Lys Gly Lys Arg Ala Ala Ser Ser Pro Ala Lys Ala
        35                  40                  45

Glu Glu Asp Gln Ala Cys Pro Val Pro Gln Glu Glu Glu Glu Glu Val
    50                  55                  60

Arg Val Leu Thr Leu Pro Leu Gln Ala His His Ala Met Glu Lys Met
65                  70                  75                  80

Glu Glu Phe Val Tyr Lys Val Trp Glu Gly Arg Trp Arg Val Ile Pro
                85                  90                  95

Tyr Asp Val Leu Pro Asp Trp Leu Lys Asp Asn Asp Tyr Leu Leu His
                100                 105                 110

Gly His Arg Pro Pro Met Pro Ser Phe Arg Ala Cys Phe Lys Ser Ile
```

```
                   115                 120                 125
Phe Arg Ile His Thr Glu Thr Gly Asn Ile Trp Thr His Leu Leu Gly
    130                 135                 140

Phe Val Leu Phe Leu Phe Leu Gly Ile Leu Thr Met Leu Arg Pro Asn
145                 150                 155                 160

Met Tyr Phe Met Ala Pro Leu Gln Glu Lys Val Val Phe Gly Met Phe
                165                 170                 175

Phe Leu Gly Ala Val Leu Cys Leu Ser Phe Ser Trp Leu Phe His Thr
            180                 185                 190

Val Tyr Cys His Ser Glu Lys Val Ser Arg Thr Phe Ser Lys Leu Asp
        195                 200                 205

Tyr Ser Gly Ile Ala Leu Leu Ile Met Gly Ser Phe Val Pro Trp Leu
    210                 215                 220

Tyr Tyr Ser Phe Tyr Cys Ser Pro Gln Pro Arg Leu Ile Tyr Leu Ser
225                 230                 235                 240

Ile Val Cys Val Leu Gly Ile Ser Ala Ile Ile Val Ala Gln Trp Asp
                245                 250                 255

Arg Phe Ala Thr Pro Lys His Arg Gln Thr Arg Ala Gly Val Phe Leu
            260                 265                 270

Gly Leu Gly Leu Ser Gly Val Val Pro Thr Met His Phe Thr Ile Ala
        275                 280                 285

Glu Gly Phe Val Lys Ala Thr Thr Val Gly Gln Met Gly Trp Phe Phe
    290                 295                 300

Leu Met Ala Val Met Tyr Ile Thr Gly Ala Gly Leu Tyr Ala Ala Arg
305                 310                 315                 320

Ile Pro Glu Arg Phe Phe Pro Gly Lys Phe Asp Ile Trp Phe Gln Ser
                325                 330                 335

His Gln Ile Phe His Val Leu Val Ala Ala Ala Phe Val His Phe
            340                 345                 350

Tyr Gly Val Ser Asn Leu Gln Glu Phe Arg Tyr Gly Leu Glu Gly Gly
        355                 360                 365

Cys Thr Asp Asp Ser Leu Leu
    370                 375

<210> SEQ ID NO 7
<211> LENGTH: 936
<212> TYPE: DNA
<213> ORGANISM: Mus musculus
<220> FEATURE:
<221> NAME/KEY: CDS
<222> LOCATION: (1)..(933)

<400> SEQUENCE: 7 atg ggc atg tcc ccg ctc cta cag gcc cat cat gct atg gaa cga atg      48
Met Gly Met Ser Pro Leu Leu Gln Ala His His Ala Met Glu Arg Met
1               5                   10                  15 gaa gag ttt gtt tgt aag gtg tgg gaa ggc cga tgg cga gtg atc cct      96
Glu Glu Phe Val Cys Lys Val Trp Glu Gly Arg Trp Arg Val Ile Pro
            20                  25                  30 cac gat gtg cta ccg gat tgg ctt aag gat aat gac ttc ctt ctc cat     144
His Asp Val Leu Pro Asp Trp Leu Lys Asp Asn Asp Phe Leu Leu His
        35                  40                  45 gga cac cgg cct cct atg cct tcc ttt cgg gcc tgt ttt aag agc att     192
Gly His Arg Pro Pro Met Pro Ser Phe Arg Ala Cys Phe Lys Ser Ile
    50                  55                  60 ttt aga ata cac aca gag acg ggc aac att tgg aca cat ctc cta ggt     240
Phe Arg Ile His Thr Glu Thr Gly Asn Ile Trp Thr His Leu Leu Gly
65                  70                  75                  80
```

```
tgt gta ttc ttc ctg tgc ctg ggg atc ttt tat atg ttt cgc cca aat    288
Cys Val Phe Phe Leu Cys Leu Gly Ile Phe Tyr Met Phe Arg Pro Asn
             85                  90                  95 ata tct ttt gtg gcc cct ctg caa gag aaa gtg gtc ttt ggc ttg ttc    336
Ile Ser Phe Val Ala Pro Leu Gln Glu Lys Val Val Phe Gly Leu Phe
        100                 105                 110 ttc ttg gga gcc att ctc tgc ctt tcc ttt tca tgg ctc ttc cac acg    384
Phe Leu Gly Ala Ile Leu Cys Leu Ser Phe Ser Trp Leu Phe His Thr
    115                 120                 125 gtg tac tgc cac tca gaa ggg gtc tcc cga ctc ttc tct aaa ttg gat    432
Val Tyr Cys His Ser Glu Gly Val Ser Arg Leu Phe Ser Lys Leu Asp
130                 135                 140 tac tct ggt att gct ctt ctg atc atg gga agt ttt gtt cct tgg ctt    480
Tyr Ser Gly Ile Ala Leu Leu Ile Met Gly Ser Phe Val Pro Trp Leu
145                 150                 155                 160 tat tat tct ttc tac tgt aac cca caa cct tgc ttc atc tac ctg att    528
Tyr Tyr Ser Phe Tyr Cys Asn Pro Gln Pro Cys Phe Ile Tyr Leu Ile
                165                 170                 175 gtc atc tgt gtg ctg ggc att gca gcc att atc gtc tct cag tgg gac    576
Val Ile Cys Val Leu Gly Ile Ala Ala Ile Ile Val Ser Gln Trp Asp
            180                 185                 190 atg ttt gcc acc cct cag tat cgg ggg gtc aga gca gga gtg ttc gtg    624
Met Phe Ala Thr Pro Gln Tyr Arg Gly Val Arg Ala Gly Val Phe Val
        195                 200                 205 ggc tta ggc ctg agt gga atc atc cct acc ttg cat tat gtc atc tca    672
Gly Leu Gly Leu Ser Gly Ile Ile Pro Thr Leu His Tyr Val Ile Ser
    210                 215                 220 gaa ggg ttc ctg aag gct gcc acc ata ggg cag ata ggc tgg cta atg    720
Glu Gly Phe Leu Lys Ala Ala Thr Ile Gly Gln Ile Gly Trp Leu Met
225                 230                 235                 240 ctt atg gct agc ctc tat atc acc gga gct gcc ctc tat gcg gcc cgt    768
Leu Met Ala Ser Leu Tyr Ile Thr Gly Ala Ala Leu Tyr Ala Ala Arg
                245                 250                 255 atc cct gag cgc ttc ttt cct ggc aaa tgt gac atc tgg ttt cac tct    816
Ile Pro Glu Arg Phe Phe Pro Gly Lys Cys Asp Ile Trp Phe His Ser
            260                 265                 270 cat cag ctc ttc cac atc ttt gtg gtt gct ggt gcc ttt gtt cac ttc    864
His Gln Leu Phe His Ile Phe Val Val Ala Gly Ala Phe Val His Phe
        275                 280                 285 cac gga gtc tca aac ctg cag gaa ttt cgt ttc atg att ggc ggg ggc    912
His Gly Val Ser Asn Leu Gln Glu Phe Arg Phe Met Ile Gly Gly Gly
    290                 295                 300 tgc act gaa gag gat gca ctg tga                                    936
Cys Thr Glu Glu Asp Ala Leu
305                 310

<210> SEQ ID NO 8
<211> LENGTH: 311
<212> TYPE: PRT
<213> ORGANISM: Mus musculus

<400> SEQUENCE: 8

Met Gly Met Ser Pro Leu Leu Gln Ala His His Ala Met Glu Arg Met
1               5                   10                  15

Glu Glu Phe Val Cys Lys Val Trp Glu Gly Arg Trp Arg Val Ile Pro
            20                  25                  30

His Asp Val Leu Pro Asp Trp Leu Lys Asp Asn Asp Phe Leu Leu His
        35                  40                  45

Gly His Arg Pro Pro Met Pro Ser Phe Arg Ala Cys Phe Lys Ser Ile
    50                  55                  60
```

```
Phe Arg Ile His Thr Glu Thr Gly Asn Ile Trp Thr His Leu Leu Gly
 65                  70                  75                  80

Cys Val Phe Phe Leu Cys Leu Gly Ile Phe Tyr Met Phe Arg Pro Asn
                 85                  90                  95

Ile Ser Phe Val Ala Pro Leu Gln Glu Lys Val Val Phe Gly Leu Phe
            100                 105                 110

Phe Leu Gly Ala Ile Leu Cys Leu Ser Phe Ser Trp Leu Phe His Thr
        115                 120                 125

Val Tyr Cys His Ser Glu Gly Val Ser Arg Leu Phe Ser Lys Leu Asp
    130                 135                 140

Tyr Ser Gly Ile Ala Leu Leu Ile Met Gly Ser Phe Val Pro Trp Leu
145                 150                 155                 160

Tyr Tyr Ser Phe Tyr Cys Asn Pro Gln Pro Cys Phe Ile Tyr Leu Ile
                165                 170                 175

Val Ile Cys Val Leu Gly Ile Ala Ala Ile Val Ser Gln Trp Asp
            180                 185                 190

Met Phe Ala Thr Pro Gln Tyr Arg Gly Val Arg Ala Gly Val Phe Val
        195                 200                 205

Gly Leu Gly Leu Ser Gly Ile Ile Pro Thr Leu His Tyr Val Ile Ser
    210                 215                 220

Glu Gly Phe Leu Lys Ala Ala Thr Ile Gly Gln Ile Gly Trp Leu Met
225                 230                 235                 240

Leu Met Ala Ser Leu Tyr Ile Thr Gly Ala Ala Leu Tyr Ala Ala Arg
                245                 250                 255

Ile Pro Glu Arg Phe Phe Pro Gly Lys Cys Asp Ile Trp Phe His Ser
            260                 265                 270

His Gln Leu Phe His Ile Phe Val Val Ala Gly Ala Phe Val His Phe
        275                 280                 285

His Gly Val Ser Asn Leu Gln Glu Phe Arg Phe Met Ile Gly Gly
    290                 295                 300

Cys Thr Glu Glu Asp Ala Leu
305                 310

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide: 5' primer

<400> SEQUENCE: 9
agccctcact ccttctctag                                          20

<210> SEQ ID NO 10
<211> LENGTH: 26
<212> TYPE: DNA
<213> ORGANISM: Artificial Sequence
<220> FEATURE:
<223> OTHER INFORMATION: Synthetic oligonucleotide: 3' primer

<400> SEQUENCE: 10
acctacaggt ggggtctttc attccc                                    26

<210> SEQ ID NO 11
<211> LENGTH: 23
<212> TYPE: DNA
<213> ORGANISM: Artificial Sequence
<220> FEATURE:
<223> OTHER INFORMATION: Synthetic oligonucleotide: siRNA
```

```
                               Unrelated-sense

<400> SEQUENCE: 11
gugcgcugcu ggugccaacc ctt                                              23

<210> SEQ ID NO 12
<211> LENGTH: 23
<212> TYPE: DNA
<213> ORGANISM: Artificial Sequence
<220> FEATURE:
<223> OTHER INFORMATION: Synthetic oligonucleotide: siRNA
      Unrelated-antisense

<400> SEQUENCE: 12
ggguuggcac cagcagcgca ctt                                              23

<210> SEQ ID NO 13
<211> LENGTH: 23
<212> TYPE: DNA
<213> ORGANISM: Artificial Sequence
<220> FEATURE:
<223> OTHER INFORMATION: Synthetic oligonucleotide: siRNA mAdipoR1-sense

<400> SEQUENCE: 13
gagacuggca acaucuggac att                                              23

<210> SEQ ID NO 14
<211> LENGTH: 23
<212> TYPE: DNA
<213> ORGANISM: Artificial Sequence
<220> FEATURE:
<223> OTHER INFORMATION: Synthetic oligonucleotide: siRNA
      mAdipoR1-antisense

<400> SEQUENCE: 14
uguccagaug uugccagucu ctt                                              23

<210> SEQ ID NO 15
<211> LENGTH: 23
<212> TYPE: DNA
<213> ORGANISM: Artificial Sequence
<220> FEATURE:
<223> OTHER INFORMATION: Synthetic oligonucleotide: siRNA mAdipoR2-sense

<400> SEQUENCE: 15
gcuuagagac accuguuugu utt                                              23

<210> SEQ ID NO 16
<211> LENGTH: 23
<212> TYPE: DNA
<213> ORGANISM: Artificial Sequence
<220> FEATURE:
<223> OTHER INFORMATION: Synthetic oligonucleotide: siRNA
      mAdipoR2-antisense

<400> SEQUENCE: 16
aacaaacagg ugucucuaag ctt                                              23

<210> SEQ ID NO 17
<211> LENGTH: 23
<212> TYPE: DNA
<213> ORGANISM: Artificial Sequence
<220> FEATURE:
<223> OTHER INFORMATION: Synthetic oligonucleotide: siRNA hAdipoR1-sense

<400> SEQUENCE: 17
ggacaacgac uaucugcuac att                                              23
```

<210> SEQ ID NO 18
<211> LENGTH: 23
<212> TYPE: DNA
<213> ORGANISM: Artificial Sequence
<220> FEATURE:
<223> OTHER INFORMATION: Synthetic oligonucleotide: siRNA
      hAdipoR1-antisense

<400> SEQUENCE: 18
uguagcagau agucguuguc ctt                                          23

<210> SEQ ID NO 19
<211> LENGTH: 23
<212> TYPE: DNA
<213> ORGANISM: Artificial Sequence
<220> FEATURE:
<223> OTHER INFORMATION: Synthetic oligonucleotide: siRNA hAdipoR2-sense

<400> SEQUENCE: 19
ggaguuucgu uucaugaucg gtt                                          23

<210> SEQ ID NO 20
<211> LENGTH: 23
<212> TYPE: DNA
<213> ORGANISM: Artificial Sequence
<220> FEATURE:
<223> OTHER INFORMATION: Synthetic oligonucleotide: siRNA
      hAdipoR2-antisense

<400> SEQUENCE: 20
ccgaucauga aacgaaacuc ctt                                          23

<210> SEQ ID NO 21
<211> LENGTH: 22
<212> TYPE: DNA
<213> ORGANISM: Artificial Sequence
<220> FEATURE:
<223> OTHER INFORMATION: Synthetic oligonucleotide: Forward primer

<400> SEQUENCE: 21
acgttggaga gtcatcccgt at                                           22

<210> SEQ ID NO 22
<211> LENGTH: 21
<212> TYPE: DNA
<213> ORGANISM: Artificial Sequence
<220> FEATURE:
<223> OTHER INFORMATION: Synthetic oligonucleotide: Reverse primer

<400> SEQUENCE: 22
ctctgtgtgg atgcggaaga t                                            21

<210> SEQ ID NO 23
<211> LENGTH: 25
<212> TYPE: DNA
<213> ORGANISM: Artificial Sequence
<220> FEATURE:
<223> OTHER INFORMATION: Synthetic oligonucleotide: Probe

<400> SEQUENCE: 23
cctgctacat ggccacagac cacct                                        25

<210> SEQ ID NO 24
<211> LENGTH: 23
<212> TYPE: DNA
<213> ORGANISM: Artificial Sequence

```
<220> FEATURE:
<223> OTHER INFORMATION: Synthetic oligonucleotide: Forward primer

<400> SEQUENCE: 24
tcccaggaag atgaagggtt tat                                           23

<210> SEQ ID NO 25
<211> LENGTH: 22
<212> TYPE: DNA
<213> ORGANISM: Artificial Sequence
<220> FEATURE:
<223> OTHER INFORMATION: Synthetic oligonucleotide: Reverse primer

<400> SEQUENCE: 25
ttccattcgt tcgatagcat ga                                            22

<210> SEQ ID NO 26
<211> LENGTH: 22
<212> TYPE: DNA
<213> ORGANISM: Artificial Sequence
<220> FEATURE:
<223> OTHER INFORMATION: Synthetic oligonucleotide: Probe

<400> SEQUENCE: 26
atgtccccgc tcctacaggc cc                                            22

<210> SEQ ID NO 27
<211> LENGTH: 22
<212> TYPE: DNA
<213> ORGANISM: Artificial Sequence
<220> FEATURE:
<223> OTHER INFORMATION: Synthetic oligonucleotide: Forward primer

<400> SEQUENCE: 27
ttcttcctca tggctgtgat gt                                            22

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide: Reverse primer

<400> SEQUENCE: 28
aagaagcgct caggaattcg                                               20

<210> SEQ ID NO 29
<211> LENGTH: 25
<212> TYPE: DNA
<213> ORGANISM: Artificial Sequence
<220> FEATURE:
<223> OTHER INFORMATION: Synthetic oligonucleotide: Probe

<400> SEQUENCE: 29
tcactggagc tggcctttat gctgc                                         25

<210> SEQ ID NO 30
<211> LENGTH: 22
<212> TYPE: DNA
<213> ORGANISM: Artificial Sequence
<220> FEATURE:
<223> OTHER INFORMATION: Synthetic oligonucleotide: Forward primer

<400> SEQUENCE: 30
atagggcaga taggctggtt ga                                            22
```

```
<210> SEQ ID NO 31
<211> LENGTH: 18
<212> TYPE: DNA
<213> ORGANISM: Artificial Sequence
<220> FEATURE:
<223> OTHER INFORMATION: Synthetic oligonucleotide: Reverse primer

<400> SEQUENCE: 31
ggatccgggc agcataca                                                 18

<210> SEQ ID NO 32
<211> LENGTH: 27
<212> TYPE: DNA
<213> ORGANISM: Artificial Sequence
<220> FEATURE:
<223> OTHER INFORMATION: Synthetic oligonucleotide: Probe

<400> SEQUENCE: 32
ctgatggcca gcctctacat cacagga                                       27
```

ADIPONECTIN RECEPTOR AND GENE ENCODING THE SAME

RELATED APPLICATIONS

This application is a divisional of U.S. application Ser. No. 12/322,111 filed Jan. 29, 2009 which is a divisional of U.S. application Ser. No. 11/598,474 filed Nov. 13, 2006, which is a divisional of U.S. application Ser. No. 10/799,943 filed Mar. 11, 2004, which is continuation of PCT/JP03/07515 filed Jun. 12, 2003, which claims priority to Japanese Application No. 2002-383738 filed Dec. 29, 2002. Each of the aforementioned applications are hereby incorporated herein by reference in their entirety.

TECHNICAL FIELD

The present invention relates to a novel protein having adiponectin-binding ability, a gene encoding the protein, a recombinant vector containing the gene, a transformant containing the recombinant vector, and an antibody to the protein and a fragment of the antibody. Moreover, the present invention relates to a screening method and a screening kit for a ligand, agonist or antagonist to an adiponectin receptor.

BACKGROUND ART

Obesity is defined as an increased mass of adipose tissue, and is associated with a higher risk of cardiovascular and metabolic disorders such as diabetes, hyperlipidemia and coronary heart disease (Reaven, G. M., *Diabetologia* 38, 3-13 (1995); Spiegelman, B. M. et al, *Cell* 87, 377-389 (1996)). Impaired glucose and lipid metabolism, a hallmark of obesity and type 2 diabetes, causes increased lipid storage in insulin target tissues such as muscle and liver, thereby leading to insulin resistance (Ruderman, N. B. et al, *Am. J. Physiol.* 276, E1-E18 (1999); Shulman, G. I., *J. Clin. Invest.* 106, 171-176 (2000)). The adipose tissue itself serves as the site of triglyceride (TG) storage and free fatty acids (FFA)/glycerol release in response to changing energy demands (Spiegelman, B. M. and Flier, J. S., *Cell* 87, 377-389 (1996)). Adipose tissue also participates in the regulation of various types of energy homeostasis as an important endocrine organ that secretes a number of biologically active substances called "adipokines" (Matsuzawa, Y. et al, *Ann. NY Acad. Sci.* 892, 146-154 (1999)) such as FFA (Shulman, G. I., *J. Clin. Invest.* 106, 171-176 (2000)), adipsin (White, R. T. et al, *J. Biol. Chem.* 267, 9210-9213 (1992)), leptin (Friedman, J. M., *Nature* 404, 632-634 (2000)), plasminogen activator inhibitor-1 (PAI-1) (Shimomura, I. et al, *Nat. Med.* 2, 800-803 (1996)), resistin (Steppan, C. M. et al, *Nature* 409, 307-312. (2001)) and tumor necrosis factor-α (TNF-α) (Hotamisligil, G. S., *J. Intern. Med.* 245, 621-625 (1999)).

Adiponectin or Acrp30 (Hu, E., Liang, P. et al, *J. Biol. Chem.* 271, 10697-10703 (1996) and others) is an adipocyte-derived hormone with multiple biological functions. It has been reported that obesity, type 2 diabetes and coronary heart disease are associated with decreased plasma adiponectin levels, and that adiponectin may have putative anti-atherogenic properties in vitro (Ouchi, N. et al, *Circulation* 103, 1057-1063 (2001); Yokota, T. et al, *Blood* 96, 1723-1732 (2000)). Also, it has been reported that an acute increase in circulating levels of Acrp30 lowers hepatic glucose production (Berg, A. H. et al, *Nat. Med.* 7, 947-953 (2001); Combs, T. P. et al, *J. Clin. Invest.* 108, 1875-1881 (2001)). Also, it has been reported that globular Acrp30 increases fatty acid oxidation in muscle, and causes weight loss in mice (Fruebis, J. et al, *Proc. Natl. Acad. Sci. USA* 98, 2005-2010 (2001)). Also, it has been reported that treatment with adiponectin consisting solely of the globular domain (globular adiponectin or gAd) increases fatty acid oxidation in muscle, thereby ameliorating insulin resistance in lipoatrophic mice and obese mice, while treatment with full-length adiponectin also ameliorates though less than with gAd (Yamauchi, T. et al, *Nat. Med.* 7, 941-946 (2001)).

Recently it has been reported that adiponectin acutely activates AMP kinase (AMPK) in skeletal muscle, thus stimulating fatty acid oxidation and glucose uptake (Yamauchi, T. et al, *Nat. Med.* 8, 1288-1295 (2002)), and that adiponectin chronically activates PPARα, resulting in increased fatty acid oxidation but reduced tissue TG content in the muscles, with these effects being greater with gAd than with full-length adiponectin (Yamauchi, T. et al, *J. Biol. Chem.* 278, 2461-2468 (2002)). Interestingly, in the liver full-length adiponectin alone acutely activates AMPK, causing a reduction in gluconeogenesis-associated molecules and stimulating fatty-acid oxidation, and moreover full-length adiponectin alone chronically activates AMPK, stimulating fatty-acid oxidation and reducing tissue TG levels in the liver. All these changes serve to enhance insulin sensitivity in vivo (Yamauchi, T. et al, *Nat. Med.* 8, 1288-1295 (2002); Yamauchi, T. et al, *J. Biol. Chem.* 278, 2461-2468 (2002)).

These effects of adiponectin are believed to be mediated by receptors on the cell surface, but adiponectin receptors have not been identified, and it is unknown whether the adiponectin receptors in the skeletal muscle and liver differ either structurally or functionally. The inventors identified a gene encoding adiponectin receptors, and discovered from a homology search that yeast YOL002c gene is a homologue (Karpichev, I. V. et al, *Journal of Biological Chemistry* 277, 19609-19617 (2002)). YOL002c encodes a seven transmembrane protein that plays a key role in the metabolic pathways of lipids, such as fatty acid oxidation (Karpichev, I. V. et al, *Journal of Biological Chemistry* 277; 19609-19617 (2002)).

DISCLOSURE OF THE INVENTION

First, it is an object of the present invention to provide a novel protein having adiponectin-binding ability, a gene encoding the protein, a recombinant vector containing the gene, a transformant containing the recombinant vector, and an antibody to the protein and a fragment of the antibody.

Second, it is an object of the present invention to provide a screening method and screening kit for a ligand, agonist or antagonist to an adiponectin receptor.

In order to achieve these objects, the present invention provides the following protein, gene, recombinant vector, transformant and antibody, as well as a screening method and screening kit for a ligand, agonist or antagonist to an adiponectin receptor.

(1) A protein as set forth in (a), or (b) below:

(a) a protein comprising an amino acid sequence according to Seq. No. 2, 4, 6 or 8; or (b) a protein comprising an amino acid sequence according to Seq. No. 2, 4, 6 or 8 with one or more amino acids deleted, replaced or added, and having adiponectin binding ability.

(2) A gene encoding the protein according to the abovementioned (1).

(3) The gene according to the abovementioned (2), comprising DNA as set forth in (c) or (d) below:

(c) DNA comprising a base sequence according to Seq. No. 1, 3, 5 or 7; or (d) DNA which hybridizes under stringent conditions with DNA complementary to DNA comprising a base sequences according to Seq. No. 1, 3, 5 or 7, and which encodes a protein having adiponectin binding ability.

(4) A recombinant vector containing the gene according to the abovementioned (2) or (3).

(5) A transformant containing the recombinant vector according to the abovementioned (4).

(6) An antibody or a fragment thereof capable of reacting with the protein according to the abovementioned (1).

(7) A screening method for a ligand, agonist or antagonist to an adiponectin receptor, comprising a step of bringing a test substance into contact with the protein according to the abovementioned (1).

(8) A screening kit for a ligand, agonist or antagonist to an adiponectin receptor, comprising the protein according to the abovementioned (1), the DNA according to the abovementioned (2) or (3), and the recombinant vector according to abovementioned (4) or the transformant according to abovementioned (5).

BEST MODE FOR CARRYING OUT THE INVENTION

Figure 1A:
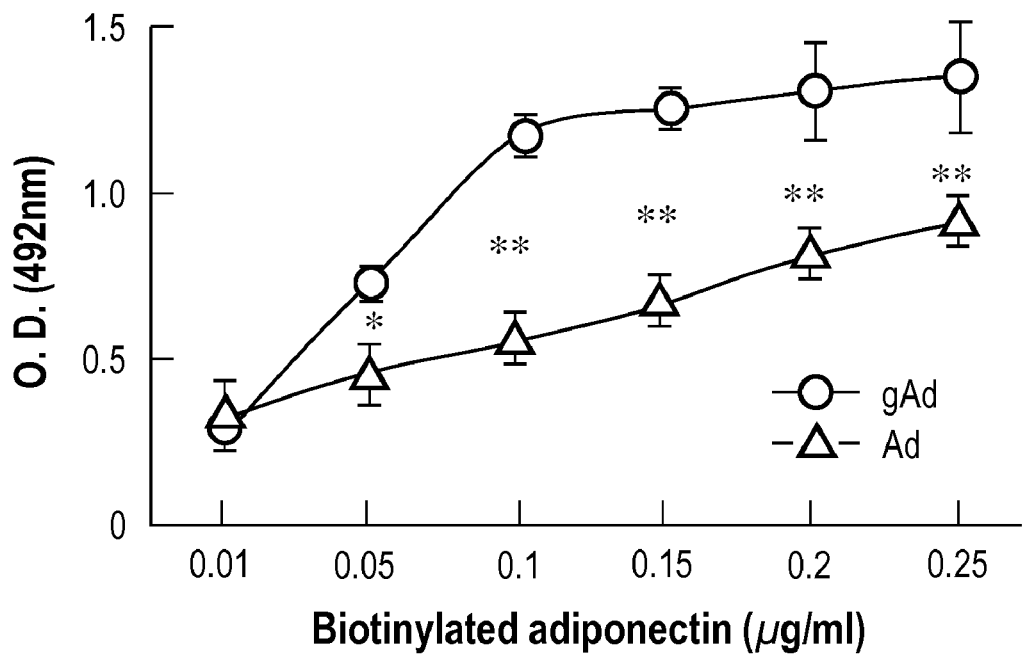
FIG. 1(a) shows the binding of adiponectin to C2C12 myocytes.

A protein of the present invention is a protein as set forth in (a) or (b) below:

(a) a protein comprising an amino acid sequences according to Seq. No. 2, 4, 6 or 8 (hereunder "protein (a)");

(b) a protein comprising an amino acid sequences according to Seq. No. 2, 4, 6 or 8 with one or more amino acids deleted, replaced or added, and having adiponectin binding ability (hereunder "protein (b)").

Protein (a) or (b) has adiponectin binding ability. "Adiponectin binding ability" signifies the ability to bind with adiponectin, and preferably the ability to bind specifically with adiponectin (that is, the adiponectin binding ability of an adiponectin receptor). "Adiponectin binding ability" includes binding ability with respect to either full-length adiponectin or adiponectin consisting only of the globular domain. Proteins having adiponectin binding ability include proteins that can bind only to full-length adiponectin, proteins that can bind only to adiponectin consisting only of the globular domain, proteins that can bind to both full-length adiponectin and adiponectin consisting only of the globular domain, and proteins which bind preferentially to either full-length adiponectin or adiponectin consisting only of the globular domain.

The "globular domain" is the filament-like structural domain at the C end of adiponectin, having a length of a little over 100 amino acids. Complement C1q and the like have domains highly homologous to the globular domain. Functionally, the globular domain of adiponectin acts strongly on skeletal muscle and the like, combusting fatty acids and inhibiting the storage of lipids, and it exhibits the same level of activity as full-length adiponectin at a concentration as low as one-several tenth of that of the full-length adiponectin.

Of proteins (a), those according to Seq. No. 2 or 4 are human adiponectin receptors, while those according to Seq. No. 6 or 8 are mouse adiponectin receptors. The proteins according to Seq. Nos. 2 and 6 are the same kind of adiponectin receptor (AdipoR1), while those according to Seq. Nos. 4 and 8 are a kind of adiponectin receptor (AdipoR2) different from AdipoR1. AdipoR1 is thought to be a receptor with relative selectivity for adiponectin consisting solely of the globular domain rather than full-length adiponectin, while AdipoR2 is thought to be a receptor with relative selectivity for full-length adiponectin rather than adiponectin consisting solely of the globular domain.

The degree of homology between human (Seq. No. 2) and mouse (Seq. No. 6) AdipoR1 at the amino acid level is 96.8%. The degree of homology between human (Seq. No. 4) and mouse (Seq. No. 8) AdipoR2 at the amino acid level is 95.2%. The structures of AdipoR1 and AdipoR2 are similar, and the homology between AdipoR1 (Seq. No. 6) and AdipoR2 (Seq. No. 8) in mice is 66.7%.

In vivo, AdipoR1 is expressed in most tissues, with especially high expression in skeletal muscle, while AdipoR2 is expressed strongly in the liver. AdipoR1 and AdipoR2 are thought to form both homo-and hetero-multimers. Both AdipoR1 and AdipoR2 bind with both full-length adiponectin and adiponectin consisting solely of the globular domain, mediating the stimulating effects of these adiponectins on PPARα (Peroxisome proliferator-activated receptor a) ligand activity and fatty acid oxidation. For example, AdipoR1 is thought to mediate the increases in PPARα ligand activity, fatty acid oxidation and glucose uptake by adiponectin consisting only of the globular domain in myocytes. Similarly, AdipoR2 is thought to partially mediate the increases in PPARα ligand activity and fatty acid oxidation by full-length adiponectin in hepatocytes and myocytes.

AdipoR1 and AdipoR2 Are both thought to contain seven transmembrane domains. In the amino acid sequence according to Seq. No. 2 (human AdipoR1), the amino acid sequences 136-158, 172-194, 207-228, 234-255, 267-289, 299-321 and 336-358 are though to correspond to transmembrane domains. In the amino acid sequence according to Seq. No. 4 (human AdipoR2), the amino acids sequences 60-82, 96-118, 130-152, 158-179, 192-214, 222-244 and 260-282 are though to correspond to transmembrane domains. In the amino acid sequence according to Seq. No. 6 (mouse AdipoR1), the amino acid sequences 136-158, 172-194, 207-228, 234-255, 267-289, 299-321 and 336-358 are though to correspond to transmembrane domains. Finally, in the amino acid sequence according to Seq. No. 8 (mouse AdipoR2), the amino acid sequences 72-94, 108-130, 142-164, 170-191, 204-226, 234-256 and 272-294 are though to correspond to transmembrane domains.

There are no particular limits on the number of amino acids deleted, replaced or added in the amino acid sequences according to Seq. Nos. 2, 4, 6 and 8 as long as adiponectin binding ability is retained. The number may be one or more than one or preferably one or a few, or specifically in the range of normally 1-100 or preferably 1-50 or more preferably 1-10. The amino acid sequences of protein (b) should normally have 60% or more, or preferably 80% or more, or more preferably 90% or more homology with the amino acid sequence of protein (a).

There are no particular limits on the locations of the amino acids deleted, replaced or added in the amino acid sequences according to Seq. No. 2, 4, 6 or 8, as long as adiponectin binding ability is retained.

Protein (b) includes proteins wherein deletions, replacements, additions and other mutations have been artificially introduced into a protein (a), as well as proteins naturally occurring with introduced deletions, replacements, additions and other mutations and such proteins with deletions, replacements, additions and other mutations artificially introduced. Examples of proteins naturally occurring with introduced deletions, replacements, additions and other mutations include proteins derived from humans and other mammals such as monkeys, cows, sheep, goats, horses, pigs, rabbits, dogs, cats, mice, rats and the like (including proteins which may occur due to polymorphisms in such mammals).

Proteins (a) and (b) include both proteins with added sugar chains and proteins without added sugar chains. The types, locations and the like of the sugar chains added to the proteins will differ depending on the type of host cells used in manufacturing the protein, but proteins with added sugar chains include proteins obtained using any kind of host cells. Proteins (a) and (b) also include pharmacologically allowable salts thereof.

A gene encoding protein (a) or (b) can be obtained for example by using mRNA extracted from the skeletal muscle, livers, hearts, macrophages, blood vessels, brains, kidneys, lungs, placentas, spleens, testes, peripheral blood, thymus glands, intestines or other tissues of humans, mice or other mammals to build a cDNA library, and then using probes synthesized based on the base sequences according to Seq. No. 1, 3, 5 or 7 to screen the cDNA library for clones containing the target DNA. The steps involved in preparing a cDNA library and screening for clones containing the target DNA are explained below.

[Preparing a cDNA Library]

To prepare a cDNA library, total RNA is first obtained from the skeletal muscle, livers, hearts, macrophages, blood vessels, brains, kidneys, lungs, placentas, spleens, testes, peripheral blood, thymus glands, intestines or other tissues of humans, mice or other mammals for example, and poly(A+) RNA (mRNA) is then obtained by the batch method, affinity column method or the like using oligo(dT)-cellulose, poly (U)-sepharose or the like. The poly(A+) RNA (mRNA) in this case may also be fractionated by sucrose density gradient centrifugation or the like. Taking the resulting mRNA as the template, single-stranded cDNA is then synthesized using oligo(dT) primer and reverse transcriptase, and double-stranded cDNA is synthesized from the single-stranded cDNA. The resulting double-stranded cDNA is incorporated into a suitable cloning vector to prepare a recombinant vector which is used to transform E. coli or other host cells, and a cDNA library is obtained by selection of transformants using tetracycline resistance or ampicillin resistance as the indicator. The cloning vector for preparing the cDNA library may be any vector that can replicate independently in the host cells, and for example phage vectors, plasmid vectors and the like can be used. E. coli or the like can be used as the host cells.

Transformation of the E. coli or other host cells can be accomplished by a method such as adding the recombinant vector to competent cells prepared with calcium chloride, magnesium chloride or rubidium chloride. When a plasmid is used as the vector, a resistance gene for a drug such as tetracycline or ampicillin is included.

A commercial kit such as the SuperScript Plasmid System for cDNA Synthesis and Plasmid Cloning (Gibco BRL) or the ZAP-cDNA Synthesis Kit (Stratagene) can be used in preparing the cDNA library.

[Screening for Clones Containing the Target DNA]

To screen the cDNA library for clones containing the target DNA, primer is synthesized based on the base sequence according to Seq. No. 1, 3, 5 or 7, and used in a polymerase chain reaction (PCR) to obtain PCR amplified fragments. The PCR amplified fragments may also be sub-cloned using a suitable plasmid vector. There are no particular limits on the primer set used in PCR, which can be designed based on the base sequence according to Seq. Nos. 1, 3, 5 or 7.

The target DNA is obtained by colony hybridization or plaque hybridization of the cDNA library, with the PCR amplified fragments as the probe. The PCR amplified fragments may be labeled with an isotope (such as $^{32}$P or $^{35}$S), biotin, digoxigenin, alkaliphosphotase or the like for use as the probe. Clones containing the target DNA are obtained by an expression screening method such as immunoscreening using antibodies.

The resulting DNA can be incorporated into a vector by ordinary methods, either as the original DNA fragments or after cleavage with a suitable restriction enzyme or the like, and the base sequence can be determined by an ordinarily used method of base sequence analysis, such as the Maxam-Gilbert chemical modification method or the dideoxynucleotide chain termination method. A base sequence analyzing device such as the 373A DNA Sequencer (Perkin Elmer) is normally used in analyzing the base sequence.

A gene encoding protein (a) or (b) comprises an open reading frame encoding protein (a) or (b) and the termination codon located at the 3' end thereof. Moreover, a gene encoding protein (a) or (b) can comprise an untranslated region (UTR) at the 5' and/or 3' ends of the open reading frame.

Examples of the gene encoding protein (a) include a gene comprising DNA comprising a base sequence according to Seq. No. 1, 3, 5 or 7. Of the base sequence according to Seq. No. 1, bases 1-1125 constitute the open reading frame which encodes the protein according to Seq. No. 2, while the translation initiation codon is located at bases 1-3 of the base sequence according to Seq. No. 1, and the termination codon at bases 1126-1128 of the sequence. Of the base sequence according to Seq. No. 3, bases 1-897 constitute the open reading frame which encodes the protein according to Seq. No. 4, while the translation initiation codon is located at bases 1-3 of the base sequence according to Seq. No. 3, and the termination codon at bases 898-900. Of the base sequence according to Seq. No. 5, bases 1-1125 constitute the open reading frame which encodes the protein according to Seq. No. 6, while the translation initiation codon is located at bases 1-3 of the base sequence according to Seq. No. 5, and the termination codon at bases 1126-1128. Of the base sequence according to Seq. No. 7, bases 1-933 constitute the open reading frame which encodes the protein according to Seq. No. 8, while the translation initiation codon is located at bases 1-3 of the base sequence according to Seq. No. 7, and the termination codon at bases 934-936.

There are no particular limits on the base sequence of the gene encoding protein (a) so long as it encodes protein (a), and the base sequence of the open reading frame is not restricted to a base sequence according to Seq. No. 1, 3, 5 or 7. The gene encoding protein (a) can also be obtained by chemical synthesis according to its base sequence. Chemical synthesis of DNA can be accomplished using a commercial DNA synthesizer, such as a DNA synthesizer using the thiophosphite method (Shimadzu Corporation) or the phosphoramidite method (Perkin Elmer).

An example of a gene encoding protein (b) is a gene comprising DNA which hybridizes under stringent conditions with DNA complementary to DNA comprising a base sequence according to Seq. No 1, 3, 5 or 7, and which encodes a protein having adiponectin binding ability.

An example of "stringent conditions" would be for example 42° C., 2×SSC and 0.1% SDS, or preferably 65° C., 0.1×SSC and 0.1% SDS.

A specific example of DNA which hybridizes under stringent conditions with DNA complementary to DNA comprising a base sequence according to Seq. No. 1, 3, 5 or 7 is DNA having 60% or more or preferably 80% or more or more preferably 90% or more homology with a base sequence according to Seq. No. 1, 3, 5 or 7.

The gne encoding protein (b) can be obtained for example by artificially introducing mutations into DNA comprising a base sequence according to Seq. No. 1, 3, 5 or 7, using a well-known method such as site-directed mutagenesis. Mutations can be introduced using a mutagenesis kit, such as a Mutant-K (Takara), Mutant-G (Takara) or Takara LA PCR in vitro Mutagenesis series kit. DNA whose base sequence has already been determined can be obtained by chemical synthesis.

Protein (a) or (b) can be manufactured according to the following steps by expressing the gene encoding each protein in host cells.

[Preparation of Recombinant Vectors and Transformants]

To prepare a recombinant vector, a DNA fragment of a suitable length is prepared which comprises a region encoding the target protein. The DNA is also prepared wherein bases of the base sequence of the protein-encoding region are replaced so that the codons are optimized for expression in the host cells.

A recombinant vector is prepared by inserting this DNA fragment downstream from the promoter of a suitable expression vector, and a transformant capable of producing the target protein is obtained by introducing the recombinant vector into suitable host cells. The DNA fragment needs to be incorporated into the vector so that its functions are expressed, and the vector may contain in addition to the promoter enhancers or other cis-elements, splicing signals, poly(A) addition signals, selection markers (such as dihydrofolate reductase gene, ampicillin resistance gene or neomycin resistance gene), ribosome binding sequences (SD sequences) or the like.

There are no particular limits on the expression vector as long as it can replicate independently in the host cells, and for example plasmid vectors, phage vectors, virus vectors and the like can be used. Examples of plasmid vectors include *E. coli*-derived plasmids (such as pRSET, pBR322, pBR325, pUC118, pUC119, pUC18 and pUC19), *Bacillus subtilis*-derived plasmids (such as pUB110 and pTP5) and yeast-derived plasmids (such as YEp13, YEp24 and Ycp50).

Examples of phage vectors include α-phages (such as Charon4A, Charon21A, EMBL3, EMBL4, λgt10, λgt11 and λZAP), and examples of virus vectors include retroviruses, vaccinia virus and other animal viruses and baculoviruses and other insect viruses.

As long as the host cells can express the target DNA, they can be prokaryotic cells, yeasts, animal cells, insects cells, plant cells or the like. An animal body, plant body, silkworm body or the like can also be used.

When bacteria are used as the host cells, they can be for example *Escherichia coli* or other *Escherichia*, *Bacillus subtilis* or other *Bacillus*, *Pseudomonas putida* or other *Pseudomonas*, or *Rhizobium meliloti* or other *Rhizobium* bacteria. Specifically, *Escherichia coli* XL1-Blue, *Escherichia coli* XL2-Blue, *Escherichia coli* DH1, *Escherichia coli* K12, *Escherichia coli* JM109, *Escherichia coli* HB101 and other *Escherichia coli* and *Bacillus subtilis* MI 114, *Bacillus subtilis* 207-21 and other *Bacillus subtilis* can be used as the host cells. There are no particular limits on the promoter in this case as long as it is capable of expression in *E. coli* or other bacteria, and for example a trp promoter, lac promoter, $P_L$ promoter, $P_R$ promoter or other *E. coli* or phage-derived promoter can be used. Artificially designed and altered promoters such as tac promoter, lacT7 promoter or let I promoter may also be used.

There are no particular limits on the method of introducing the recombinant vector into the bacteria as long as the method can introduce DNA into bacteria, and electroporation or a method employing calcium ions may be used for example.

When a yeast is used for the host cells, *Saccharomyces cerevisiae*, *Schizosaccharomyces pombe*, *Pichia pastoris* or the like may be used. There are no particular limits on the promoter in this case as long as it is capable of expression in yeasts, and for example a gall promoter, gal10 promoter, heat shock protein promoter, MFα1 promoter, PH05 promoter, PGK promoter, GAP promoter, ADH promoter, AOX1 promoter or the like can be used.

There are no particular limits on the method of introducing the recombinant vector into the yeast as long as the method can introduce DNA into yeast, and the electroporation, spheroplast or lithium acetate method or the like may be used.

When the host cells are animals cells, monkey COS-7 cells, Vero, chinese hamster ovary cells (CHO cells), mouse L cells, rat GH3, human FL cells or the like may be used as the host cells. There are no particular limits on the promoter in this case as long as it is capable of expression in animal cells, and for example an SRα promoter, SV40 promoter, LTR (Long Terminal Repeat) promoter, CMV promoter or human cytomegalovirus early gene promoter or the like can be used.

There are no particular limits on the method of introducing the recombinant vector into the animal cells as long as the method can introduce DNA into animal cells, and the electroporation, calcium phosphate or lipofection method or the like can be used.

When the host cells are insect cells, *Spodoptera frugiperda* ovarian cells, *Trichoplusia ni* ovarian cells, cultured cells from silkworm ovaries and the like may be used as the host cells. Possible *Spodoptera frugiperda* ovarian cells include Sf9 and Sf21 cells and the like, *Trichoplusia ni* ovarian cells include High 5 and BTI-TN-5B1-4 (Invitrogen) and the like, and cultured cells derived from silkworm ovaries include *Bombyx mori* N4 cells and the like.

There are no particular limits on the method of introducing the recombinant vector into the insect cells as long as the method can introduce DNA into insect cells, and the calcium phosphate, lipofection or electroporation method or the like can be used.

[Culturing the Transformant]

A transformant into which a recombinant vector with incorporated DNA encoding the target protein has been introduced can be cultured by ordinary culture methods. Culturing of the transformant can be accomplished by ordinary methods used in the culture of host cells.

The medium for culturing a transformant obtained as bacteria, yeasts or other microbial host cells contains carbon sources, nitrogen sources, inorganic salts and the like which can be used by those microorganisms, and either a natural or synthetic medium may be used as long as it is a medium for efficient culturing of the transformant.

Glucose, fructose, sucrose, starch and other carbohydrates, acetic acid, propionic acid and other organic acids, and ethanol, propanol and other alcohols can be used as carbon sources. Ammonia, ammonium chloride, ammonium sulfate, ammonium acetate, ammonium phosphate and other ammonium salts of inorganic and organic acids as well as peptone, meat extract, yeast extract, corn steep liquor, casein hydrolysate and the like can be used as nitrogen sources. Monopotassium phosphate, dipotassium phosphate, magnesium phosphate, magnesium sulfate, sodium chloride, ferrous sulfate, manganese sulfate, copper sulfate, calcium carbonate and the like can be used as inorganic salts.

Culturing of a transformant obtained as *E. coli*, yeast or other microbial host cells is accomplished under aerobic conditions such as a shaking culture or aerated spinner culture. The culture temperature is normally 25-37° C., the culture time is normally 12-48 hours, and a pH of 6-8 is maintained during the culture period. The pH can be adjusted using an inorganic acid, organic acid or alkaline solution or urea, calcium carbonate, ammonia or the like. An antibiotic such as ampicillin or tetracycline can be added to the medium as necessary during culture.

When culturing microorganisms transformed with an expression vector employing an inducible promoter as the promoter, an inducer can be added to the medium as necessary. For example, isopropyl-β-D-thiogalactopyranoside or the like can be added to the medium when culturing a microorganism transformed with an expression vector employing a lac promoter, while indoleacrylic acid or the like can be added when culturing a microorganism transformed with an expression vector employing a trp promoter.

Commonly used RPMI1640 medium, Eagle MEM medium, DMEM medium, Ham F12 medium, Ham F12K medium and such medium with fetal calf serum added can be used as the medium for culturing a transformant obtained with animal cells as the host cells. The transformant is normally cultured for 3-10 days at 37° C. under the presence of 5% $CO_2$. For purposes of culture, an antibiotic such as kanamycin, penicillin, streptomycin or the like can be added to the medium as necessary.

Commonly used TNM-FH medium (Pharmingen), Sf-900 II SFM medium (Gibco BRL), ExCell400 or ExCell405 (JRH Biosciences) or the like can be used as the medium for culturing a transformant obtained with insect cells as the host cells. The transformant is normally cultured for 3-10 days at 27° C. For purposes of culture, an antibiotic such as gentamicin can be added to the medium as necessary.

The target protein can also be expressed as an excreted protein or a fused protein. Examples of proteins to be fused include β-galactosidase, protein A, protein A IgG binding region, chloramphenicol acetyltransferase, poly(Arg), poly(Glu), protein G, maltose binding protein, glutathione S transferase, polyhistidine chain (His-tag), S peptide, DNA binding protein domain, Tac antigen, thioredoxin, and green fluorescent protein.

[Protein Isolation and Purification]

The target protein is obtained by harvesting the target protein from the transformant culture. "Culture" in this case includes culture supernatant, cultured cells, cultured bacterial bodies, or crushed cells or bacterial cell bodies.

When the target protein is accumulated in the transformant cells, the cells in the culture are collected by centrifugation of the culture, and the cells are then washed and crushed and the target protein extracted. If the target protein is excreted outside the transformant cells, the culture supernatant is used as is, or else cells or bacterial cell bodies are removed from the culture supernatant by centrifugation or the like.

The resulting protein (a) or (b) can then be purified by a method such as solvent extraction, salting-out desalting with ammonium sulfate or the like, precipitation with organic solvents, diethylaminoethyl (DEAE)-sepharose, ion exchange chromatography, hydrophobic chromatography, gel filtration, affinity chromatography or the like.

Protein (a) or (b) can also be manufactured based on its amino acid sequence by a chemical synthesis method such as the Fmoc (fluorenylmethyloxycarbonyl) or tBoc (t-butyloxycarbonyl) method. A commercial peptide synthesizer can be used in this case.

The antibodies or fragments thereof of the present invention are antibodies or fragments thereof which react to protein (a) or (b). As used here, "antibodies" include both monoclonal and polyclonal antibodies, and "monoclonal and polyclonal antibodies" include all classes of monoclonal and polyclonal antibodies. "Antibodies" also include antiserum obtained by immunizing rabbits, mice or other immune animals with protein (a) or (b), as well as human antibodies and humanized antibodies obtained by genetic recombination. "Antibody fragments" include Fab fragments, F(ab)'$_2$ fragments, single-chain antibodies (scFv) and the like.

The antibodies or fragments thereof of the present invention are prepared using protein (a) or (b) as the immunizing antigen. For example, (i) crushed or crushed and purified cells or tissue expressing protein (a) or (b), (ii) recombinant protein expressed by introduction of DNA encoding protein (a) or (b) into *E. coli*, insect cells, animal cells or another host by genetic recombination, or (iii) chemically synthesized peptides or the like can be used as the immunizing antigen.

To prepare polyclonal antibodies, rats, mice, guinea pigs, rabbits, sheep, horses, cows or other mammals are immunized with the immunizing antigen. It is preferable to use mice as the immune animals because the antibody can be easily prepared. For immunization, it is preferable from the standpoint of inducing antibody production to use Freund's complete adjuvant or another auxiliary to prepare an emulsion which is then administered multiple times. In addition to Freund's complete adjuvant (FCA), Freund's incomplete adjuvant (FIA), ammonium hydroxide gel and the like can be used as auxiliaries. The antigen dosage per individual mammal can be determined based on the kind of mammal, but in the case of mice it is ordinarily 50-500 μg. Administration may be intravenous, subcutaneous, intraperitoneal or the like. Immunization is normally performed at intervals of between several days and several weeks, preferably at intervals of 4 days to 3 weeks for a total of 2-8 or preferably 2-5 immunizations. 3-10 days after the last immunization, antibody titer for protein (a) or (b) is measured, and after antibody titer rises blood is taken and antiserum obtained. Antibody titer can be measured by enzyme-linked immunosorbent assay (ELISA), radio-immuno-assay (RIA) or the like.

When antibodies need to be purified from the antiserum, a well known method such as salting out with ammonium sulfate, gel chromatography, ion exchange chromatography, affinity chromatography or the like or a combination of such methods can be selected as appropriate.

To prepare monoclonal antibodies, mammals are immunized using immune antigen as in the case of polyclonal antibodies, and antibody-producing cells are harvested 2-5 days after the final immunization. Examples of antibody-producing cells include spleen cells, lymph node cells, thymus cells, peripheral blood cells and the like, but spleen cells are normally used.

Next, cell fusion of the antibody-producing cells with myeloma cells is performed to obtain a hybridoma. Commonly available cells strains derived from humans, mice or other mammals can be used as the myeloma cells for fusion with the antibody-producing cells. It is preferable that the cell strain used be one that has drug selectivity and that does not survive in unfused form in selection medium (such as HAT medium), but which only survives when fused with the antibody-producing cells. Specific examples of myeloma cells include P3×63-Ag.8.U1 (P3U1), P3/NSI/1-Ag4-1, Sp2/0-Ag14 and other mouse myeloma cell strains.

Cell fusion is performed by mixing specific proportions (such as between 1:1 and 1:10) of the antibody-producing cells and myeloma cells in an animal cell culture medium such as DMEM or RPMI-1640 which contains no serum, and then performing a fusion reaction with polyethylene glycol or another cell fusion accelerator or by electrical pulse treatment (such as electroporation).

Following cell fusion treatment, culture is performed in a selection medium, and the target hybridoma selected. Next, the culture supernatant of the multiplied hybridoma is screened to confirm the presence of the target antibodies. Hybridoma screening may be according to ordinary methods without any particular limitations. For example, part of the culture supernatant in a well containing a hybridoma can be harvested and screened by enzyme-linked immunosorbent assay (ELISA), radio-immuno-assay (RIA) or the like.

The hybridoma can be cloned by limiting dilution analysis, soft agar cloning, fibrin gel cloning, fluorescence activated cell sorting and the like, to finally obtain a hybridoma which produces monoclonal antibodies.

Harvesting of monoclonal antibodies from the resulting hybridoma can be accomplished by an ordinary cell culture method or the like. In the cell culture method, the hybridoma is cultured for example for 3-10 days under ordinary culture conditions (such as 37° C., 5% $CO_2$) in an animal cell culture medium such as MEM medium or RPMI-1640 medium containing 10-20% fetal calf serum, and monoclonal antibodies are obtained from the culture supernatant. The hybridoma can also be transplanted intraperitoneally to mice or the like, ascites collected after 10-14 days, and monoclonal antibodies obtained from the ascites.

When monoclonal antibodies need to be purified, a well-known method such as salting out with ammonium sulfate, gel chromatography, ion exchange chromatography, affinity chromatography or the like or a combination of such methods can be selected as appropriate.

When monoclonal antibodies are intended for administration to human beings (antibody therapy), human antibodies or humanized antibodies should be used to reduce immunogenicity. Human antibodies or humanized antibodies are obtained for example by preparing a hybridoma using as the immune animals mice or the like having introduced human antibody DNA, or by using a library having the antibodies presented on a phage. Specifically, a transgenic animal having a repertory of human antibody DNA is immunized with the antigen as a protein or protein-expressing cells or solution thereof to obtain antibody-producing cells, which are then fused with myeloma cells to produce a hybridoma which is used to obtain human antibodies to the target protein (see International Publication Nos. WO92-03918, WO93-2227, WO94-02602, WO96-33735 and WO96-34096). Alternatively, scFv which binds to the target protein can be selected by sorting out, from an antibody library having multiple different human scFv presented on phages, those phages presenting antibodies which bind to the antigen as a protein or protein-expressing cells or solution thereof (Griffiths et al, *EMBO J.* 12, 725-734, 1993).

The screening method of the present invention comprises a step of bringing a test substance into contact with protein (a) or (b). In the screening method of the present invention, a ligand, agonist or antagonist to an adiponectin receptor can be screened by bringing a test substance into contact with protein (a) or (b) and determining whether the test substance binds to protein (a) or (b). The screened substances should also be subjected to another step to determined whether or not they actually act as a ligand, agonist or antagonist to an adiponectin receptor.

There are no particular limits on the types of test substances, but examples include high molecular compounds, low molecular compounds, cell cultures, tissue extracts and the like.

For screening purposes, (i) cells or tissues or processed cells or tissues expressing protein (a) or (b), (ii) recombinant proteins expressed by introduction of DNA encoding protein (a) or (b) into *E. coli*, yeast, insect cells, animal cells or another host by recombinant technology, or (iii) chemically synthesized peptides for example can be used as protein (a) or (b). The cells or tissues expressing protein (a) or (b) may be either cells or tissues (such as muscle cells, skeletal muscles, hearts, macrophages, blood vessels, brains, kidneys, lungs, placentas, spleens, testes, peripheral blood, thymus glands, intestines or the like) which express protein (a) or (b) as an endogenous protein, or cells or tissues which express protein (a) or (b) as an exogenous protein (such as *E. coli*, yeast, insect cells, animal cells or the like having introduced DNA encoding protein (a) or (b)). Processed cells or tissues are cells are tissues which have been crushed, extracted, purified or the like, and include for example cell membrane fractions of cells or tisues.

Whether or not the test substance acts as a ligand, agonist or antagonist to the adiponectin receptor can be determined for example based on the amount of binding of the test substance to protein (a) or (b) or according to the presence or degree of cell response due to binding of the test substance to protein (a) or (b).

The amount of binding of the test substance to protein (a) or (b) can be measured for example using a labeled test substance, labeled antibodies to the test substance or the like. Radioactive isotope elements such as $^3H$, $^{14}C$, $^{125}I$, $^{35}S$, and $^{32}P$ and fluorescent dyes and the like can be used as labels. The radioactivity of the radioactive isotope element can be measured using a liquid scintillation counter, X-ray film, imaging plate or the like, while the fluorescent strength of the fluorescent dye can be measured for example by a CCD camera, fluorescent scanner, spectrofluorometer or the like.

Examples of cell responses due to binding of the test substance to protein (a) or (b) include stimulation or suppression of PPARα ligand activity, stimulation or suppression of fatty acid oxidation, stimulation or suppression of glucose uptake, increased or decreased intracellular pH, increased or decreased AMP kinase activity, increased or decreased AMP kinase phosphorylation, increased or decreased p38 MAP kinase activity, increased or decreased p38 MAP kinase phosphorylation, stimulation or suppression of gluconeogenesis, and increased or decreased uncoupled protein and the like.

In measuring the amount of binding of the test substance to protein (a) or (b) and the presence or degree of cell response, it is desirable to compare measurement values with and without protein (a) or (b).

Lipid cells secrete adiponectin as a vital insulin sensitizing hormone, and lipid cell hypertrophy leads to decreased adiponectin excretion, which leads to insulin resistance, which in turn is a cause of diabetes, hyperlipidemia and hypertension. Decreased adiponectin excretion also promotes arteriosclerosis. Consequently, substances which have been screened as an agonist or antagonist to an adiponectin receptor can be used for example as insulin resistance improving drugs, diabetes preventive and therapeutic drugs, hyperlipidemia preventive and therapeutic drugs, hypertension preventive and therapeutic drugs, arteriosclerosis preventive and therapeutic drugs, obesity preventive and therapeutic drugs, anti-inflammatory drugs, osteoporosis preventive and therapeutic drugs, anti-cancer drugs and the like.

These drugs may be composed solely of the screened substances, but normally they are prepared using pharmaceutically acceptable excipients and other additives as desired. For purposes of preparation, excipients, binders, disintegrators, lubricants, stabilizers, flavorings and perfumes, diluents, solvents for injection and other additives can be used for example. Administration may be oral or parenteral (subcutaneous, intramuscular, intraperitoneal or the like) for example, and forms of administration include sprays, capsules, pills, granules, syrups, emulsions, suppositories, injections, suspensions and the like. The dosage and number of administrations will differ according to the desired effects, administration method, treatment period, and age, weight, sex and the like of the patient, and can be adjusted appropriately according to the type of screened substance.

Protein (a) or (b), a gene encoding protein (a) or (b), a recombinant vector containing the DNA and a transformant containing the recombinant vector can be used as constituent elements in a screening kit for a ligand, agonist and antagonist to an adiponectin receptor. They are included in the screening kit as suppliers of protein (a) or (b).

The screening kit can take any form as long as it includes protein (a) or (b), a gene encoding protein (a) or (b), a recombinant vector containing the DNA or a transformant containing the recombinant vector, and can include various reagents (buffers and the like), measurement equipment, labeling compounds, model animals, cell strains, cell culture media and the like.

EXAMPLES

In the following text and figures relating to the examples, adiponectin may be referred to as "Adipo," adiponectin consisting solely of the globular domain as "globular Adipo" or "gAd," and full-length adiponectin as "full-length Adipo" or "Ad." An adiponectin receptor may be referred to as "AdipoR," a human adiponectin receptor as "hAdipoR," and a mouse adiponectin receptor as "mAdipoR". "AdipoR1" and "AdipoR2" are designations for adiponectin receptors comprising different amino acid sequences.

1. Experimental Methods (1) Retrovirus Production and Infection

For production of retroviral supernatants, $10^7$ Plat-E packaging cells (Morita, S. et al, Gene Ther. 7, 1063-1066 (2000)) were transiently transfected with 10 μg of human skeletal muscle cDNA library (Clontech) using Lipofectamine PLUS (Life Technologies). After 24 hours of incubation the supernatants (10 mL) was harvested. Ba/F3 cells were infected with 1/20-diluted supernatants supplemented with 10 μg/mL polybrene (hexadimethrine bromide, Sigma) corresponding to an estimated m.o.i. of 0.3. Six hours later, the medium was changed, and the Ba/F3 cells were expanded by culturing for 6 days prior to freezing or selection.

(2) FACS Analysis and cDNA Sequencing

FACS analysis was performed according to the method of Stoecklin et al (Stoecklin, G. et al, EMBO J. 21, 4709-4718 (2000)). For selection, cells were enriched with FACVantage (Becton Dickinson) from $1\times10^7$ Ba/F3 cells transfected with human skeletal muscle cDNA library. The cells were recovered, expanded, and subjected to FACS analysis 11 days later. The selected cells were further expanded and subjected to FACS analysis. In order to sequence the cDNA incorporated into the selected cells, PCR was performed with upstream and downstream primers for the retrovirus vector, using 50 ng of genome DNA extracted from the selected cells as the template, and the resulting PCR amplified fragments were sequenced.

PCR was performed in 35 cycles of 1 minute at 94° C., 2 minutes at 56° C. and 3 minutes at 72° C., using Taq polymerase (Perkin-Elmer/Cetus). The primers (pLIB primers) for the retrovirus vector were as follows:

```
5' primer:    5'-agccctcactccttctctag-3'

3' primer:    5'-acctacaggtggggtctttcattccc-3'
```

After removal of the primer, the base sequence of the PCR product was determined by direct sequencing using a BigDye Terminator Kit (Applied Biosystems).

(3) Northern Blot Analysis

Human multiple tissues Northern blot filters I and II (brain, heart, skeletal muscle, colon, thymus, spleen, kidney, liver, small intestine, placenta, lung, peripheral blood leukocytes) were purchased from Clonetech. These filters were hybridized with [$^{32}$P] dCTP-labeled cDNA probes (the PstI/BstXI, BamHI/PstI and EcoRV/NotI fragment of human AdipoR1 cDNA, mouse AdipoR1 cDNA, and human and mouse AdipoR2 cDNA, respectively) in a hybridization buffer containing 4×SSC, 5×Denhardt's solution, 0.2% SDS, 200 mg/mL salmon sperm DNA and 50% formamide at 42° C. for 24 hours. The filters were washed in 0.1×SSC, 0.1% SDS at 65° C., and then subjected to autoradiography. The same northern blot analysis was performed on various mouse tissues (brain, heart, kidney, liver, lung, skeletal muscle, spleen, testis).

(4) Expression of Proteins in Mammalian Cells, and Characterization

The AdipoR1 or R2 expression vector was constructed by ligating AdipoR1 or AdipoR2 cDNA into the EcoRV/NotI site of pCXN2 (Kinoshita, S. et al, Pharm Res. 15, 1851-1856 (1998)). HEK-293T (human embryonic kidney cells), HAEC (normal human aortic endothelial cells) and C2C12 myocytes (mouse myocyte strain) were cultured in DMEM. 10% fetal calf serum (FCS) was contained in the medium. DNA transfection was performed by lipofection using Lipofectamine PLUS (Gibco BRL) for all cells.

(5) RNA Interference in C2C12 Myocytes

According to the method of Karpichev et al (Karpichev, I. V., J. Biol. Chem. 277, 19609-19617 (2002)), two pairs of siRNA were chemically synthesized, annealed, and transfected into C2C12 myocytes which had been differentiated into myotube cells by 4-7 days culture in DMEM containing horse serum after 2 days from confluence. siRNA was also transfected into hepatocytes and HAEC in the same way. 48 hours after transfection of siRNA, the cells were lysed.

The base sequences of the unrelated control siRNA (siRNA) are as follows:

```
Unrelated-sense:        gugcgcugcuggugccaaccctt

Unrelated-antisense:    ggguuggcaccagcagcgcactt
```

The base sequences of siRNA (siRNA mAdipoR1) corresponding to the coding region of the mouse AdipoR1 gene are as follows:

```
siRNA mAdipoR1-sense:      gagacuggcaacaucuggacatt siRNA mAdipoR1-antisense:  uguccagauguugccagucuctt
```

The base sequences of siRNA (siRNA mAdipoR2) corresponding to the coding region of the mouse AdipoR2 gene are as follows:

```
siRNA mAdipoR2-sense:      gcuuagagacaccuguuuguutt siRNA mAdipoR2-antisense:  aacaaacaggugucucuaagctt
```

The base sequences of siRNA (siRNA hAdipoR1) corresponding to the coding regions of the human AdipoR1 gene are as follows:

```
siRNA hAdipoR1-sense:      ggacaacgacuaucugcuacatt siRNA hAdipoR1-antisense:  uguagcagauagucguugucctt
```

The base sequences of siRNA (siRNA hAdipoR2) corresponding to the coding regions of the human AdipoR2 gene are as follows:

```
siRNA hAdipoR2-sense:      ggaguuucguuucaugaucggtt siRNA hAdipoR2-antisense:  ccgaucaugaaacgaaacucctt
```

(6) Measurement of PPARα (Peroxisome Proliferator-Activated Receptor α) Ligand Activity Mouse globular Adipo and full-length Adipo expressed using E. coli were purified according to the method of Yamauchi et al (Yamauchi, T. et al, Nat. Med. 8, 1288-1295 (2002)). According to the method of Yamauchi et al al (Yamauchi, T. et al, Nat. Med. 8, 1288-1295 (2002)), the differentiated C2C12 myocytes or isolated hepatocytes were treated with a fixed concentration of adiponectin. PPARα ligand activity was quantitatively determined according to the method of Yamauchi et al (Yamauchi, T. et al, J. Biol. Chem. 278, 2461-2468 (2002)) using a (UAS) X 4-tk-LUC reporter plasmid, a GAL4-rat PPARα ligand binding domain expressing plasmid and a β-galactosidase expressing plasmid (internal control).

(7) Lipid and Glucose Metabolism

[$^{14}$C] $CO_2$ production from [$^{1-14}$C] palmitic acid was measured using cell lysate according to the method of Yamauchi et al (Yamauchi, T. et al, *Nat. Med.* 7, 941-946 (2001)). Glucose uptake was also measured according to the method of Yamauchi et al (Yamauchi, T. et al, *Nat. Med.* 8, 1288-1295 (2002)).

(8) Study Using Dominant Negative Amp Kinase (AMPK)

cDNA encoding α2 AMPK (including a mutation that alters lysine residue #45 to arginine residue) was used as DN-α2 AMPK (Yamauchi, T. et al, *Nat. Med.* 8, 1288-1295 (2002)). C2C12 myocytes were infected with equal titers of adenovirus containing a control MOCK vector or DN-α2 AMPK. According to the method of Yamauchi et al (Yamauchi, T. et al, *Nat. Med.* 8, 1288-1295 (2002)), 5 days after induction of differentiation, the cells were treated with a fixed concentration of Adipo, and PPARα ligand activity and fatty acid oxidation were measured.

(9) Binding Assay

Synthetic human or mouse Adipo was $^{125}$I-labeled at Tyr with IODO-beads (Pierce) in the presence of Na$^{125}$I (2000 Ci/mmol, Amersham Pharmacia Biotech). Recombinant globular Adipo or full-length Adipo was biotinylated with NHS-LC-Biotin (Pierce). The cells were seeded on 96-well plates at a density of $4.1 \times 10^4$/well. After an overnight culture, the medium was discarded and the cells were incubated overnight at 37° C. with a binding assay buffer (HEPES buffered saline/0.1% bovine serum albumin) containing fixed concentrations of [$^{125}$I] Adipo and unlabeled competitors. According to the methods of Yamauchi et al (Yamauchi, T. et al, *Nat. Med.* 8, 1288-1295 (2002)); Yokomizo, T. et al. *Nature* 387, 620-624 (1997)), the cells were then washed three times with ice-cold phosphate-buffered saline and lysed in 0.1N NaOH/0.1% SDS, and the cell-bound radioactivity was determined using a α-counter.

(10) Fluorescent Microscopic Analysis

The cellular location of AdipoR1 or AdipoR2 was evaluated by confocal fluorescence microscopy using 293T cells. The cells were fixed in 1% paraformaldehyde, with or without permeabilization using 5× diluted permeabilization buffer (Coulter), and the cells were incubated for 1 hour at 22° C., with anti-FLAG antibody (M2; 30 μg/mL). Then they were incubated with 10 μg/mL of secondary antibody conjugated to AlexFluor 488. Confocal imaging was then performed with a laser-scanning microscopy system configured with a Nikon microscope and a Krypton/argon laser (488 nm).

(11) Quantitative Analysis of AdipoR1 and AdipoR2 Gene Transcripts by Real-Time PCR Quantitative analysis of four transcripts corresponding to the human AdipoR1, human AdipoR2, mouse AdipoR1 and mouse AdipoR2 genes was performed by real-time PCR according to the method of Heid et al (Heid, C. A. et al, *Genome Res.* 6, 986-994 (1996)). The primer sets and the probes for the transcripts were as follows. The PCR product was measured continuously using an ABI PRISM7700 Sequence Detection System (Applied Biosystems). The relative amounts of each transcript were normalized to the amount of actin transcript.

```
[Mouse AdipoR1 gene]
Forward primer:  5'-acgttggagagtcatcccgtat-3'
Reverse primer:  5'-ctctgtgtggatgcggaagat-3'
Probe:           5'-cctgctacatggccacagaccaccgt-3'
                 (with minor groove binder)

[Mouse AdipoR2 gene]
Forward primer:  5'-tcccaggaagatgaagggtttat-3'
Reverse primer:  5'-ttccattcgttcgatagcatga-3'
Probe:           5'-atgtccccgctcctacaggccc-3'
                 (with minor groove binder)

[Human AdipoR1 gene]
Forward primer:  5'-ttcttcctcatggctgtgatgt-3'
Reverse primer:  5'-aagaagcgctcaggaattcg-3'
Probe:           5'-tcactggagctggcctttatgctgc-3'
                 (with minor groove binder)

[Human AdipoR2 gene]
Forward primer:  5'-atagggcagataggctggttga-3'
Reverse primer:  5'-ggatccgggcagcataca-3'
Probe:           5'-ctgatggccagcctctacatcacagga-3'
                 (with minor groove binder)
```

(12) Measurement of Intracellular Calcium Concentration, and cAMP and cGMP Levels Intracellular $Ca^{2+}$ concentrations were measured according to the method of Yokomizo et al (Yokomizo, T. et al, *Nature* 387, 620-624 (1997)). Namely, 10 μM of Fura-2/AM (Dojin) dissolved in Hepes-Tyrode's BSA buffer (25 mM Hepes-NaOH (pH 7.4), 140 mM NaCl, 2.7 mM KCl, 1.0 mM $CaCl_2$, 12 mM $NaHCO_3$, 5.6 mM D-glucose, 0.37 mM $NaH_2PO_4$, 0.49 mM $MgCl_2$, 0.1% [wt/vol] BSA without fatty acids; Fraction V) was contacted with the cells at 37° C. for 2 hours. The cells were washed twice, and suspended at a concentration of $10^6$ cells/mL in Hepes-Tyrode's BSA buffer. 0.5 mL of cell suspension was applied to a CAF-100 system (Jasco), and 5 μL of ligand ethanol solution (for LTB4) or PBS solution (for Adipo) added. Intracellular $Ca^{2+}$ concentrations were measured based on the proportions of 500 nm fluorescence generated by excitation light at 34.0 and 380 nm.

cAMP and cGMP levels were measured according to the method of Yokomizo et al (Yokomizo, T. et al, *Nature* 387, 620-624 (1997)) using assay kits (Biotrak cAMP EIA System for cAMP, Biotrak cGMP EIA System for cGMP, Amersham Pharmacia Biotech) in accordance with manufacturer's protocols.

(13) Predicted Structures of AdipoR1 and AdipoR2

Hydropathy plots of the AdipoR1 and AdipoR2 proteins were conducted using the hydrophobicity indices of Kyte-Doolittle. Structural models for AdipoR1 and AdipoR2 were also predicted by SOSUI, and consensus sequences analyzed by PRINTS (http://bioinf.man.ac.uk/dbbrowser/PRINTS/). In addition, the phosphorylation site was analyzed with DNASIS Pro. Finally, the method described at http://cbrg.inf.ethz.ch/Server/AllAll.html was used to analyze whether AdipoR1/R2 have homology to any other class of GPCR.

(14) Phosphorylation and Amount of Phosphorylation of AMP Kinase (AMPK), ACC, p38 Map Kinase (p38 MAPK) and Map Kinase (MAPK)

Phosphorylation and amount of phosphorylation of AMPK, ACC (Yamauchi, T. et al, *Nat. Med.* 8, 1288-1295 (2002)), p38 MAPK and MAPK (Barger, P. M. et al, *J. Biol. Chem.* 276, 44495-44501 (2001); Puigserver, P. et al, *Mol. Cell.* 8, 971-982 (2001); Michael, L. F. et al, *Proc. Natl. Acad. Sci. USA* 98, 3820-3825 (2001)) were measured by western blotting using anti-phosphorylated AMPK antibodies, anti-phosphorylated ACC antibodies, anti-phosphorylated p38 MAPK antibodies and anti-phosphorylated MAPK antibodies. In this test, C2C12 cells or hepatocytes transfected or not transfected with AdipoR1 were incubated for 10 minutes with 0.1 μg/mL or 1 μg/mL gAd, and lysates of the various cells were reacted with their respective antibodies.

2. Results
(1) Expression Cloning of AdipoR1 and AdipoR2

Figure 1B:
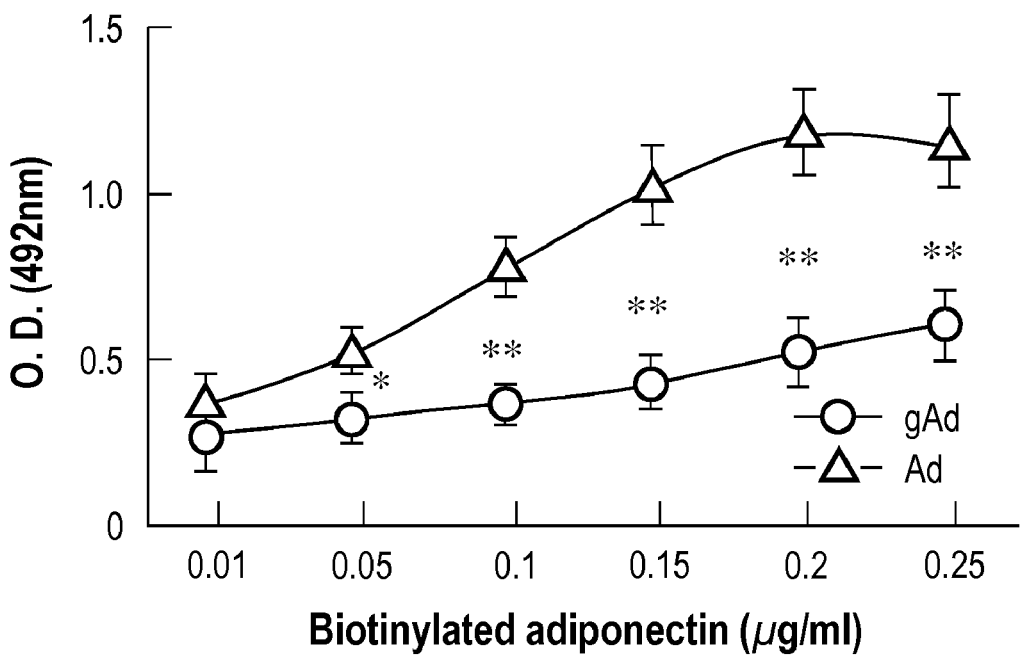
FIG. 1(b) shows the binding of adiponectin to hepatocytes.

In muscle, globular Adipo ameliorates insulin resistance and stimulates PPARα and fatty acid oxidation more than does full-length Adipo (Fruebis, J. et al, *Proc. Natl. Acad. Sci. USA* 98, 2005-2010 (2001); Yamauchi, T. et al, *Nat. Med.* 7, 941-946 (2001); Yamauchi, T. et al, *J. Biol. Chem.* 278, 2461-2468 (2002)). Moreover, globular Adipo binds more strongly to C2C12 cells than does full-length Adipo, and also binds more strongly to skeletal muscle membranes than to hepatocytes and liver membranes (Yamauchi, T. et al, *Nat. Med.* 8, 1288-1295 (2002)) (see FIGS. 1a and 1b). FIG. 1a shows binding of globular Adipo or full-length Adipo to C2C12 myocytes, while FIG. 1b shows binding of globular Adipo or full-length Adipo to hepatocytes. The cells were incubated with biotinylated globular Adipo or full-length Adipo at the concentrations shown, and biotinylated globular Adipo or full-length Adipo bound to the cell surfaces was assayed by ELISA. The bars in the figures indicate mean±s.e. (n=3-5), with "*" indicating P<0.05 and "**" P<0.01.

An effort was then made to isolate AdipoR1 cDNA by screening proteins with globular Adipo binding ability from a library prepared by infecting Ba/F3 cells with a retrovirus having incorporated cDNA derived from human skeletal muscle mRNA.

Figure 1C:
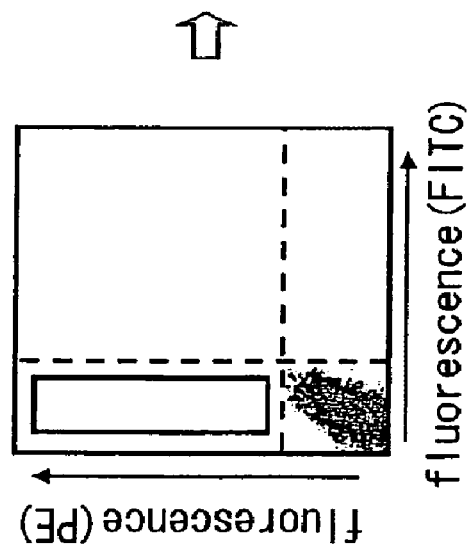
FIGS. 1(c) through 1(e) show the results of FACS analysis.
Figure 1D:
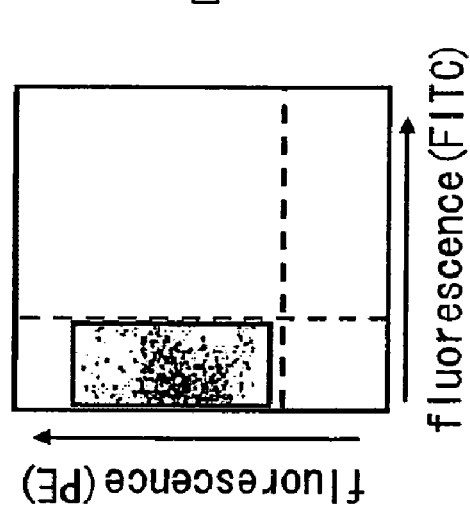
Figure 1E:
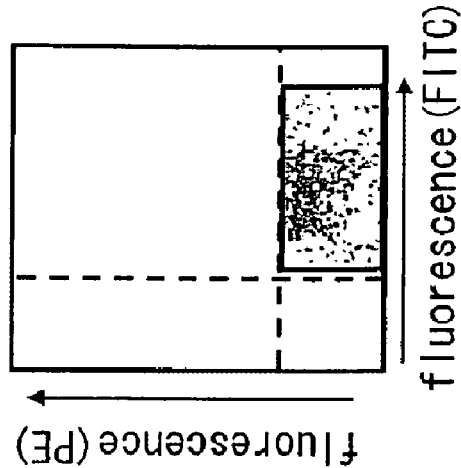

The infected Ba/F3 cells were collected, incubated with biotinylated globular Adipo, stained with streptavidin-conjugated phycoerythrin (PE; red fluorescent probe), and subjected to fluorescence-activated cell sorting (FACS) (see FIG. 1c). The results of FACS analysis are shown in FIGS. 1c, 1d and 1e. FIG. 1c shows the Ba/F3 cells after staining but before first sorting, FIG. 1d shows the Ba/F3 cells before third sorting, and FIG. 1e shows the Ba/F3 cells after incubation with globular Adipo bound with FITC (fluorescein isothiocyanate) but before fourth sorting. The regions in rectangular boxes in FIGS. 1c, 1d and 1e indicate AdipoR1-positive cells, with those in the boxes being selected cells.

The cells selected for globular Adipo binding ability were then subjected to a second round of sorting. The resorted cells that were positive for globular Adipo binding ability (see FIG. 1d) were subjected to a third round of sorting, and the resorted cells immediately incubated with globular Adipo conjugated with FITC (fluorescein isothiocyanate; green fluorescent probe). Since cells which changed from red to green were those having specific binding sites for globular Adipo (see FIG. 1e), only those cells which changed in this way were selected and cultured to expand them for further analysis. Genomic DNA extracted from these cells was subjected to PCR using viral vector primers, and sequenced.

The cells were stained in two colors (red and green) as described above in order to eliminate cells to which globular Adipo was bound non-specifically by its adhesiveness.

Figure 1F:
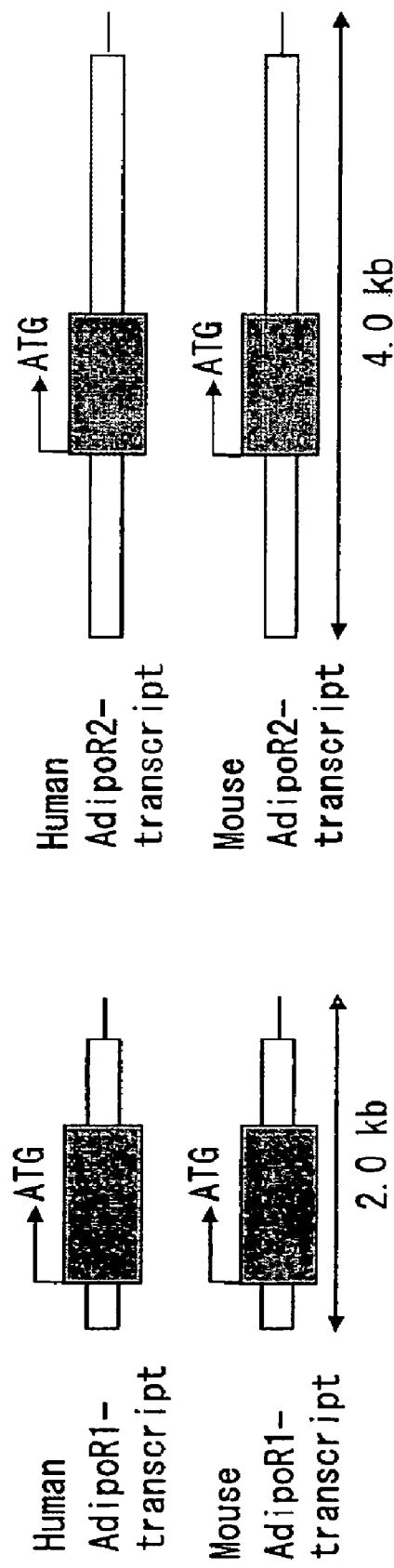
FIG. 1(f) shows a schematic view of the structure of AdipoR1 and AdipoR2 genes transcripts.

The base sequence of the sequenced human AdipoR1 cDNA is shown by Seq. No. 1, and the amino acid sequence of the protein (human AdipoR1) encoded thereby by Seq. No. 2. The base sequence of mouse AdipoR1 cDNA obtained by similar methods from C2C12 myocytes is shown by Seq. No. 5, and the amino acid sequence of the protein (mouse AdipoR1) encoded thereby by Seq. No. 6. Human AdipoR1 cDNA (Seq. No. 1) and mouse AdipoR1 cDNA (Seq. No. 5) are shown to be genes encoding proteins consisting of 375 amino acids (see FIG. 1f). There is 96.8% homology between the amino acid sequences of human AdipoR1 and mouse AdipoR1 (see FIG. 1f). FIG. 1f shows model structures of AdipoR1 and AdipoR2 gene transcripts in databases (NIH-MGC Project and NCBI contig).

From previous findings (Yamauchi, T. et al, *Nat. Med.* 8, 1288-1295 (2002); Yamauchi, T. et al, *J. Biol. Chem.* 278, 2461-2468 (2002)), it appears that there are two types of AdipoR with distinct binding affinities for globular Adipo or full-length Adipo, one type which preferentially binds globular Adipo expressed in skeletal muscle, and another which binds only full-length Adipo expressed in liver.

A search for proteins that share homology with AdipoR1 led to the discovery in human and mouse databases (The Human Genome, http://www.ncbi.nlm.nih.gov/genome/guide/human/; Mouse Genome Resources, http://www.ncbi.nlm.nih.gov/genome/guide/mouse/) (Waterston, R. H. et al, *Nature* 420, 520-562 (2002); Okazaki, Y. et al, *Nature* 420, 563-573 (2002)) of a gene having an open reading frame (ORF) different from that of AdipoR1 cDNA. This cDNA was cloned from the mRNA of HepG2 cells (cell strain derived from human liver cancer) and sequenced, and the protein encoded by this cDNA was named AdipoR2. The base sequence of the sequenced human AdipoR2 cDNA is shown by Seq. No. 3, and the amino acid sequence of the protein encoded thereby (human AdipoR2) by Seq. No. 4. Furthermore, the base sequence of mouse AdipoR2 cDNA obtained by the same methods from C2C12 myocytes is shown by Seq. No. 7, and the amino acid sequence of the protein encoded thereby (mouse AdipoR2) by Seq. NO 8.

There is 95.2% homology between the amino acid sequences of human AdipoR2 and mouse AdipoR2. AdipoR1 and AdipoR2 are extremely similar structurally, with 66.7% homology between the amino acid sequences of mouse AdipoR1 and AdipoR2.

In SWISS-PROT, there were no mammalian proteins having high homology with AdipoR1 and AdipoR2, but interestingly the cDNA encoding AdipoR1 and AdipoR2 had homology with yeast YOL002c (Karpichev, I. V. et al, *J. Biol. Chem.* 277, 19609-19617 (2002)). YOL002c is reported to encode a seven transmembrane protein that plays a key role in metabolic pathways which regulate lipid metabolism such as fatty acid oxidation (Karpichev, I. V. et al, *J. Biol. Chem.* 277, 19609-19617 (2002)). It appears that AdipoR/YOL002c with a seven transmembrane structure across species mediates key regulatory signals in lipid metabolism such as fatty acid oxidation.

(2) Tissue distribution of AdipoR1 and AdipoR2

Figure 1G:
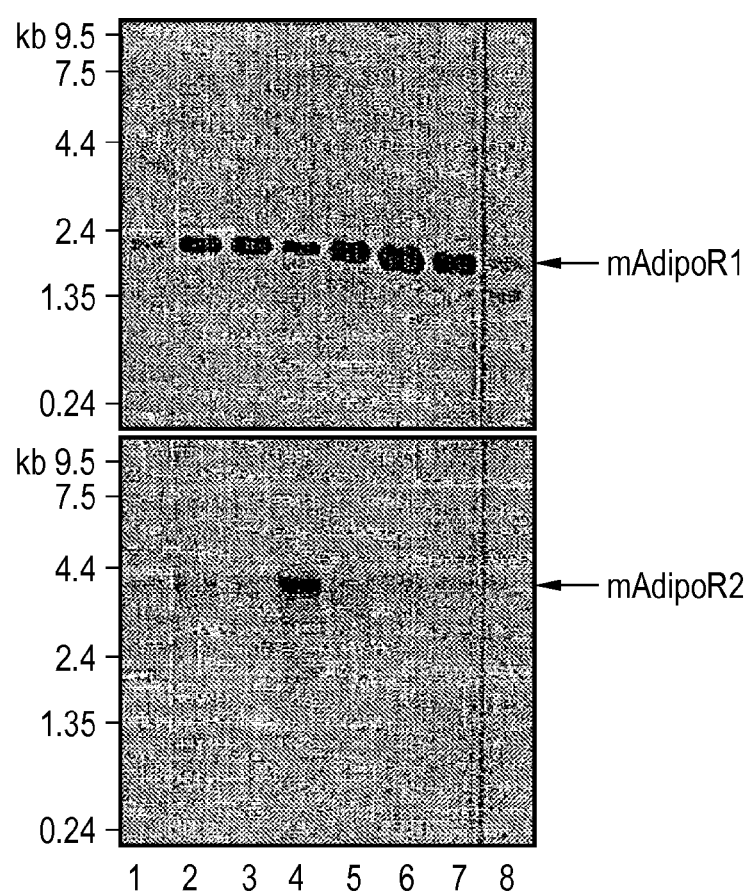
FIG. 1(g) shows the results of northern blot analysis for various mouse tissues.
Figure 1H:
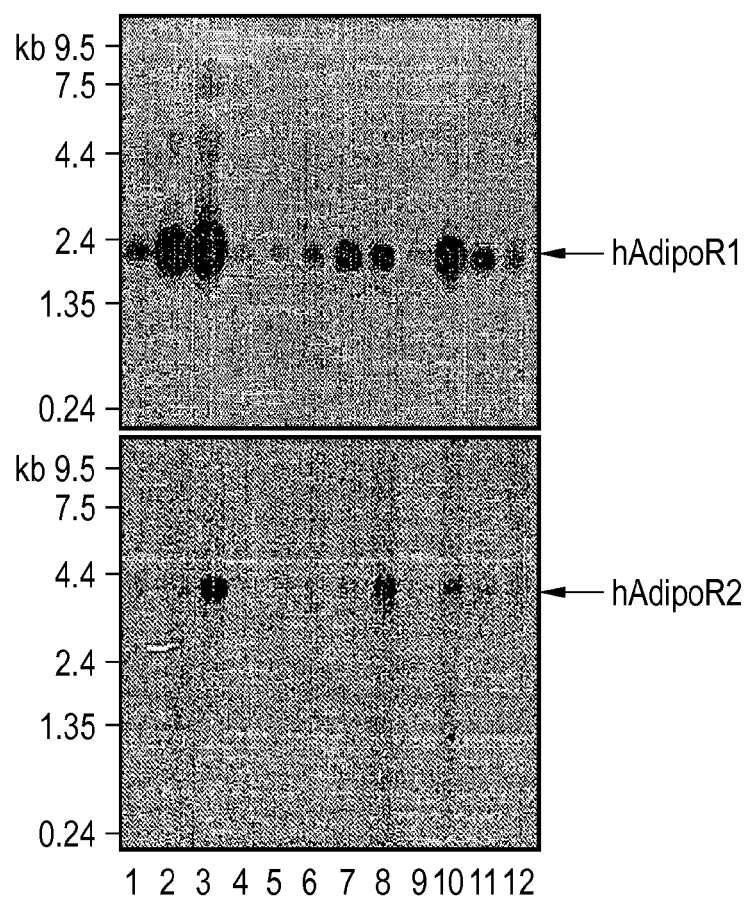
FIG. 1(h) shows the results of northern blot analysis for various human tissues.

The results of northern blot analysis of various mouse tissues are shown in FIG. 1g, and the results of northern blot analysis of various human tissues in FIG. 1h. In FIG. 1g, lane 1 shows results for the brain, lane 2 for heart, lane 3 for kidney, lane 4 for liver, lane 5 for lung, lane 6 for skeletal muscle, lane 7 for spleen, and lane 8 for testis, while in FIG. 1h, lane 1 shows results for brain, lane 2 for heart, lane 3 for skeletal muscle, lane 4 for colon, lane 5 for thymus, lane 6 for spleen, lane 7 for kidney, lane 8 for liver, lane 9 for small intestine, lane 10 for placenta, lane 11 for lung and lane 12 for peripheral blood leukocytes.

Northern blot analysis of various human and mouse tissues, identified one major 2.0 kb band with the predicted mRNA size in the aforementioned database, and also revealed that AdipoR1 is expressed in most tissues and most abundantly expressed in skeletal muscle. One major 4.0 kb band with the predicted mRNA size was also identified in the aforementioned database, and it was shown that AdipoR2 is most abundantly expressed in the liver.

(3) Cellular locations of AdipoR1 and AdipoR2

Figure 2A:
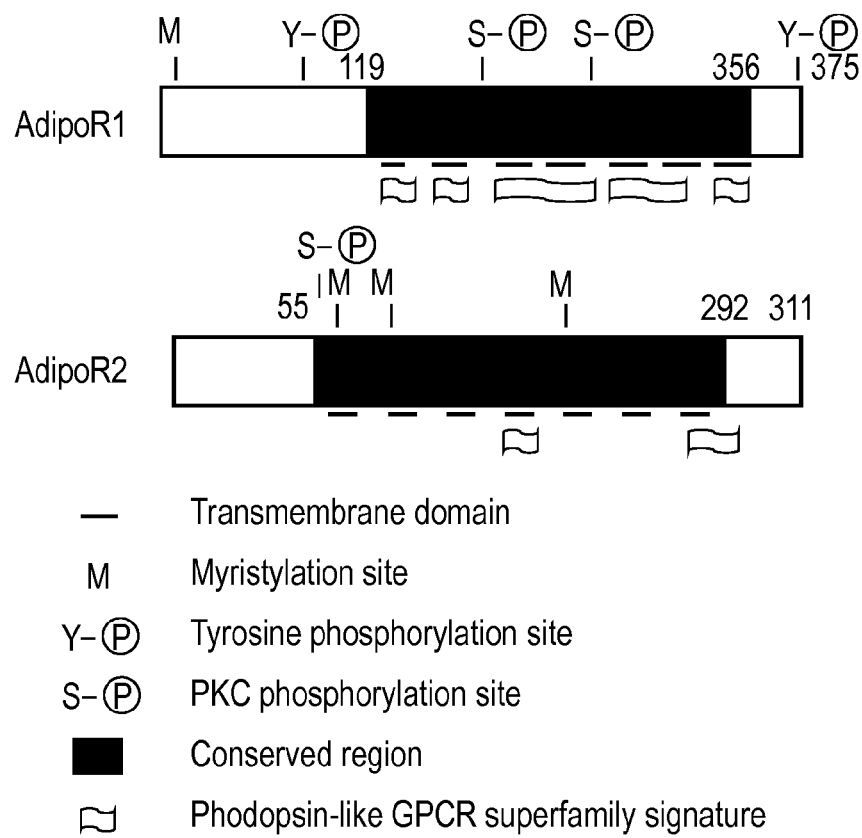
FIG. 2(a) shows a schematic view of the structures of AdipoR1 and AdipoR2.

From the deduced amino acid sequence (Seq. No. 6) of mouse AdipoR1, it is predicted that mouse AdipoR1 is a protein consisting of 375 amino acids and having a molecular weight of 42.4 kDa. From the deduced amino acid sequence (Seq. No. 8) of mouse AdipoR2, it is predicted that mouse AdipoR2 is a protein consisting of 311 amino acids and having a molecular weight of 35.4 kDa (see FIG. 2a). In FIG. 2a, which shows the results of a scan of the AdipoR sequence by PRINTS software (http://bioinf.man.ac.uk/dbbrowser/PRINTS/), the underlined regions are the 7 transmembrane domains of AdipoR1 and AdipoR2, while the areas underlined in bold indicate the characteristic conserved motifs of G-protein coupled receptor members. PKC phosphorylation sites and tyrosine phosphorylation sites are also shown in FIG. 2a.

From the deduced amino acid sequences of AdipoR1 and AdipoR2, it is predicted that AdipoR1 and AdipoR2 are proteins having 7 transmembrane domains (see FIG. 2a). An alignment of AdipoR1 and AdipoR2 was performed with known receptors having 7 transmembrane domains (Waterston, R. H. et al, *Nature* 420, 520-562 (2002); Okazaki, Y. et al, *Nature* 420, 563-573 (2002); Wess, J., *FASE B. J.* 11, 346-354 (1997)), but homology to the amino acid sequences of members of the G-protein coupled receptor (GPCR) family was low. AdipoR1 and AdipoR2 lacked characteristics (such as conserved amino acids, glycosylation sites, sites for G-protein coupling) of the G-protein coupled receptor family (Wess, J. et al, *FASEB. J.* 11, 346-354 (1997); Yokomizo, T. et al, *Nature* 387, 620-624 (1997); Scheer, A. et al, *EMBO. J.* 15, 3566-3578 (1996)). Of the highly conserved amino acids in the G-protein coupled receptor family, only one of two highly conserved Cys residues were present in the first and second extracellular loops of AdipoR1 and AdipoR2. AdipoR1 and R2 lacked the highly conserved Asn-Pro-Xaa2-Tyr motif present at the end of TM7. AdipoR1 and AdipoR2 also lacked the highly conserved Asp-Arg-Tyr motif present at the TM3/intracellular loop 2 transition (Wess, J. et al, *FASEB. J.* 11, 346-354 (1997); Scheer, A. et al, *EMBO. J.* 15, 3566-3578 (1996)).

Figure 2B:
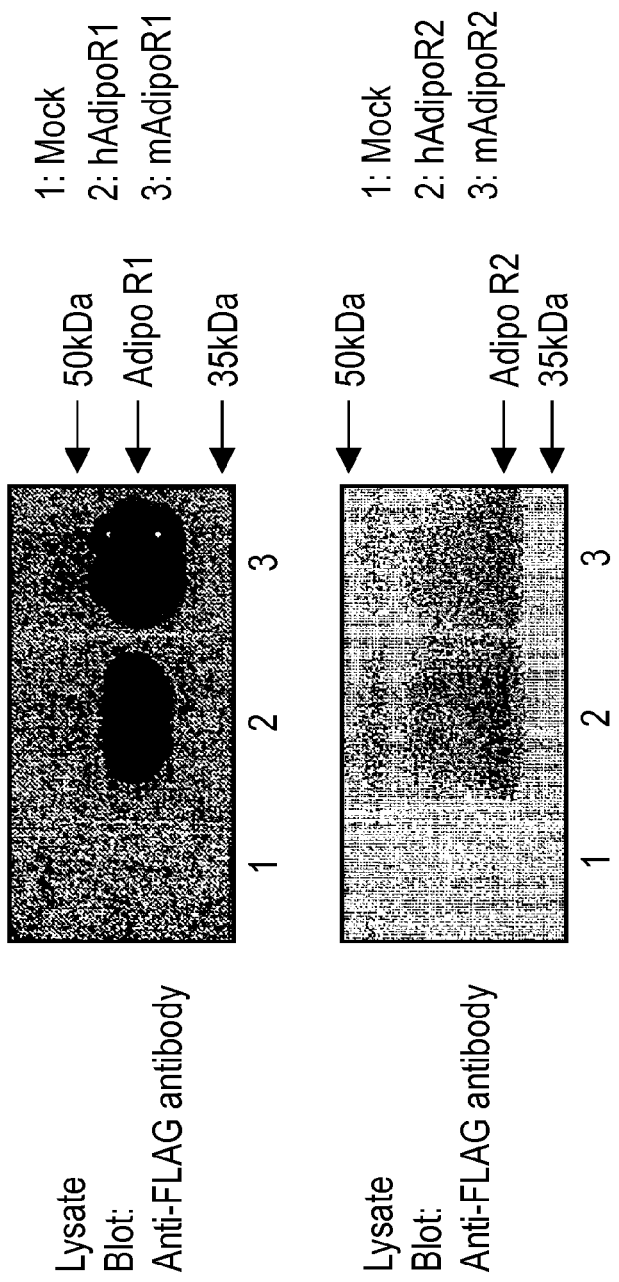
FIG. 2(b) shows the results of immunoblotting with anti-FLAG antibodies of cell lysates from 293T cells transfected with AdopR1 and AdipoR2 having the epitope tag FLAG.

Human and mouse AdipoR1 or AdipoR2 labeled with epitope tag FLAG was expressed in HEK-293 cells, and immunoblotted with anti-FLAG antibodies. Human and mouse AdipoR1 and AdipoR2 exhibited the expected molecular weights (see FIG. 2b).

Figure 2C:
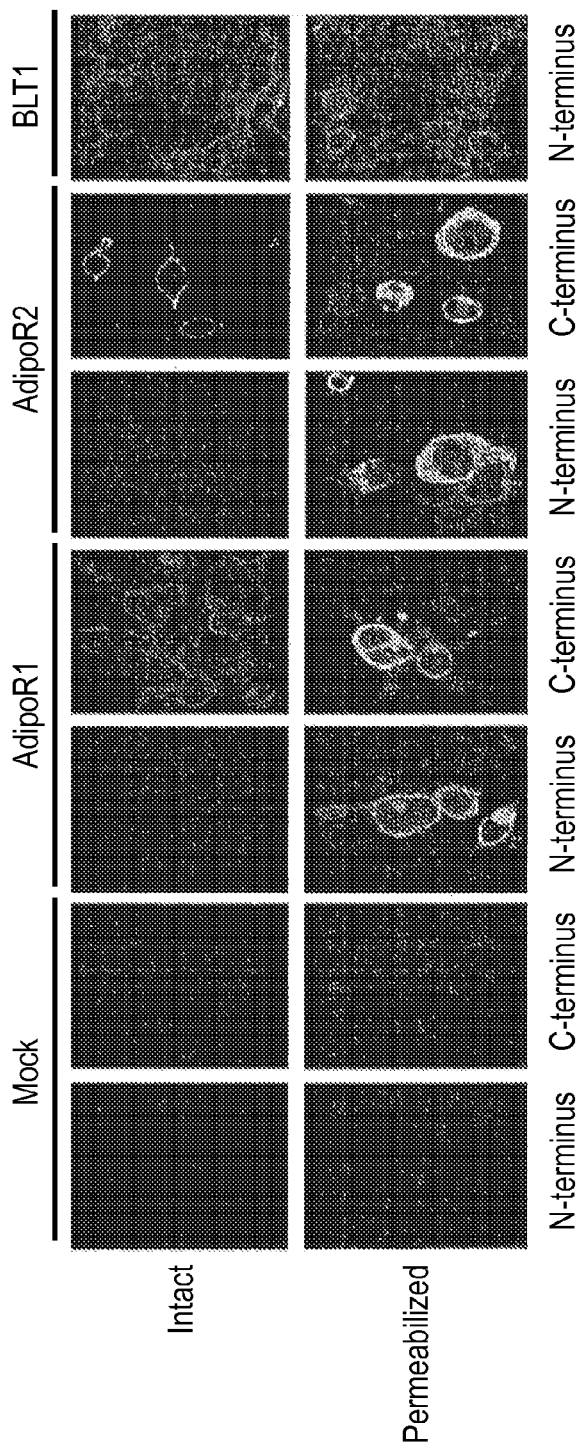
FIG. 2(c) shows the intracellular locations of AdipoR1 or AdipoR2 in 293T cells transfected with AdipoR1 and AdipoR2 having epitope flags introduced at the N or C end.

To determine the subcellular location and topology of mouse AdipoR1 and AdipoR2, AdipoR1 or AdipoR2 cDNA with epitope tags at either end was expressed in HEK-293T cells (see FIG. 2c). In FIG. 2c, "intact" indicates that the cells were not permeabilized and "permeabilized" indicates that they were.

Figure 2D:
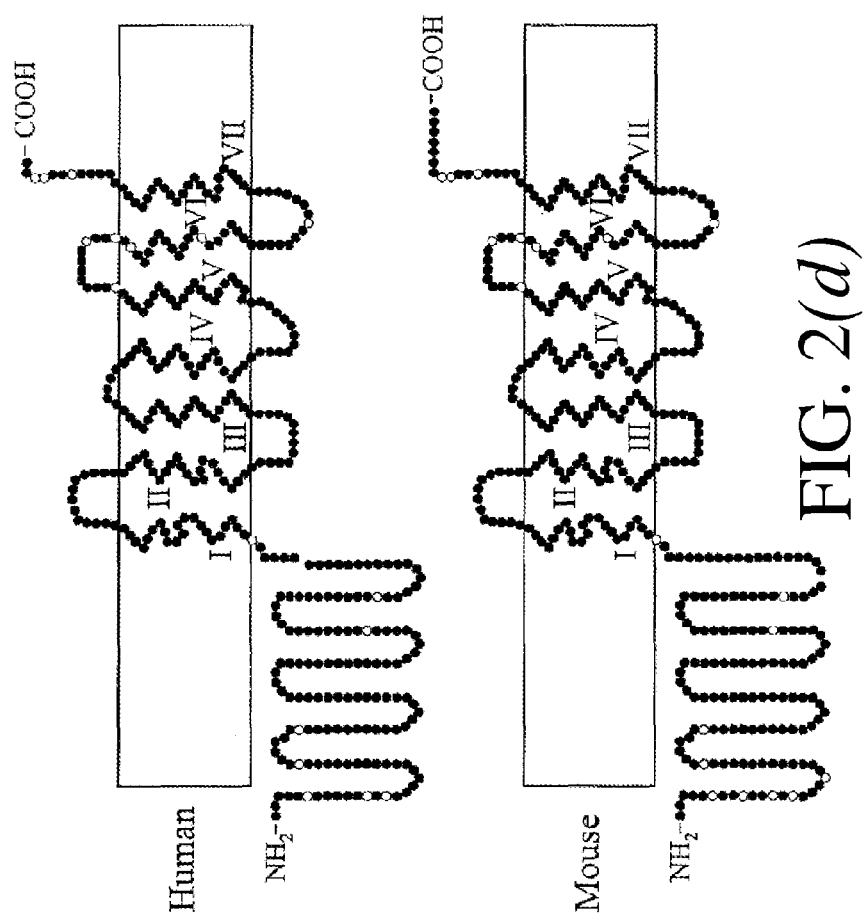
FIGS. 2(d) and 2(e) show the predicted structural models of Adipo R1 and AdipoR2, respectively.
Figure 2E:
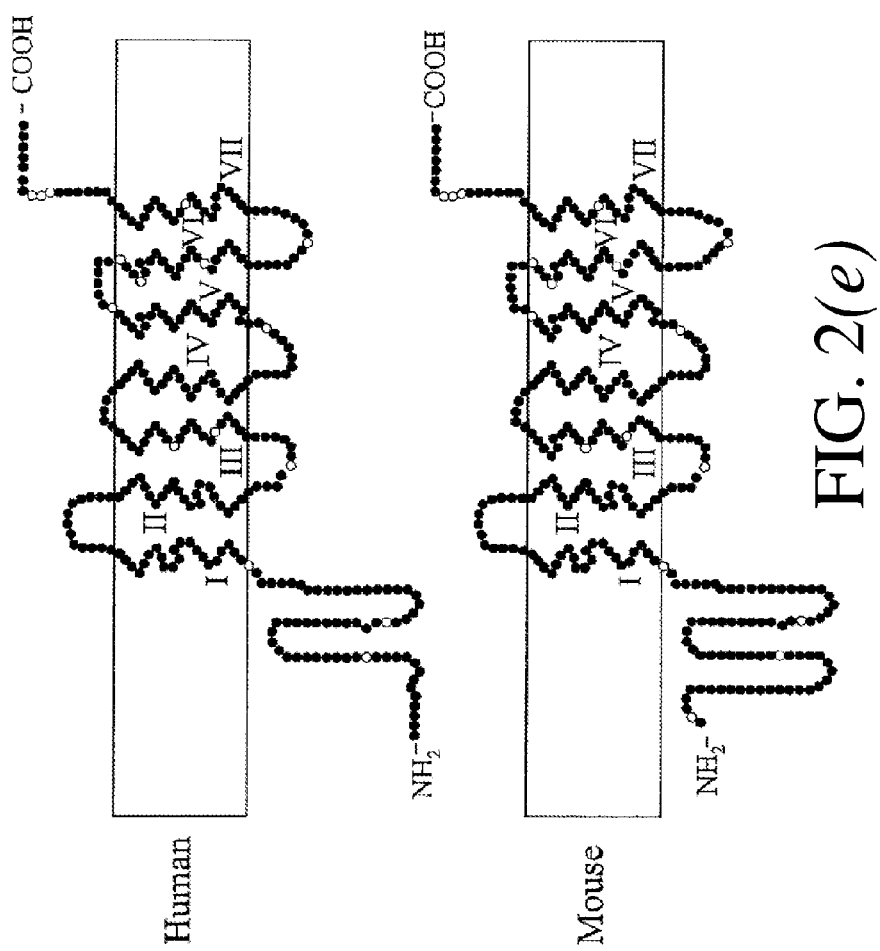

When the epitope tag was inserted at the N-terminus, AdipoR1 and AdipoR2 could be detected at the cell surface only when the cells were permeabilized (see FIG. 2c). In contrast, when the epitope tag was inserted at the C-terminus, AdipoR1 and AdipoR2 could be detected at the cell surface (see FIG. 2c). These results indicate that AdipoR1 and AdipoR2 are integral membrane proteins with seven transmembrane domains, in which the N-terminus is within the membrane and the C-terminus is outside the membrane (see FIGS. 2c, 2d). This is opposite to the topology of all reported G-protein coupled receptors (Wess, J. et al, *FASEB. J.* 11, 346-354 (1997); Yokomizo, T. et al, *Nature* 381, 620-624 (1997); Scheer, A. et al, *EMBO J.* 15, 3566-3578 (1996)). Hypothetical structural models of AdipoR1 and AdipoR2 are shown in FIGS. 2d and 2e, respectively.

(4) Effects of AdipoR Expression in 293T Cells

Figure 3A:
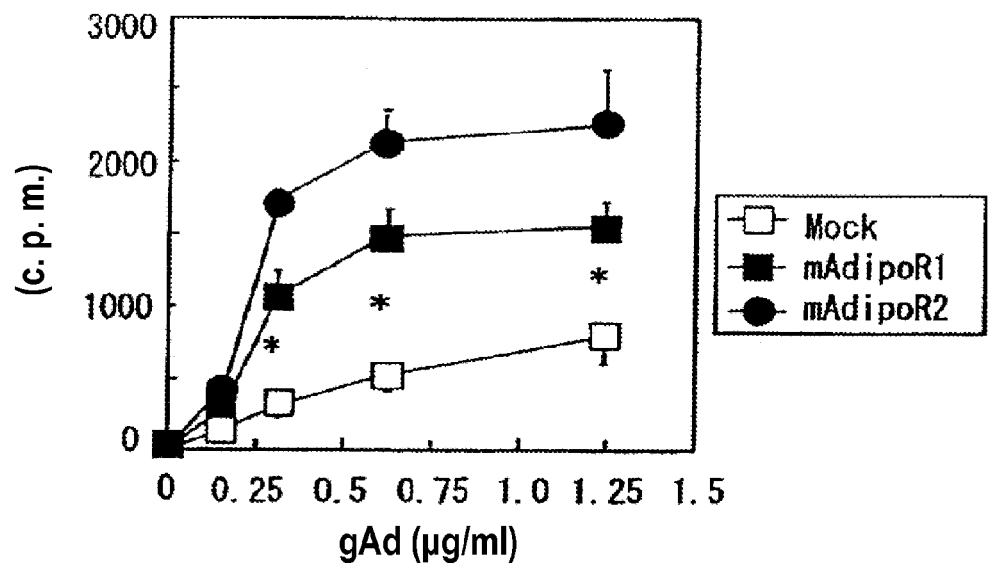
FIG. 3(a) shows the binding isotherm of [$^{125}$I] globular Adipo (gAd) binding to 293T cells transfected with AdipoR1 or AdipoR2.
Figure 3B:
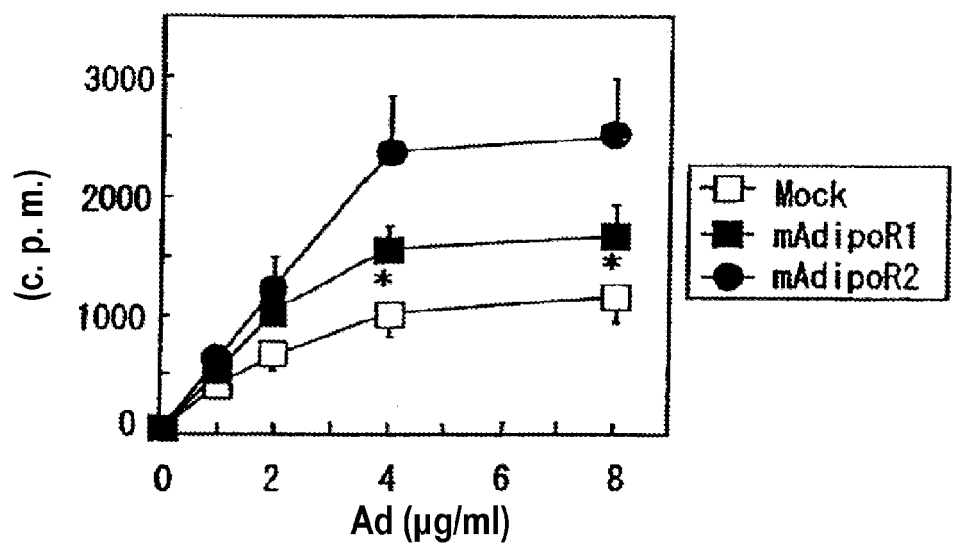
FIG. 3(b) shows the binding isotherm of [$^{125}$I] full-length Adipo (Ad) binding to the 293T cells.

The binding and intracellular signaling stimulated by globular Adipo or full-length Adipo using 293T cells overexpressing AdipoR1 or AdipoR2 on the cell surface were examined. Expression of AdipoR1 or AdipoR2 in 293T cells enhanced binding of both globular Adipo and full-length Adipo (see FIGS. 3a, 3b). FIG. 3a shows the binding isotherm of $[^{125}I]$ globular Adipo (gAd) binding to 293T cells transfected with AdipoR1 or AdipoR2, while FIG. 3b shows the binding isotherm of $[^{125}I]$ full-length Adipo (Ad) binding to the 293T cells. In these figures, a white square indicates a result for mock, a black square a result for mouse AdipoR1 and a black circle a result for mouse AdipoR2.

Figure 3C:
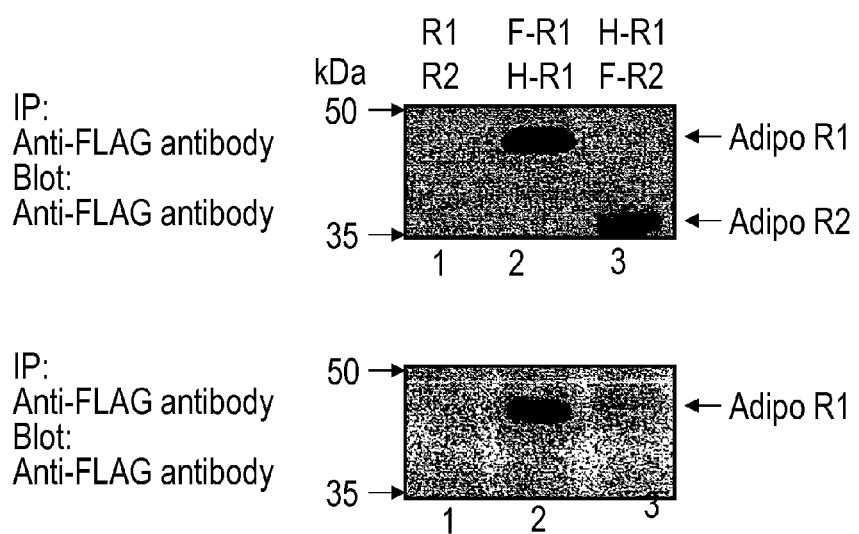
FIG. 3(c) shows the results when cell lysates of 293T" cells transfected with AdipoR1 or AdipoR2 having the epitope tag FLAG or HA are immunoprecipitated with an anti-FLAG or anti-HA antibody, and then immunoblotted with the anti-FLAG or anti-HA antibody.

We next examined whether AdipoR1 and AdipoR2 could form multimers. When AdipoR1 with the epitope tag FLAG and AdipoR1 with the epitope tag HA were co-expressed in HEK-293T cells, AdipoR1 with the epitope tag FLAG was detected in anti-HA antibody immunoprecipitates (see FIG. 3c). FIG. 3c shows the results when cell lysates of 293T cells transfected with AdipoR1 or AdipoR2 having epitope tag FLAG or HA were immunoprecipitated (IP) with anti-FLAG antibody (upper and lower panels), and then immunoblotted with anti-FLAG (upper panel) or anti-HA (lower panel) antibody, and indicates formation of AdipoR1 and AdipoR2 homo-and hetero-multimers.

Moreover, when AdipoR1 with the epitope tag HA and AdipoR2 with the epitope tag FLAG were co-expressed in HEK-293T cells, AdipoR2 with the epitope tag FLAG was detected in anti-HA antibody immunoprecipitates (see FIG. 3c). These data suggest that AdipoR1 and AdipoR2 may be able to form both homo-and hetero-multimers.

Figure 3D:
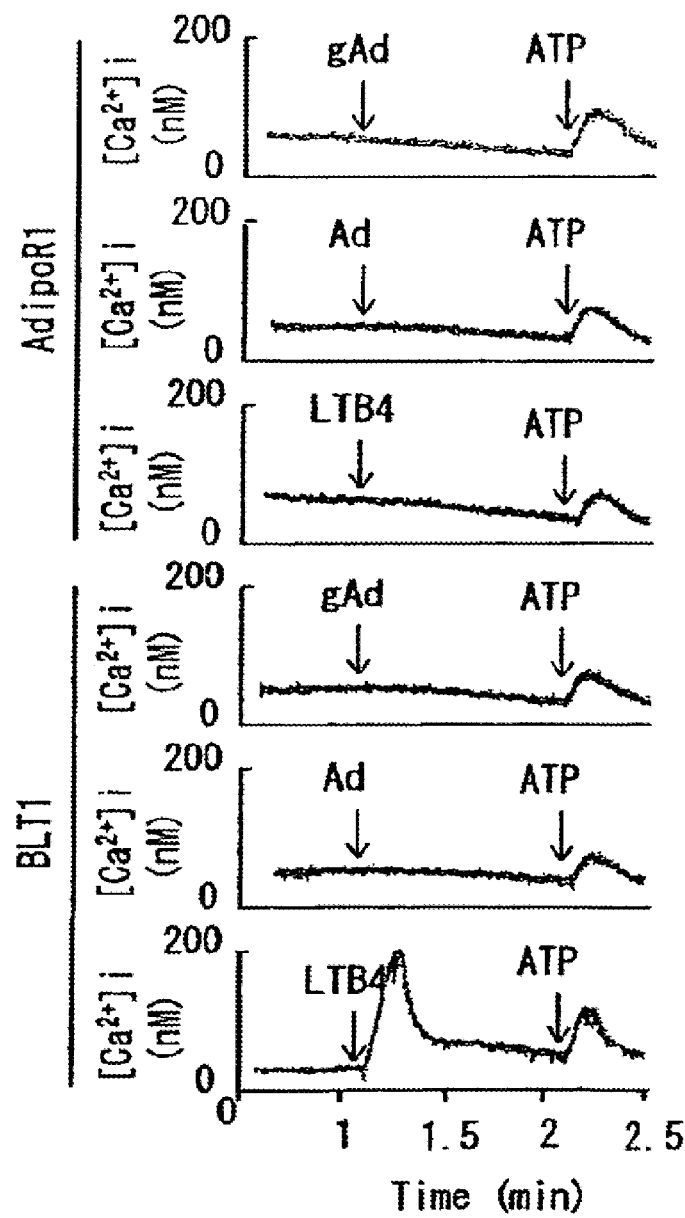
FIG. 3(d) shows changes in [Ca$^{2+}$]i when mouse AdipoR1-expressing cells or BLT1-expressing cells were challenged with globular Adipo, full-length Adipo, LTB4 or ATP.

In cells expressing AdipoR1, Adipo had no apparent effect on intracellular calcium, although LTB4 increased intracellular calcium in cells expressing either GPCR or LTB4 receptor BLT1 (see FIG. 3d), and these cells showed similar expression levels to those of cells expressing AdipoR1 (data not shown). FIG. 3d shows measurement results for changes in $[Ca^{2+}]i$ when BLT1-expressing cells or mouse AdipoR1-expressing cells loaded with Fura-2/AM were challenged with 10 μg/mL globular Adipo (gAd), 10 μg/mL full-length Adipo (Ad), 1 μM LTB4 or 100 μM ATP.

Figure 3E:
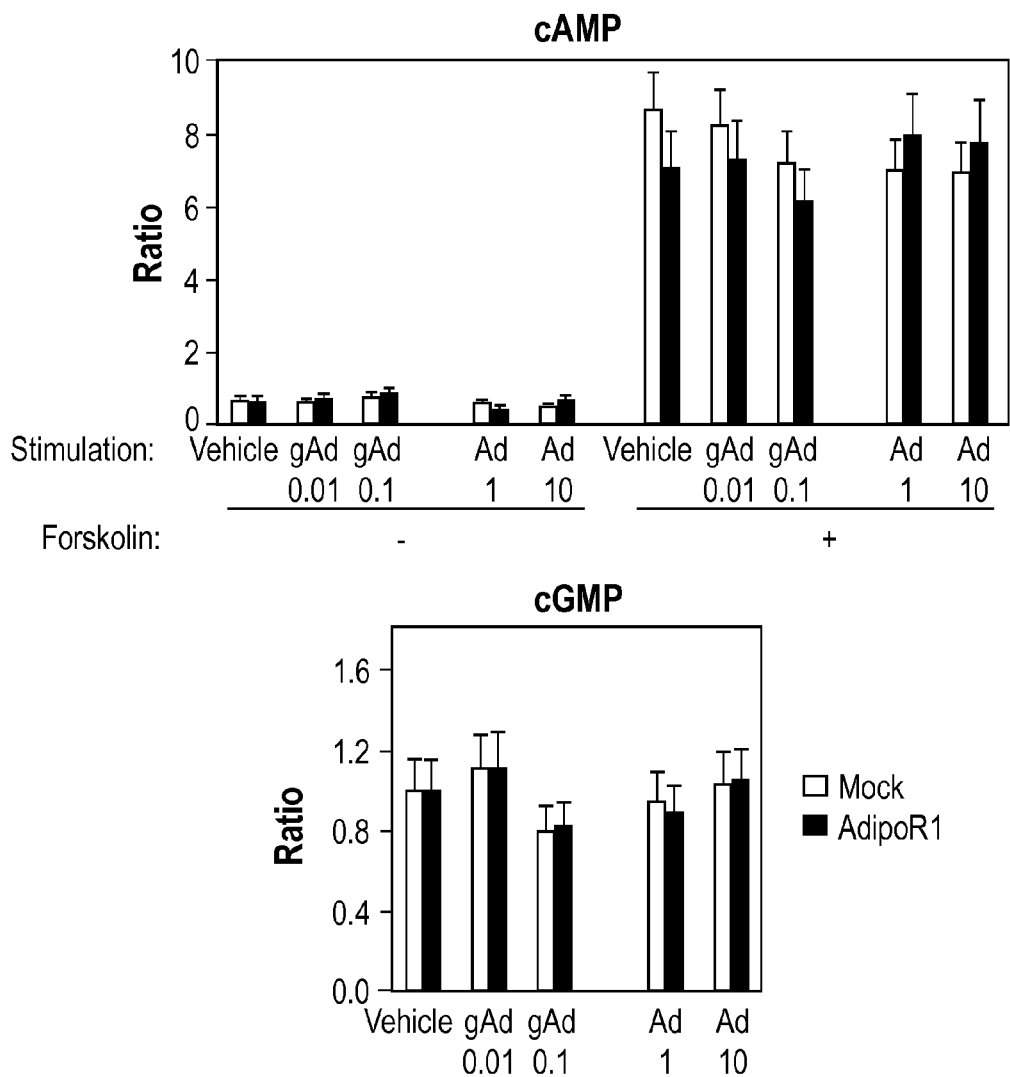
FIG. 3(e) shows the results for accumulation of cAMP or cGMP in HEK-29 cells treated with or without forskolin.
Figure 3F:
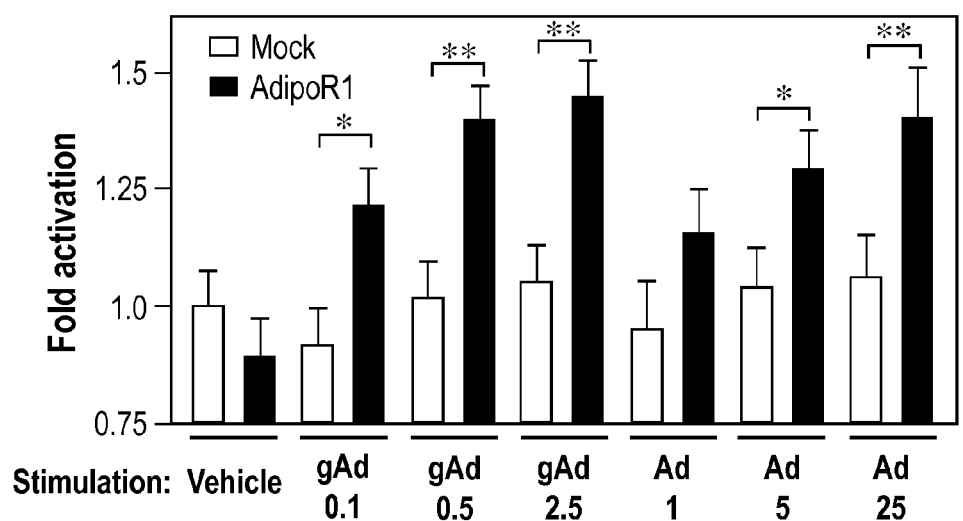
FIG. 3(f) shows PPARα ligand activity in 293T cells transfected with AdipoR1 that are incubated with globular Adipo or full-length Adipo.

Moreover, in cells expressing AdipoR1, AdipoR1 had little or no apparent effect on cAMP and cGMP levels (see FIG. 3e). FIG. 3e shows results for accumulation of cAMP or cGMP in HEK-293 cells treated with or without forskolin, with "gAd0.01" and "gAd0.1" indicating 0.01 or 0.1 μg/mL of globular Adipo, respectively, and "Ad1" and "Ad10" indicating 1 and 10 μg/mL of full-length Adipo, respectively. In contrast, expression of AdipoR1 enhanced increases in PPARα ligand activity by globular Adipo and full-length Adipo in 293T cells (see FIG. 3f). FIG. 3f shows in PPARα ligand activity in AdipoR1-transfected 293T cells incubated with the indicated concentrations (μg/mL) of globular Adipo or full-length Adipo, with "gAd0.1," "gAd0.5" and "gAd2.5" indicating 0.1, 0.5 and 2.5 μg/mL of globular Adipo, respectively, and "Ad1," "Ad5" and "Ad25" indicating 1, 5 and 25 μg/mL of full-length Adipo, respectively. In the figure each bar shows mean±s.e. (n=3-5), with "*" indicating P<0.05 and "**" P<0.01.

(5) PPARα Activation and Fatty Acid Oxidation in C2C12 Myocytes

Figure 4A:
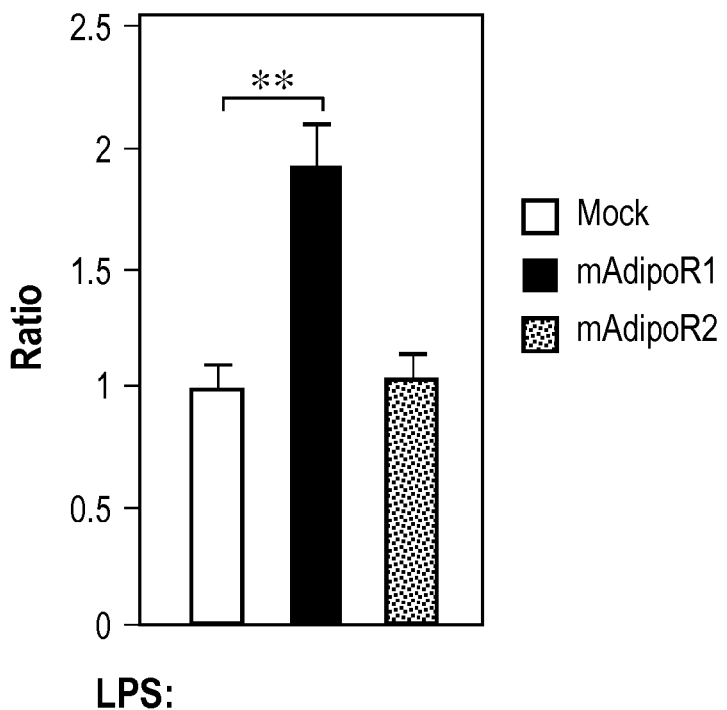
FIG. 4(a) shows mouse AdipoR1 mRNA levels.
Figure 4B:
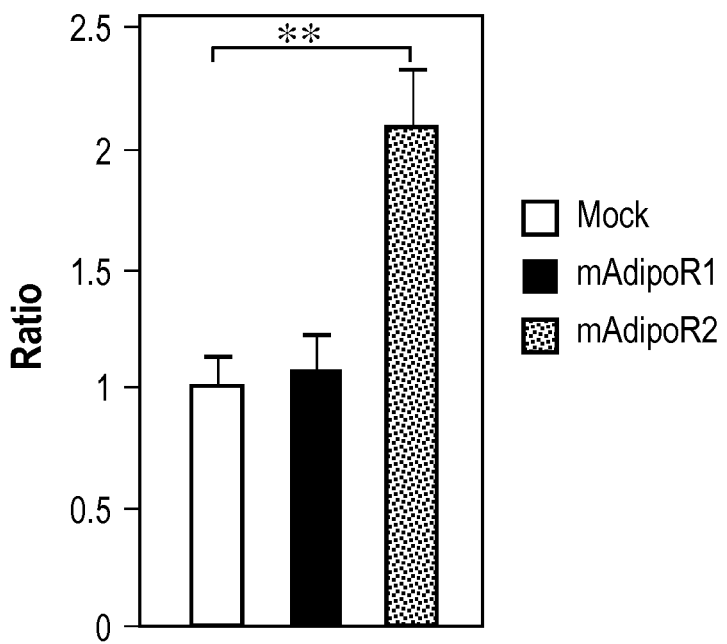
FIG. 4(b) shows mouse AdipoR2 mRNA levels.
Figure 4C:
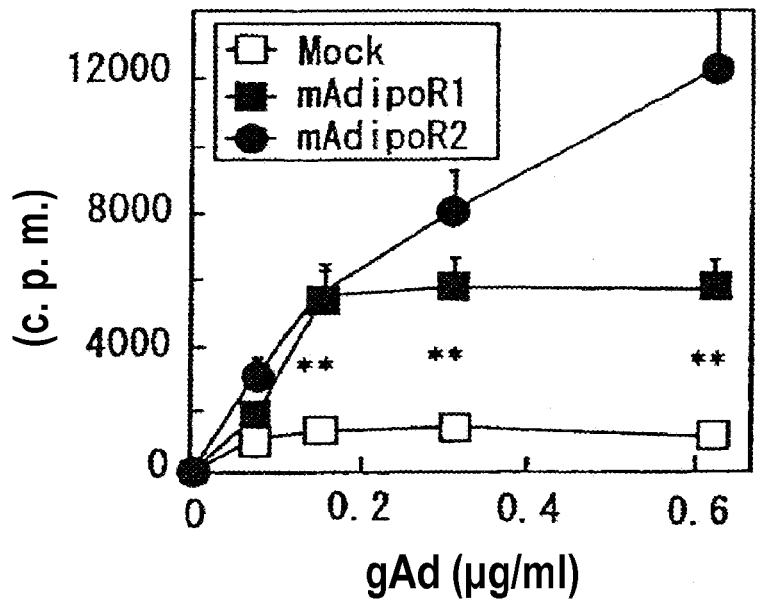
FIGS. 4(c) and 4(d) show binding isotherms of [$^{125}$I] globular Adipo (gAd) or full-length Adipo (Ad) binding to C2C12 myocytes transfected with mouse AdipoR1 or AdipoR2.
Figure 4D:
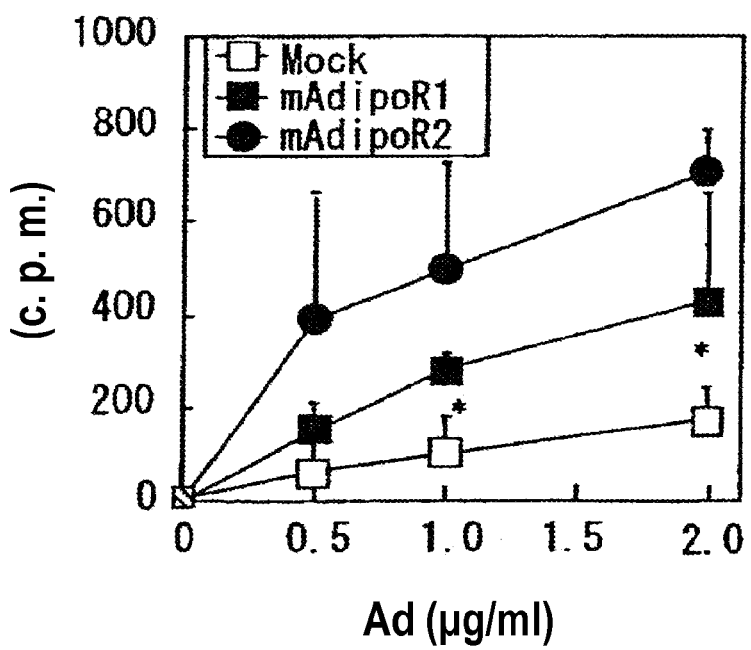
Figure 4E:
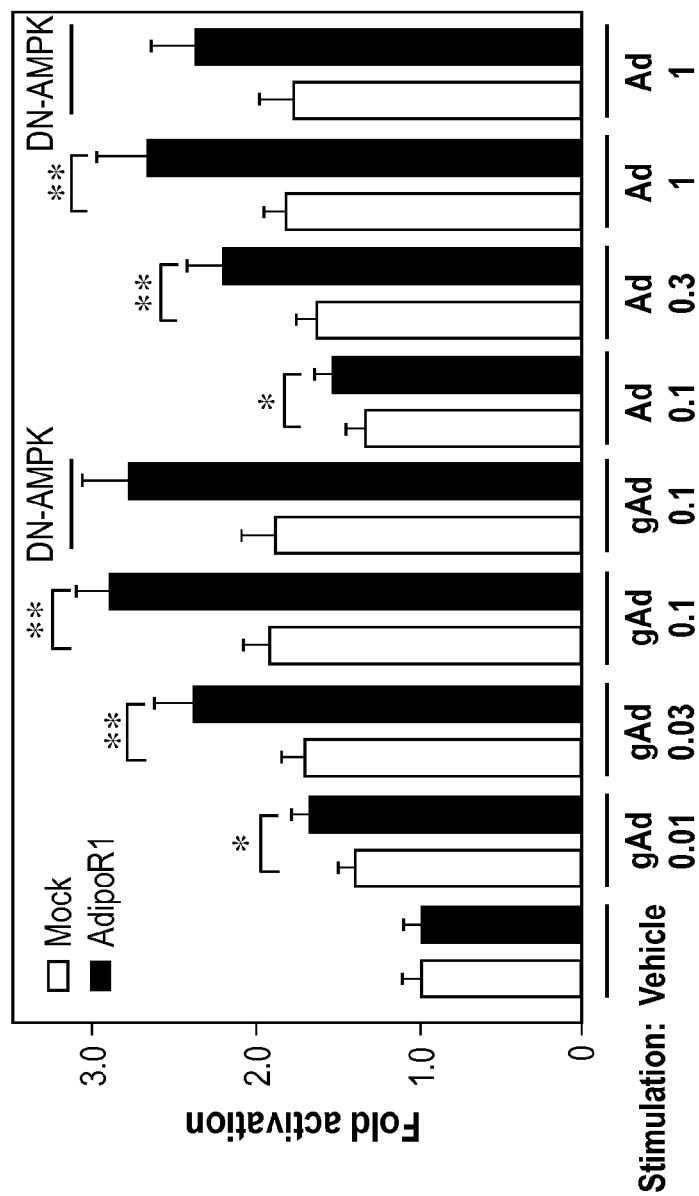
FIG. 4(e) shows PPARα ligand activity in C2C12 myocytes transfected with mouse AdipoR1 or Adipo R2 which were infected with an adenovirus containing LacZ or DN-α2AMPK and treated for 7 hours with globular Adipo or full-length Adipo.
Figure 4F:
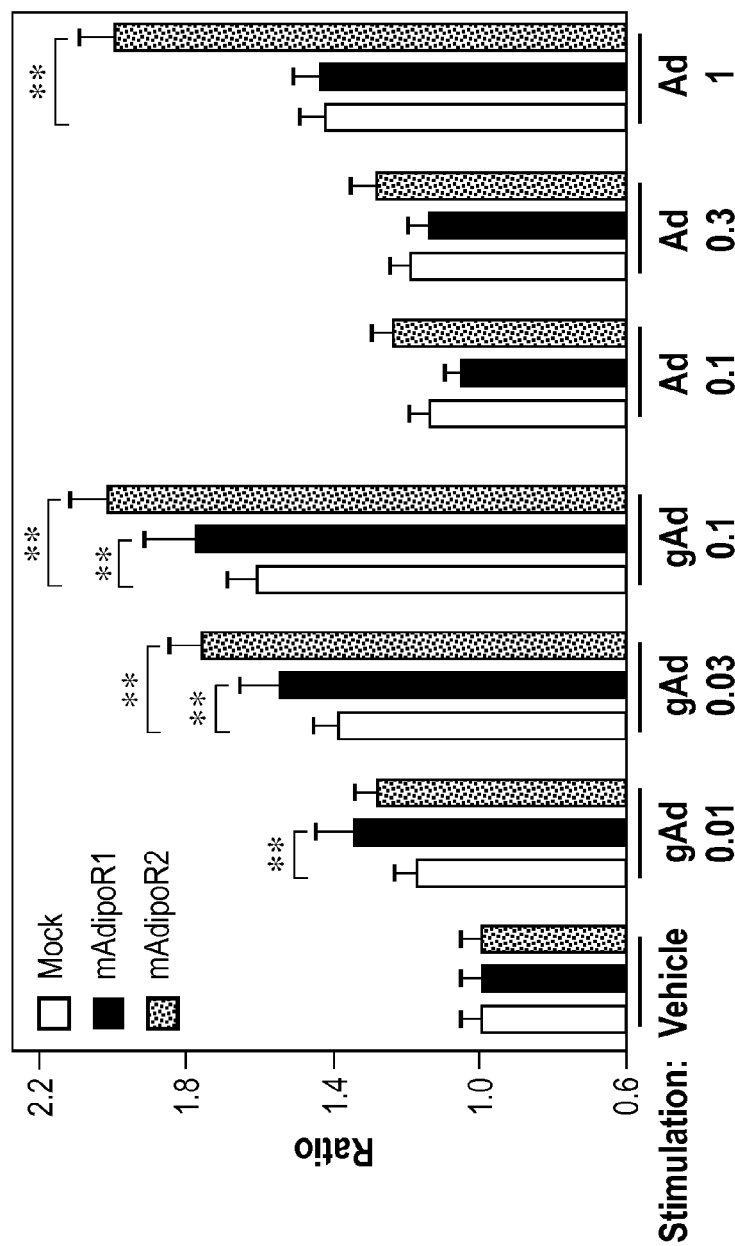
FIG. 4(f) shows in vitro fatty acid oxidation in the C2C12 myocytes.

Expression of AdipoR1 in C2C12 myocytes (see FIG. 4a) enhanced binding of both globular and full-length Adipo (see FIGS. 4c, 4d), which was associated with increases in PPARα ligand activity (see FIG. 4e) and fatty acid oxidation (see FIG. 4f) by globular Adipo and full-length Adipo in C2C12 myocytes. Expression of AdipoR2 in C2C12 myocytes (see FIG. 4b) also enhanced binding of both globular Adipo and full length-Adipo (see FIGS. 4c, 4d), which was associated with increases in fatty acid oxidation (see FIG. 4f) by globular and full-length Adipo in C2C12 myocytes. FIG. 4a shows mouse AdipoR1 mRNA levels and FIG. 4b mouse AdipoR2 mRNA levels, with results shown using a white bar for Mock, a black bar for mouse AdipoR1, and a dotted white bar for mouse AdipoR2. FIGS. 4c and 4d show the binding isotherm of [$^{125}$I] globular Adipo (gAd) or full-length Adipo (Ad) binding to C2C12 myocytes transfected with mouse AdipoR1 or mouse AdipoR2, with a white square indicating Mock, a black square mouse AdipoR1 and a black circle mouse AdipoR2. FIG. 4e show PPARα ligand activity in C2C12 myocytes transfected with mouse AdipoR1 or AdipoR2 when the myocytes were infected with adenovirus containing LacZ or DN-α2 AMPK and treated for 7 hours with the indicated concentrations (μg/mL) of globular Adipo or full-length Adipo, with white bars indicating results for Mock and black bars for mouse AdipoR1. FIG. 4f shows in vitro fatty acid oxidation in the aforementioned C2C12 myocytes, with white bars indicating results for Mock, black bars for mouse AdipoR1 and dotted white bars for mouse AdipoR2. In all these figures, the bars show mean±s.e. (n=3-5), with "*" indicating P<0.05 and "**" P<0.01.

Expression of dominant negative AMP kinase did not affect globular and full-length Adipo-induced and AdipoR1 expression-dependent increases in PPARα ligand activity. These data strongly suggest that both AdipoR1 and AdipoR2 can mediate binding of globular and full-length Adipo and stimulate increases in PPARα ligand activity and fatty acid oxidation by globular and full-length Adipo.

(6) Effects of siRNA on Binding and Action of AdipoR in Myocytes

Figure 5A:
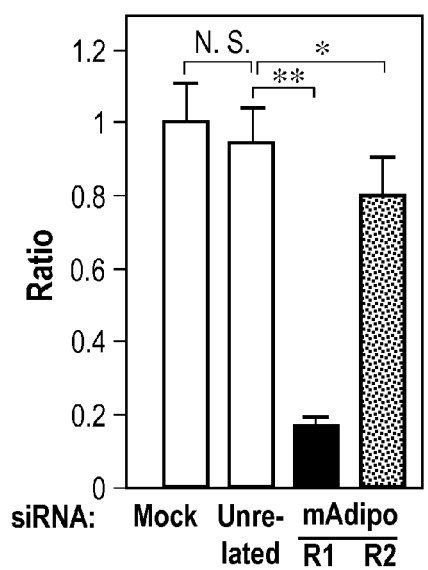
FIG. 5(a) shows mouse AdipoR1 mRNA levels in C2C12 myocytes transfected with siRNA or mock.
Figure 5B:
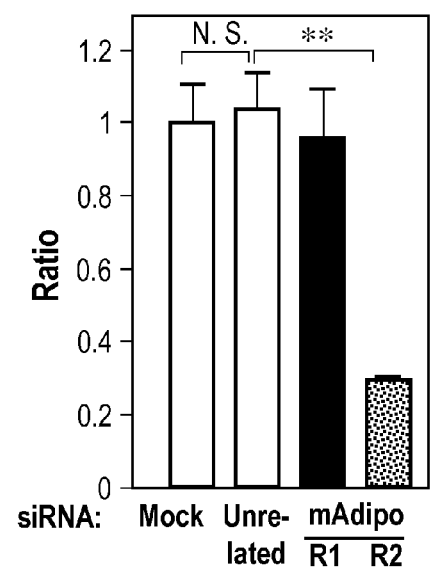
FIG. 5(b) shows mouse AdipoR2 mRNA levels in the C2C12 myocytes.

To determine whether endogenous AdipoR1 and R2 mediate the specific binding and metabolic effects of Adipo in muscle cells, AdipoR1 and R2 expression was suppressed using siRNA (see FIGS. 5a, 5b). FIG. 5a shows mouse AdipoR1 mRNA levels in C2C12 myocytes transfected with siRNA or mock, while FIG. 5b shows mouse AdipoR2 mRNA levels in the C2C12 myocytes. In FIGS. 5a and 5b, lane 1 shows results using mock, lane 2 using unrelated siRNA, lane 3 using siRNA for mouse AdipoR1 gene and lane 4 using siRNA for mouse AdipoR2 gene.

Figure 5C:
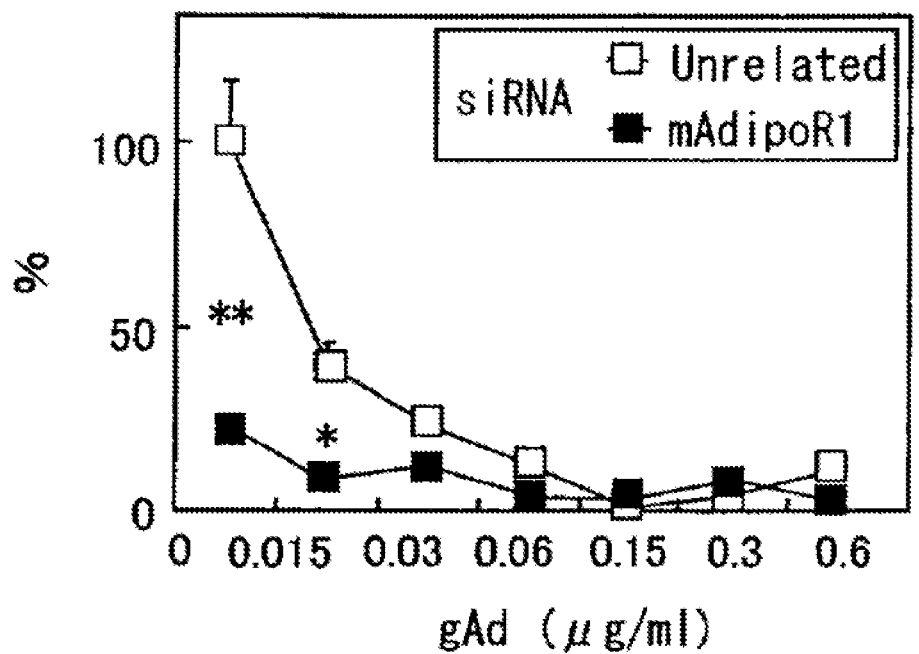
FIG. 5(c) shows the results of a competitive radioligand binding assay in which [$^{125}$I] globular Adipo binding to cells transfected with snRNA dublex is displaced by increasing concentrations of unlabeled globular Adipo.
Figure 5D:
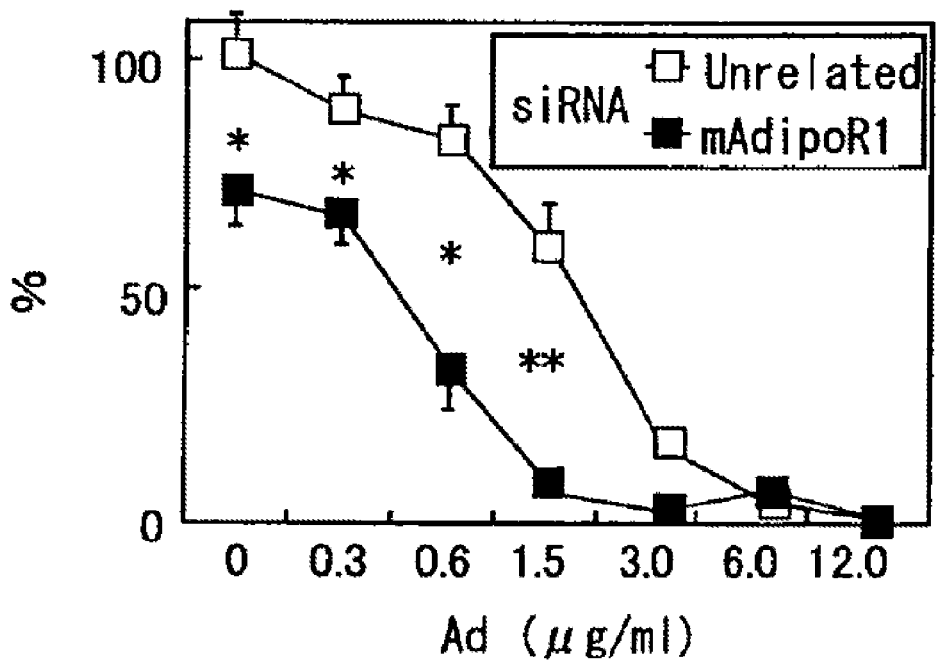
FIG. 5(d) shows the results of a competitive radioligand binding assay in which [$^{125}$I] full-length Adipo binding to cells transfected with siRNA duplex is displaced by increasing concentrations of unlabeled full-length Adipo.

Suppression of AdipoR1 expression by siRNA (see FIG. 5a) in C2C12 myocytes abolished globular Adipo binding activity and partially reduced full-length Adipo binding activity (see FIGS. 5c, 5d). FIG. 5c shows results (n=4) of a competitive radioligand binding assay in which [$^{125}$I] globular Adipo binding to cells transfected with siRNA duplex was replaced by increasing the concentration of unlabeled globular Adipo. FIG. 5d shows results (n=4) of a competitive radioligand binding assay in which [$^{125}$I] full-length Adipo binding to cells transfected with siRNA duplex was replaced by increasing the concentration of unlabeled full-length Adipo.

Figure 5F:
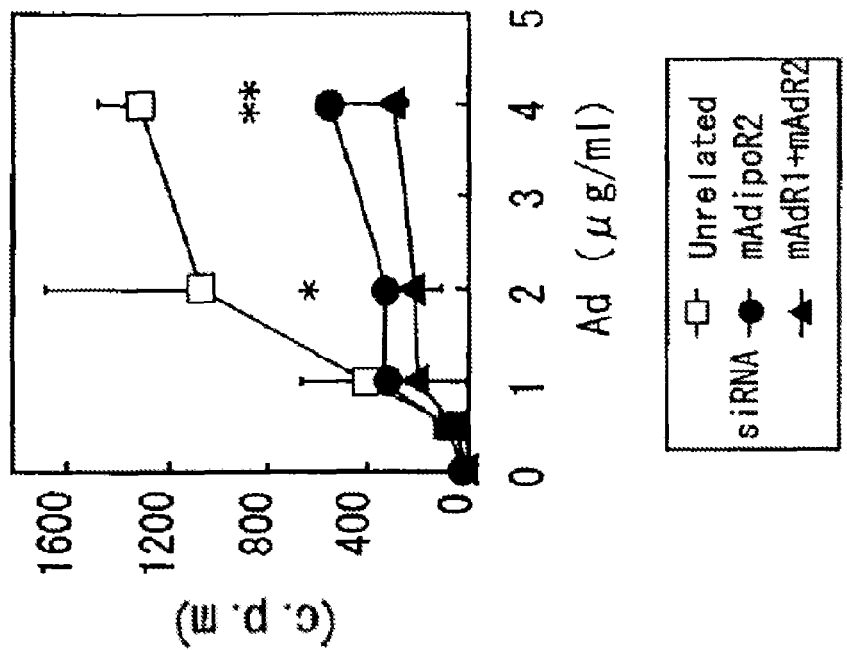
FIG. 5(f) shows the binding isotherm of full-length Adipo binding to C2C12 myocytes transfected with siRNA duplex.
Figure 5E:
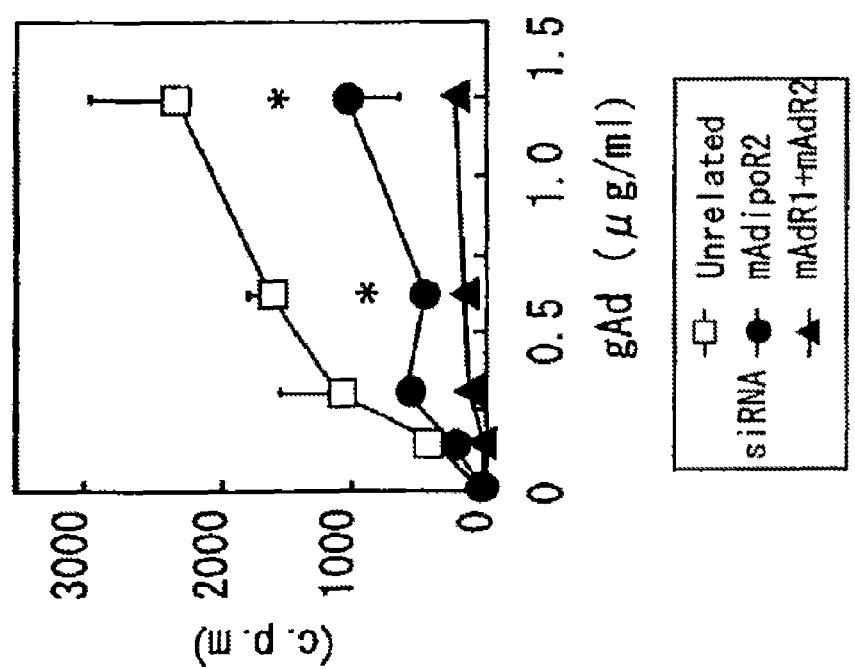
FIG. 5(e) shows the binding isotherm of [$^{125}$I] globular Adipo binding to C2C12 myocytes transfected with [$^{125}$I] siRNA duplex.
Figure 5G:
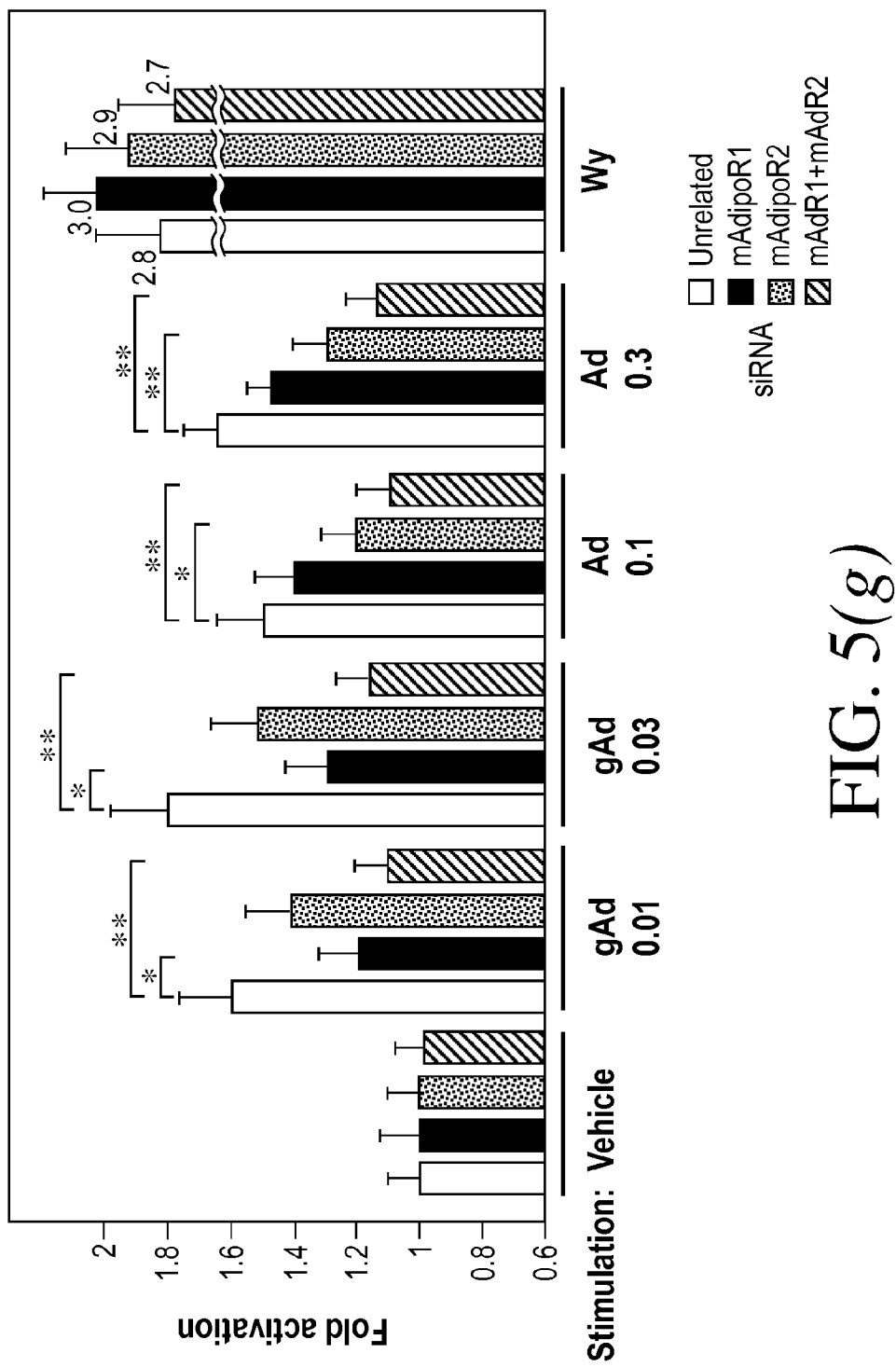
FIG. 5(g) shows PPARα ligand activity in C2C12 myocytes transfected with siRNA duplex which are incubated for 7 hours with globular Adipo, full-length Adipo or Wy-14,643.
Figure 5H:
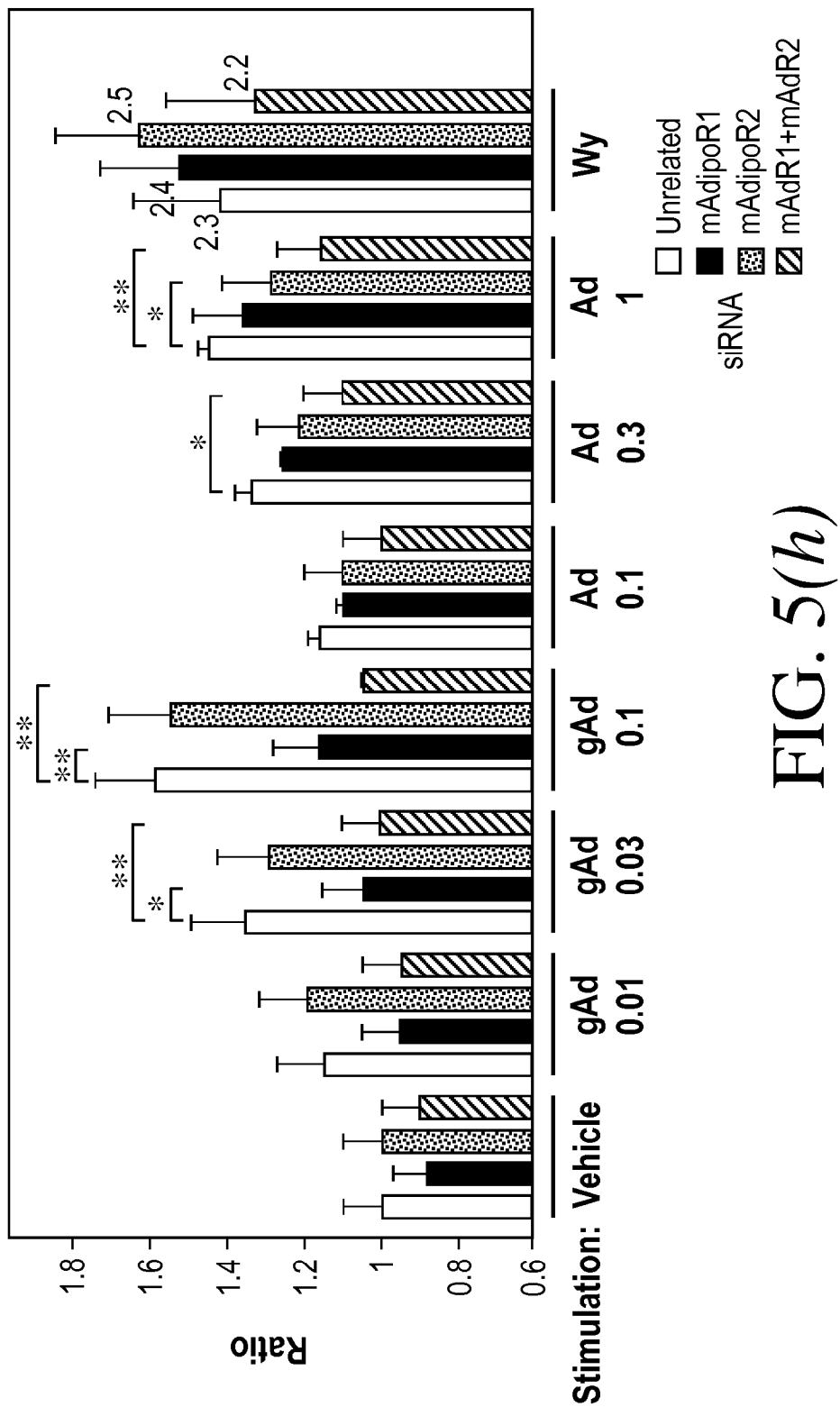
FIG. 5(h) shows in vitro fatty acid oxidation in C2C12 myocytes transfected with siRNA duplex which are incubated for 7 hours with globular Adipo, full-length Adipo or Wy-14,643.
Figure 5I:
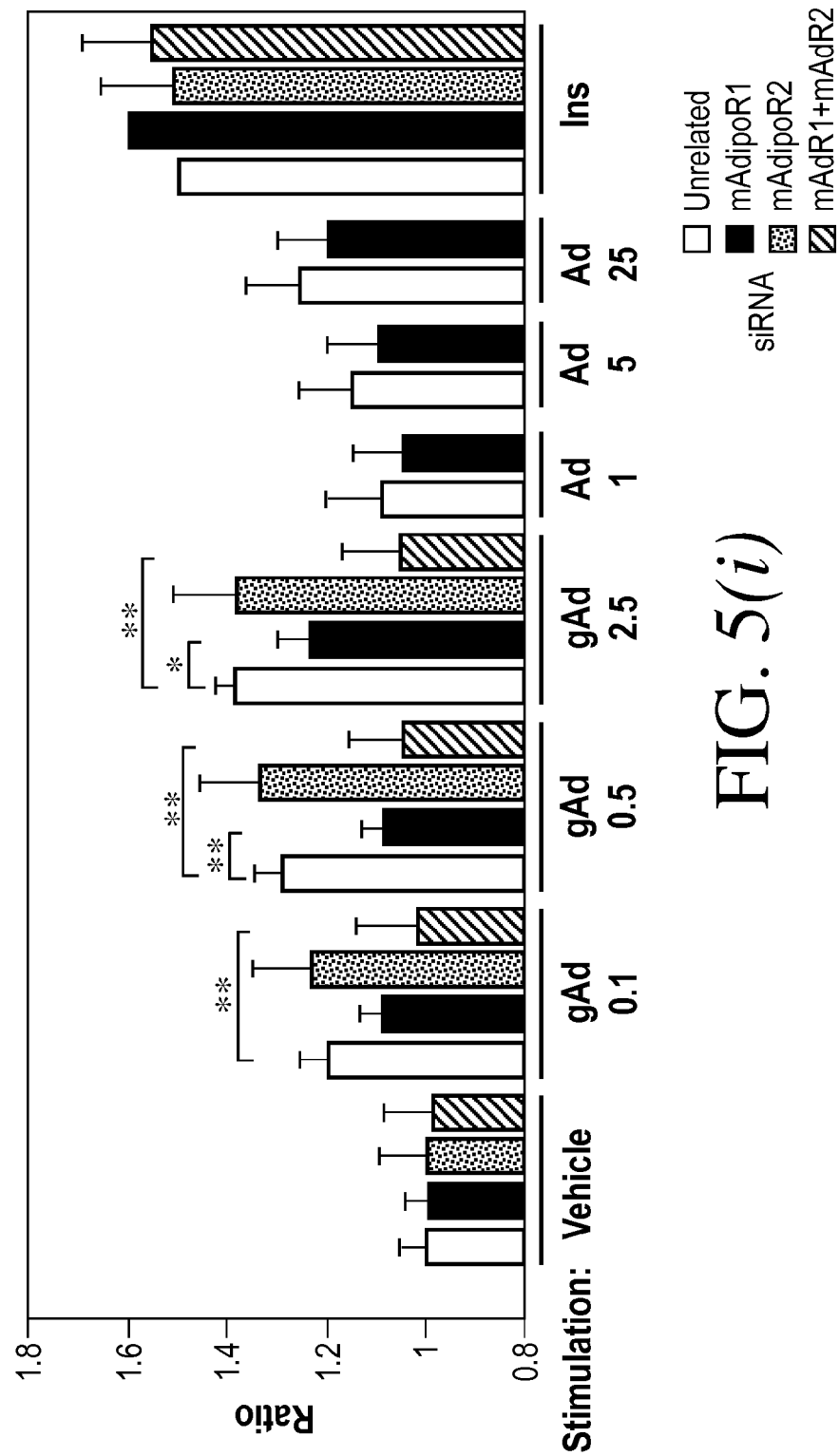
FIG. 5(i) shows glucose uptake in C2C12 myocytes transfected with siRNA duplex which are incubated for 7 hours with globular Adipo, full-length Adipo or insulin.

Treatment with either globular or full-length Adipo for 7 hours increased PPARα ligand activity (see FIG. 5g) and stimulated fatty-acid oxidation (see FIG. 5h) and glucose uptake (see FIG. 5i) in C2C12 myocytes. FIG. 5g shows PPARα ligand activity when C2C12 myocytes transfected with siRNA duplex were incubated for 7 hours with the indicated concentrations (μg/mL) of globular or full-length Adipo or with 10$^{-5}$ M Wy-14,643 ("Wy" in the figure). FIG. 5h shows in vitro fatty acid oxidation when C2C12 myocytes transfected with siRNA duplex were incubated for 7 hours with the indicated concentrations (μg/mL) of globular or full-length Adipo or with 10$^{-5}$ M Wy-14,643 ("Wy" in the figure). FIG. 5i shows glucose uptake when C2C12 myocytes transfected with siRNA duplex were incubated for 7 hours with the indicated concentrations (μg/mL) of globular or full-length Adipo or with 10$^{-7}$ M insulin ("Ins" in the figure). In FIGS. 5g-5i, "gAd0.01," "gAd0.03," "gAd0.1," "gAd0.5" and "gAd2.5" indicate 0.01, 0.03, 0.1, 0.5 and 2.5 μg/mL of globular Adipo, respectively, while "Ad0.1," "Ad0.3," "Ad1," "Ad5" and "Ad25" indicate 0.1, 0.3, 1, 5 and 25 μg/mL of full-length Adipo, respectively. In the figures, each bar shows mean±s.e. (n=3-5), with "*" indicating P<0.05 and "**" P<0.01. In FIGS. 5g-5i, white bars indicate results using unrelated siRNA, black bars using siRNA for mouse AdipoR1, dotted white bars using siRNA for mouse AdipoR2, and shaded bars using siRNA for mouse AdipoR1 and mouse AdipoR2.

Suppression of AdipoR1 expression by siRNA in C2C12 myocytes (see FIG. 5a) reduced increases in PPARα ligand activity (see FIG. 5g), fatty acid oxidation (see FIG. 5h) and glucose uptake (see FIG. 5i) by globular Adipo. In contrast, suppression of AdipoR1 expression failed to significantly reduce these effects by full-length Adipo. Thus, AdipoR1 appears to mediate increases in PPARα ligand activity, fatty acid oxidation and glucose uptake by globular Adipo in muscle cells.

To determine whether endogenous AdipoR2 mediates the specific binding and metabolic effects of Adipo in muscle cells, AdipoR2 expression was suppressed using siRNA (see FIG. 5b). Suppression of AdipoR2 expression by siRNA in C2C12 myocytes (see FIG. 5b) partially reduced both globular and full-length Adipo binding (see FIGS. 5e, 5f). Moreover, suppression of AdipoR2 expression partially reduced increases in PPARα ligand activity (see FIG. 5g) and fatty acid oxidation (see FIG. 5h) by full-length Adipo. Thus, AdipoR2 appears to partially mediate increases in PPARα ligand activity and fatty acid oxidation by full-length Adipo in muscle cells. FIG. 5e shows the binding isotherm of [$^{125}$I] globular Adipo binding to C2C12 myocytes transfected with siRNA duplex, and FIG. 5f shows the binding isotherm of [125I] full-length Adipo binding to C2C12 myocytes transfected with siRNA duplex. In the figures, white squares indicate results using unrelated control siRNA, black circles using siRNA for mouse AdipoR2, and black triangles using siRNA for mouse AdipoR1 and mouse AdipoR2.

It appears that AdipoR1 is a receptor with relative selectivity for globular Adipo, and AdipoR2 is a receptor with relative selectivity for full-length Adipo. However, suppressing the functional expression of either type of AdipoR has significant effects on both globular and full-length Adipo. These results may be explained by the observation that AdipoR1 and AdipoR2 may form both homo-and hetero-multimers (see FIG. 3e).

Interestingly, simultaneous suppression of AdipoR1 and AdipoR2 expression with siRNA in C2C12 myocytes almost abolished both globular Adipo and full-length Adipo binding (see FIGS. 5e, 5f), and increases in PPARα ligand activity (see FIG. 5g) and fatty acid oxidation (see FIG. 5h) by globular and full-length Adipo.

(7) Effects of siRNA on Binding and Action in Hepatocytes

Figure 6B:
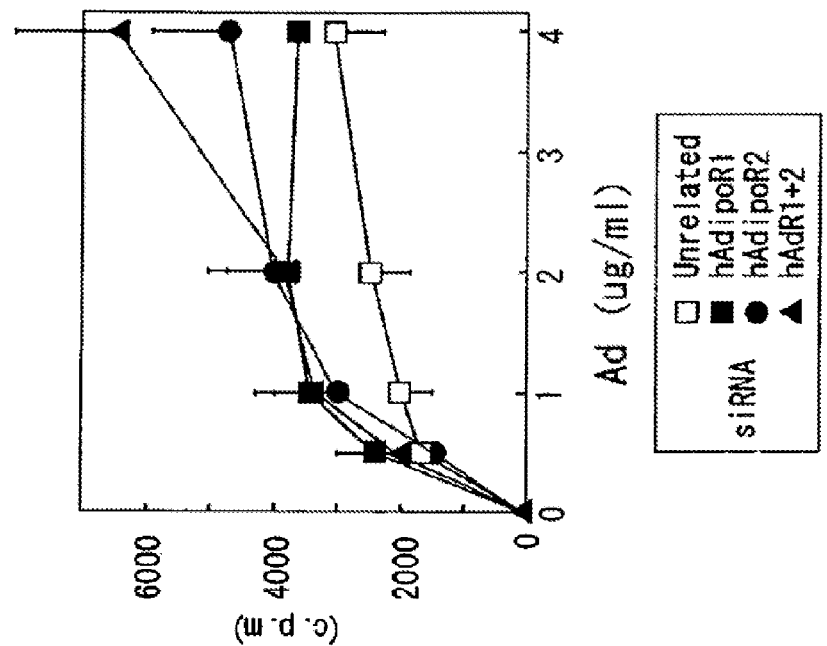
FIG. 6(b) shows specific binding of Ad to hepatocytes.
Figure 6A:
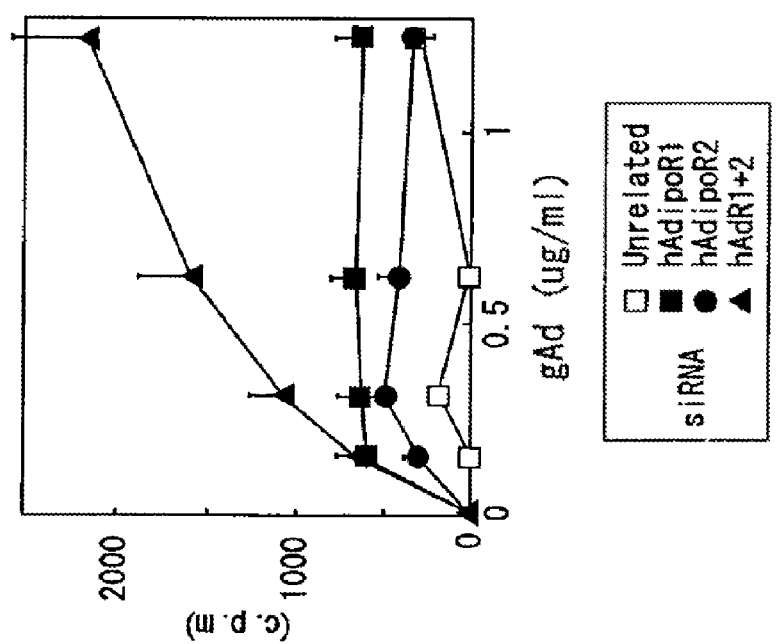
FIG. 6(a) shows specific binding of gAd to hepatocytes.
Figures 6C, 6D:
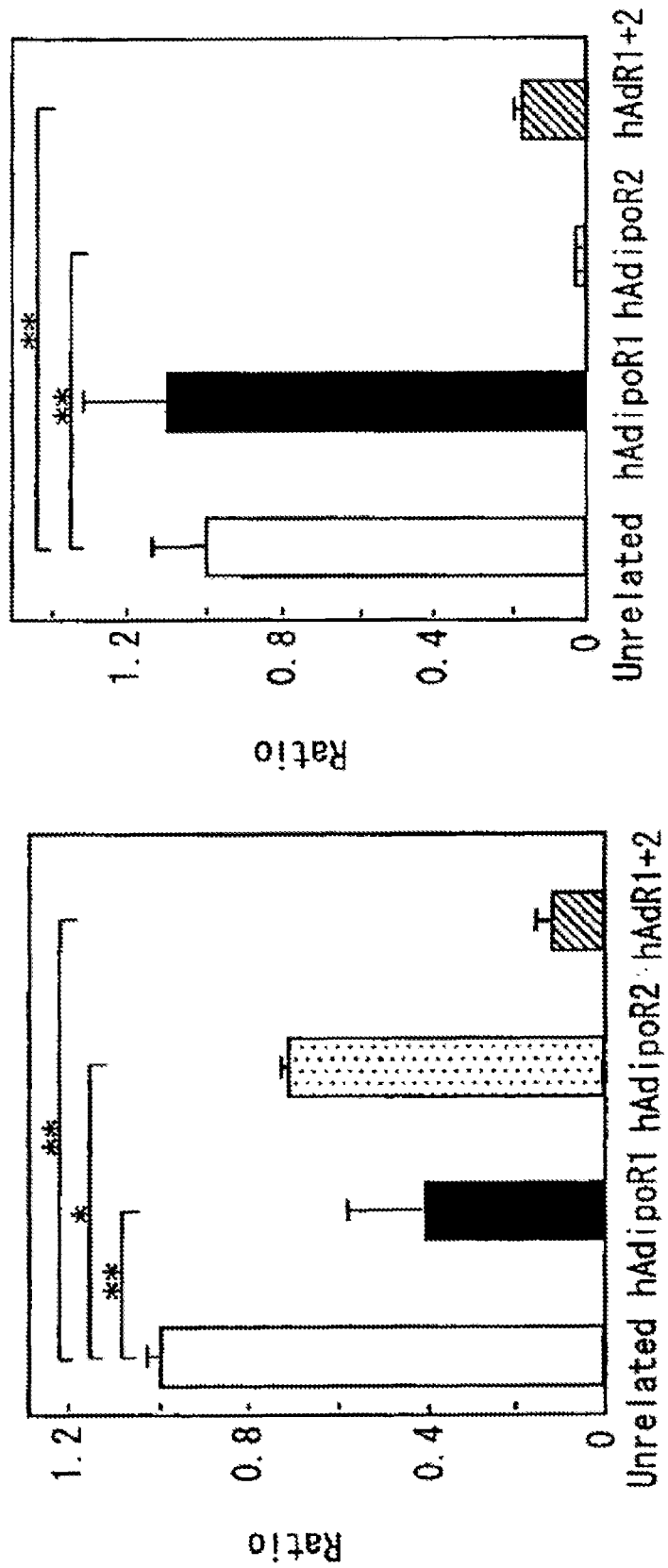
FIG. 6(c) shows expression levels of human AdipoR1 mRNA in HAEC.
FIG. 6(d) shows expression levels of human AdipoR2 mRNA in HAEC.

The binding of Adipo to hepatocytes was studied. Hepatocytes showed specific binding for full-length Adipo (see FIG. 6b). Expression of AdipoR1 and R2 enhanced binding of globular and full-length Adipo to hepatocytes (see FIGS. 6a, 6b). Conversely, suppression of AdipoR2 expression by siRNA in hepatocytes greatly reduced full-length Adipo binding (see FIG. 6b). These data appear to suggest that AdipoR1 is a receptor with relative selectivity for globular Adipo, while AdipoR2 is a receptor with relative selectivity for full-length Adipo.

Figure 6F:
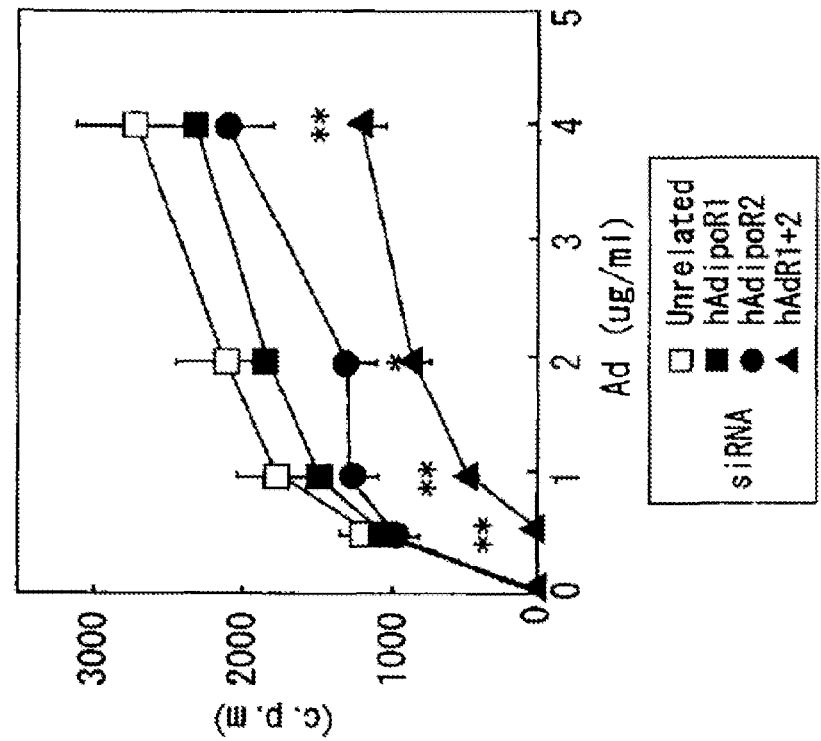
FIG. 6(f) shows specific binding of Ad to HAEC.
Figure 6E:
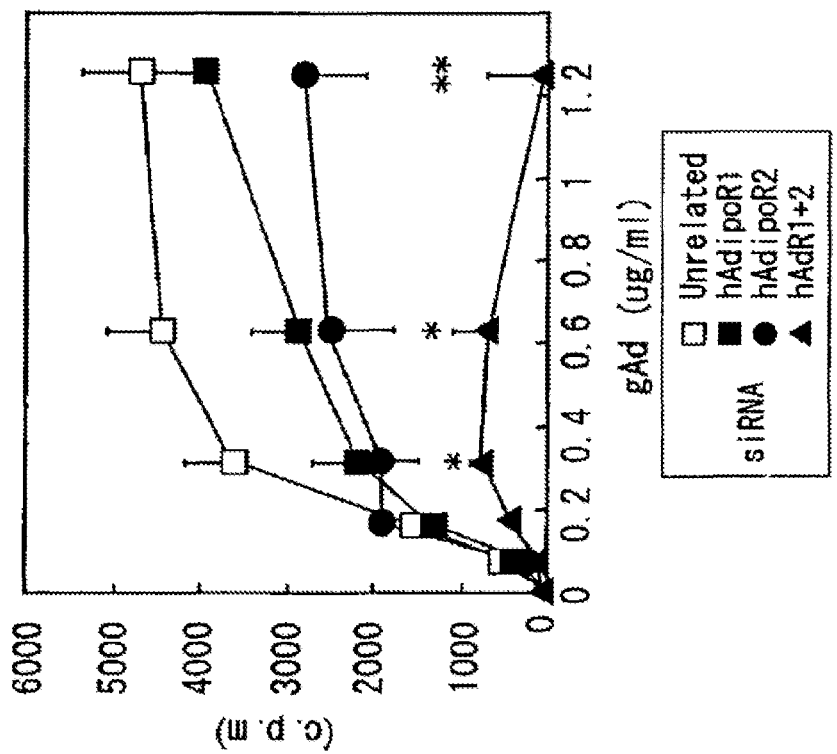
FIG. 6(e) shows specific binding of gAd to HAEC.

The binding of Adipo to Normal Human Aortic Endothelial Cells (HAEC) was studied. Simultaneous suppression of both AdipoR1 and AdipoR2 expression with siRNA greatly reduced globular Adipo binding (see FIG. 6e), and partially reduced full-length Adipo binding (see FIG. 6f). These data indicate that AdipoR1 and AdipoR2 are also receptors for Adipo in HAEC.

(8) Scatchard Plot Analysis

Figure 7A:
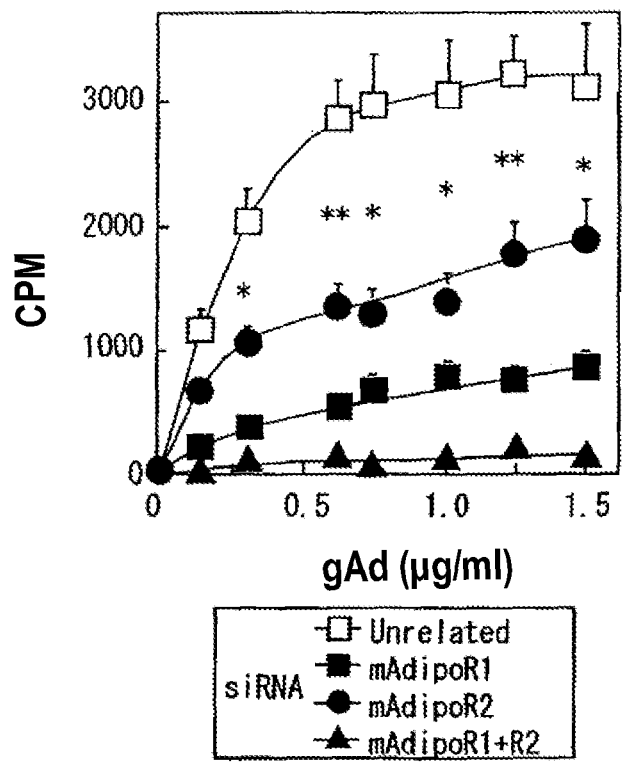
FIG. 7(a) shows the binding isotherm of [$^{125}$I] globular Adipo binding to C2C12 cells transfected with siRNA duplex.
Figure 7B:
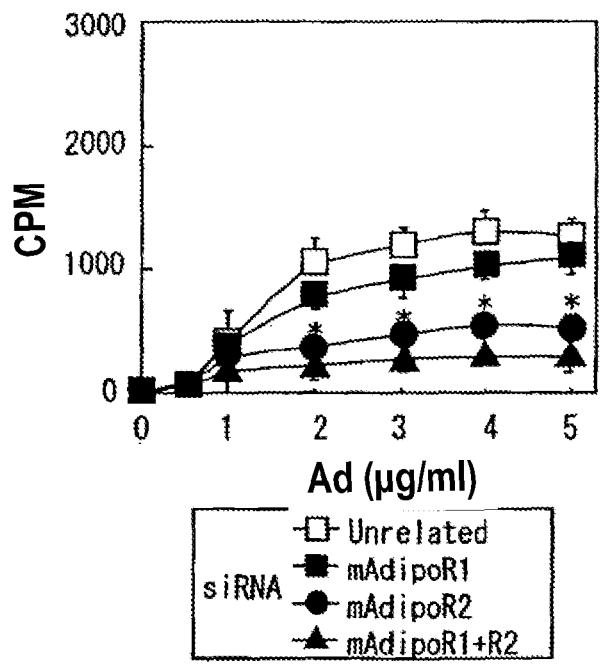
FIG. 7(b) shows the binding isotherm of [125I] full-length Adipo binding to C2C12 myocytes transfected with siRNA duplex.

FIGS. 7a and 7b show the results of the tests of FIGS. 5e and 5f conducted again in more detail. FIG. 7a (which corresponds to FIG. 5e) shows the binding isotherm of [125I] globular Adipo binding to C2C12 myocytes transfected with siRNA duplex, while FIG. 7b (which corresponds to FIG. 5f) shows the binding isotherm of [125I] full-length Adipo binding to C2C12 myocytes transfected with siRNA duplex. In FIGS. 7a and 7b, white squares indicate results using unrelated control siRNA, black squares using siRNA for mouse AdipoR1, black circles using siRNA for mouse AdipoR2, and black triangles using siRNA for mouse AdipoR1 and mouse AdipoR2.

Figure 7C:
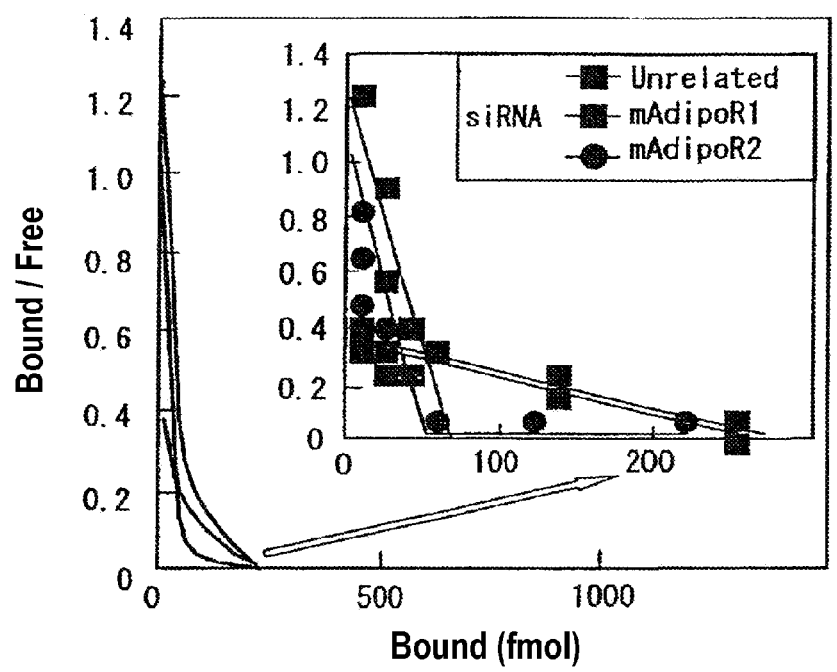
FIG. 7(c) shows the results of Scatchard plot analysis based on the results shown in FIG. 7(a)
Figure 7D:
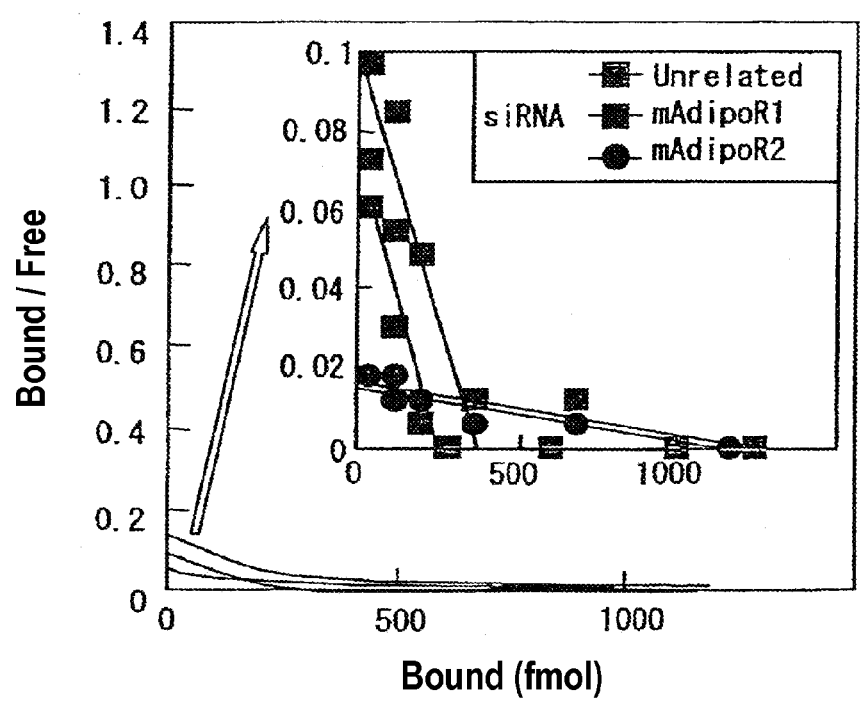
FIG. 7(d) shows the results of Scatchard plot analysis based on the results shown in FIG. 7(b)

Scatchard plot analysis was carried out based on the results shown in FIGS. 7a and 7b, with the results shown in FIGS. 7c and 7d.

C2C12 myocytes transfected with unrelated siRNA bound more strongly to globular Adipo than to full-length Adipo (see FIGS. 7a and 7b).

Scatchard plot analysis revealed that there are two types of binding sites for globular Adipo; high affinity binding sites (Kd value about 0.06 µg/mL, equivalent to 1.14 nM of gAd trimer) and intermediate affinity binding sites (Kd value about 0.80 µg/mL, equivalent to 14.4 nM of gAd trimer) (see FIG. 7c), and there are also two types of binding sites for full-length Adipo; intermediate affinity binding sites (Kd value about 6.7 µg/mL, equivalent to 49.1 nM of Ad hexamer) and low affinity binding sites (Kd value about 329.3 µg/mL, equivalent to 2415 nM of Ad hexamer) (see FIG. 7d).

Suppression of AdipoR1 expression with siRNA largely reduced globular Adipo binding (see FIG. 7a), but only barely reduced full-length Adipo binding (see FIG. 7b). Scatchard plot analysis revealed that specific suppression of AdipoR1 abrogated high affinity binding sites for globular Adipo, but failed to affect intermediate affinity binding sites for globular Adipo (see FIG. 7c). Moreover; Scatchard plot analysis revealed that specific suppression of AdipoR1 expression only partially reduced the activity of intermediate affinity binding sites for full-length Adipo, but abrogated low affinity binding sites for full-length Adipo (see FIG. 7d).

By contrast with AdipoR1, suppression of AdipoR2 expression with siRNA largely reduced full-length Adipo binding (see FIG. 7b), but barely reduced globular Adipo binding (see FIG. 7a). Scatchard plot analysis revealed that specific suppression of AdipoR2 only partly reduced the activity of high affinity binding sites for globular Adipo, but abrogated intermediate affinity binding sites for globular Adipo (see FIG. 7c). Moreover, Scatchard plot analysis revealed that specific suppression of AdipoR2 abrogated intermediate affinity binding sites for full-length Adipo, but failed to affect the activity of low affinity binding sites for full-length Adipo (see FIG. 7d).

Figure 8A:
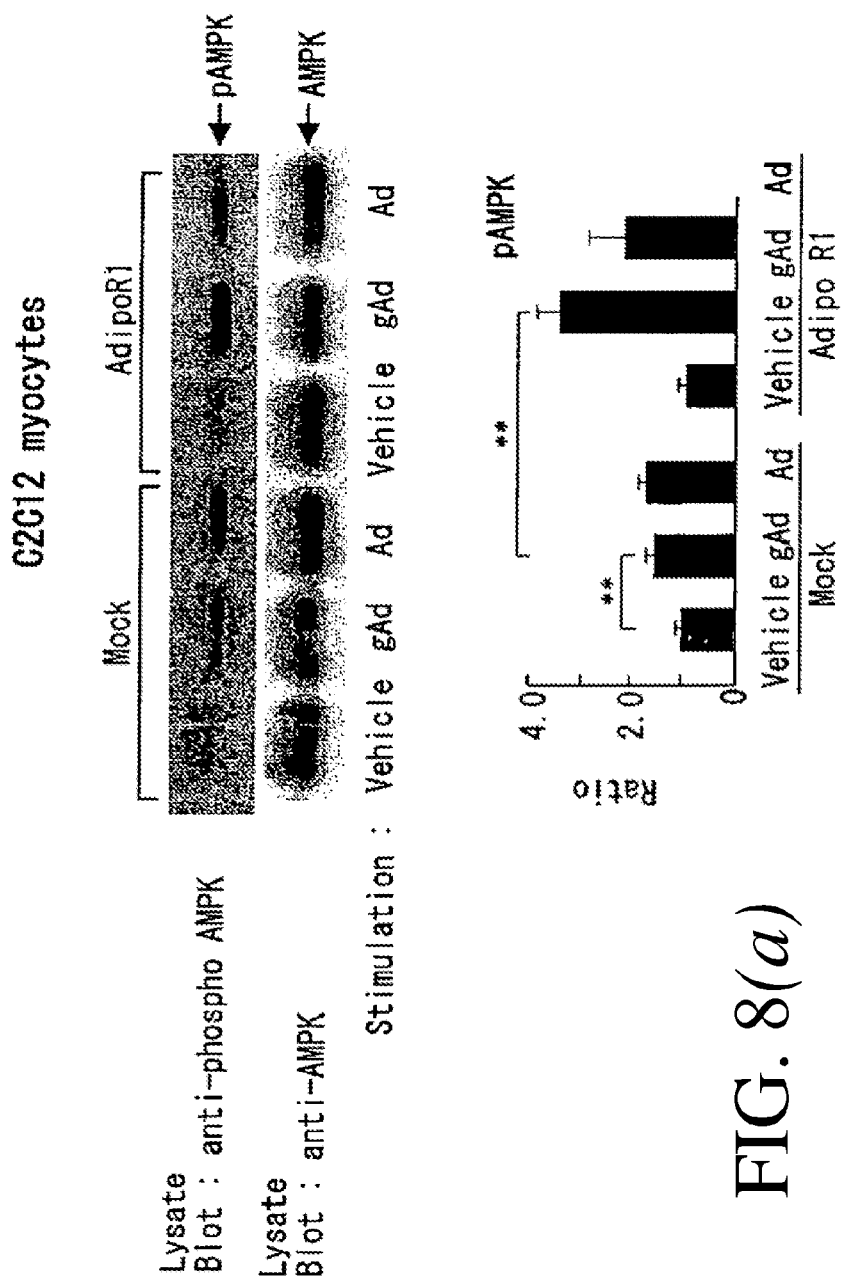
FIG. 8(a) shows the results when C2C12 cells transfected or not transfected with AdipoR1 are incubated for 10 minutes with 0.1 μg/mL or 1 μg/mL of gAd and a lysate of the cells was then reacted with anti-phosphorylated AMPK antibodies.
Figure 8B:
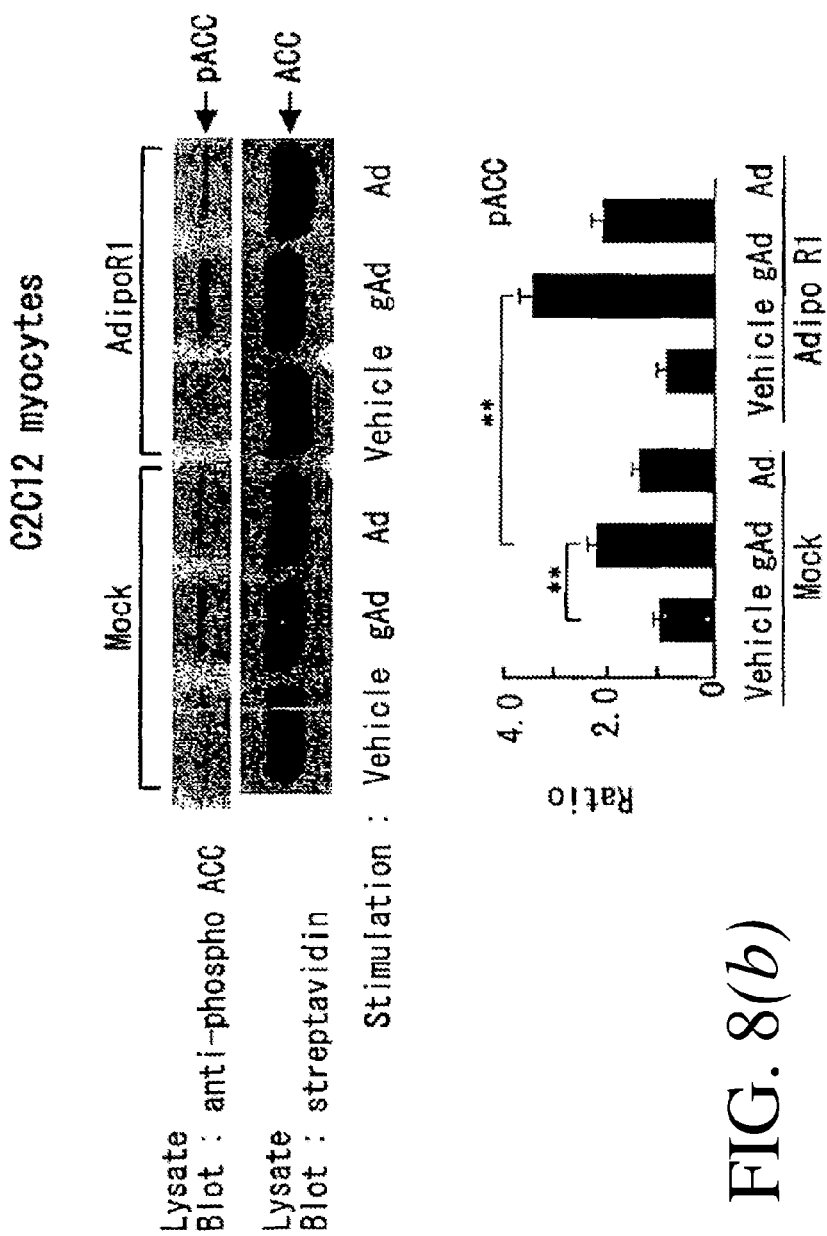
FIG. 8(b) shows the results when C2C12 cells transfected or not transfected with AdipoR1 are incubated for 10 minutes with 0.1 μg/mL or 1 μg/mL of gAd and a lysate of the cells is then reacted with anti-phosphorylated ACC antibodies.
Figure 8C:
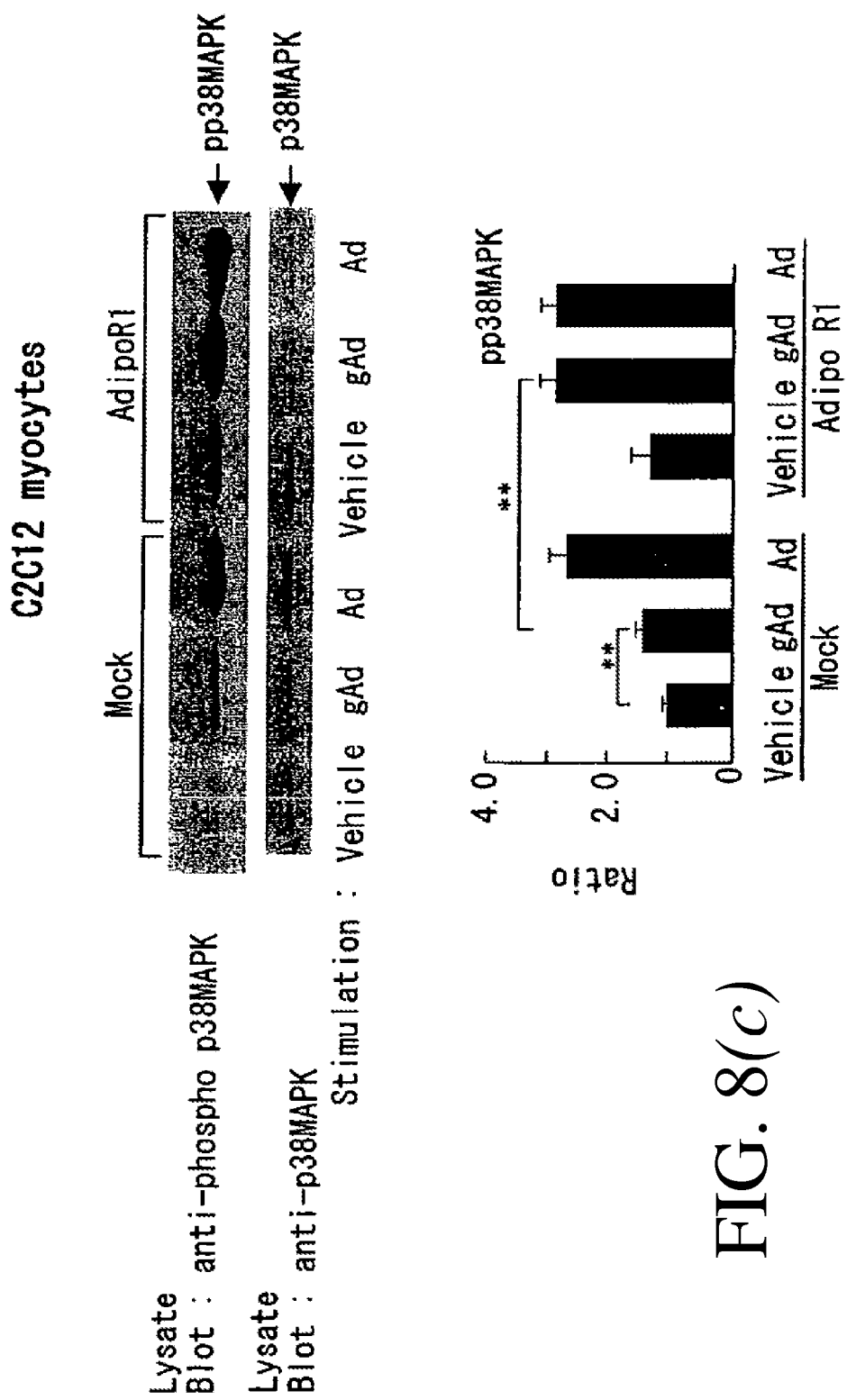
FIG. 8(c) shows the results when C2C12 cells transfected or not transfected with AdipoR1 are incubated for 10 minutes with 0.1 μg/ml, or 1 μg/ml, of gAd and a lysate of the cells is then reacted with anti-phosphorylated p38 MAPK antibodies.
Figure 8D:
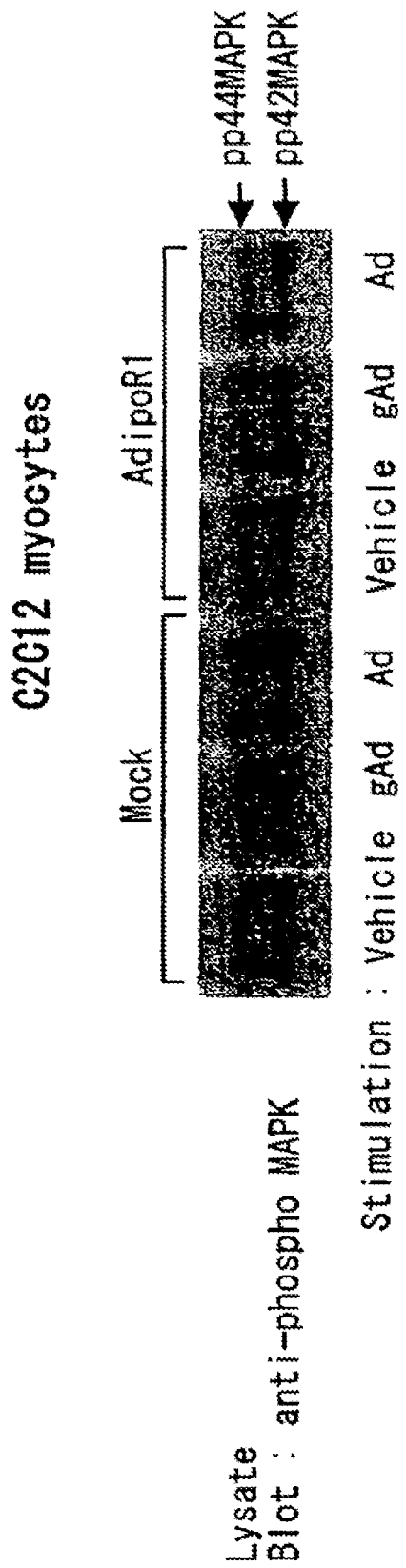
FIG. 8(d) shows the results when C2C12 cells transfected or not transfected with AdipoR1 are incubated for 10 minutes with 0.1 μg/mL or 1 μg/mL of gAd and a lysate of the cells is then reacted with anti-phosphorylated MAPK antibodies.
Figure 8E:
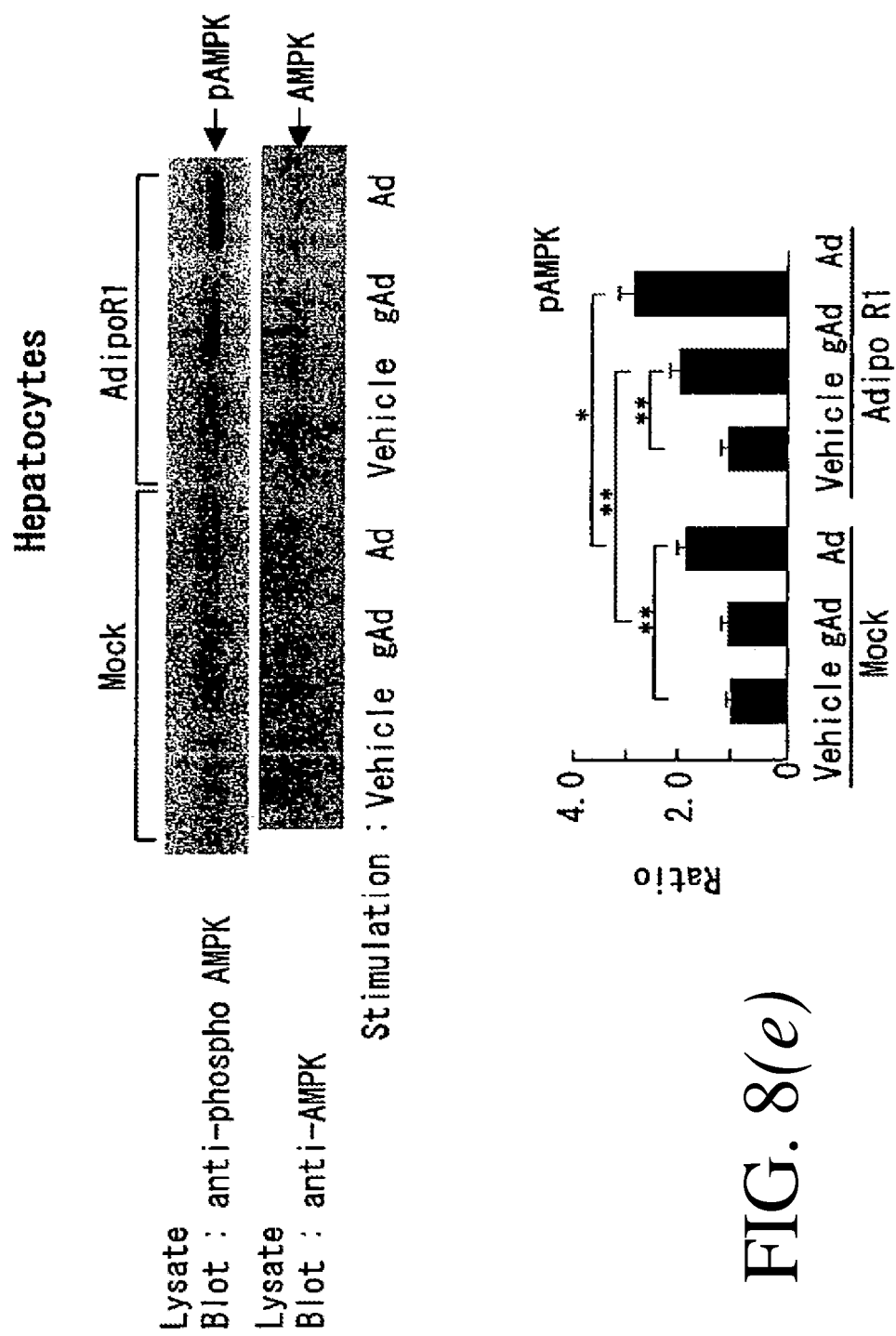
FIG. 8(e) shows the results when hepatocytes transfected or not transfected with AdipoR1 were incubated for 10 minutes with 0.1 μg/mL or 1 μg/mL of gAd and a lysate of the cells was then reacted with anti-phosphorylated AMPK antibodies.
Figure 8F:
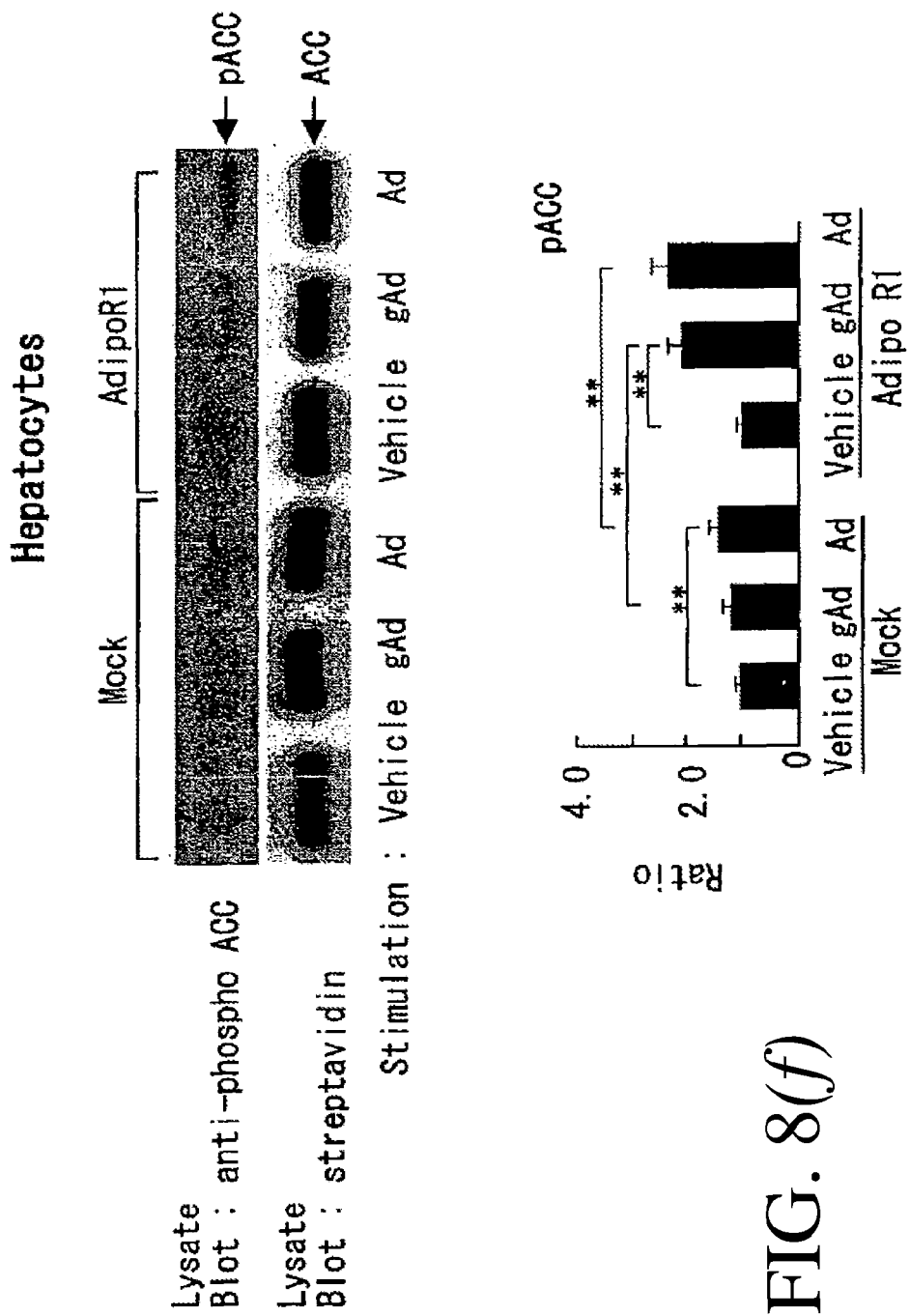
FIG. 8(f) shows the results when hepatocytes transfected or not transfected with AdipoR1 are incubated for 10 minutes with 0.1 μg/mL or 1 μg/mL of gAd and a lysate of the cells is then reacted with anti-phosphorylated ACC antibodies.

(9) Phosphorylation and Amount of Phosphorylation of AMPK, ACC, p38 MAPK and MAPK The panels in FIG. 8a show the results when C2C12 cells transfected ("AdipoR1" in figures) or not transfected ("Mock" in figures) with AdipoR1 were incubated for 10 minutes with 0.1 or 1 µg/mL of gAd, and a lysate of those cells was then reacted with anti-phosphorylated AMPK antibodies, while the panels in FIG. 8b show the results when a lysate of those cells was reacted with anti-phosphorylated ACC antibodies, the panels in FIG. 8c show the results when a lysate of those cells was reacted with anti-phosphorylated p38 MAPK antibodies, and the panels in FIG. 8d show the results when a lysate of those cells was reacted with anti-phosphorylated MAPK antibodies. The panels in FIG. 8e show the results when hepatocytes transfected ("AdipoR1" in figures) or not transfected ("Mock" in figures) with AdipoR1 were incubated for 10 minutes with 0.1 or 1 µg/mL of gAd and a lysate of those cells was then reacted with anti-phosphorylated AMPK antibodies, while the panels in FIG. 8f show the results when a lysate of those cells was reacted with anti-phosphorylated ACC antibodies. The graphs below the panels in FIGS. 8a-8f show amounts of phosphorylation at each position on the panel. In the figures, "pAMPK" is phosphorylated AMPK, "pACC" is phosphorylated ACC, "pp38 MAPK" is phosphorylated p38 MAPK, "pp44 MAPK is phosphorylated p44MAPK, and "pp42 MAPK" is phosphorylated p42 MAPK.

In C2C12 myocytes not transfected with AdipoR1, both globular Adipo and full-length Adipo increased amounts of phosphorylation of AMPK, ACC and p38 MAPK, but did not increase phosphorylation of MAPK and other protein kinases (see FIGS. 8a-8d). Expression of AdipoR1 in C2C12 cells was related to stimulation of phosphorylation of AMPK, ACC and p38 MAPK by globular Adipo (see FIGS. 8a-8d). This suggests that AdipoR1 mediates activation of AMPK and p38 MAPK by globular Adipo.

In hepatocytes not transfected with AdipoR1, full-length Adipo promoted AMPK activation and ACC phosphorylation, while globular Adipo did not (see FIGS. 8e and 8f). Expression of AdipoR1 in hepatocytes was related to stimulation of AMPK and ACC phosphorylation by globular and full-length Adipo (see FIGS. 8e and 8f). This suggests that AdipoR1 mediates AMPK and ACC phosphorylation by globular and full-length Adipo.

Figure 8G:
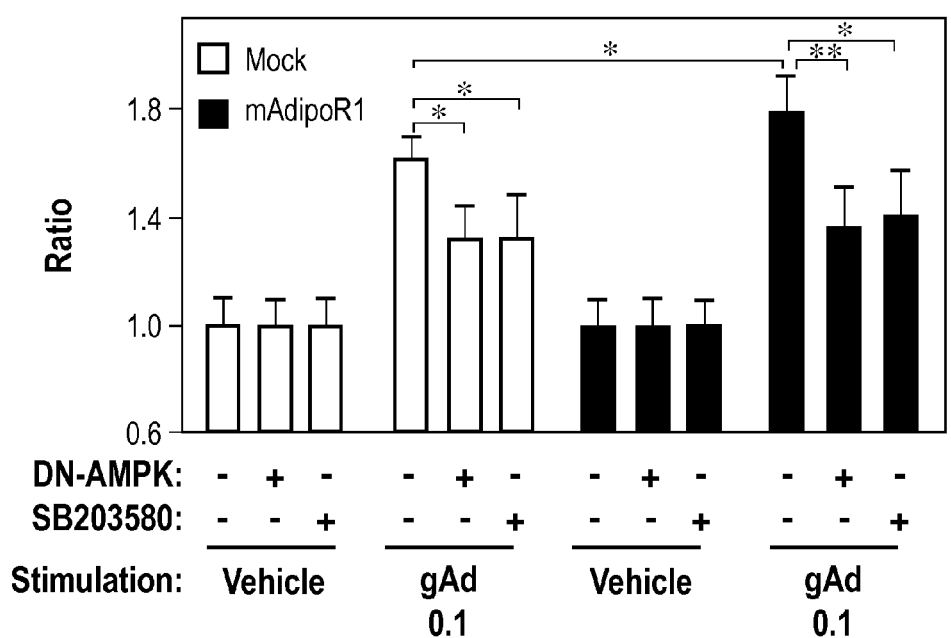
FIG. 8(g) shows fatty acid oxidation of C2C12 cells transfected or not transfected with AdipoR1 in the presence of dominant negative AMP kinase (DN-AMPK) or p38 MAPK-specific inhibitor SB203580.
Figure 8H:
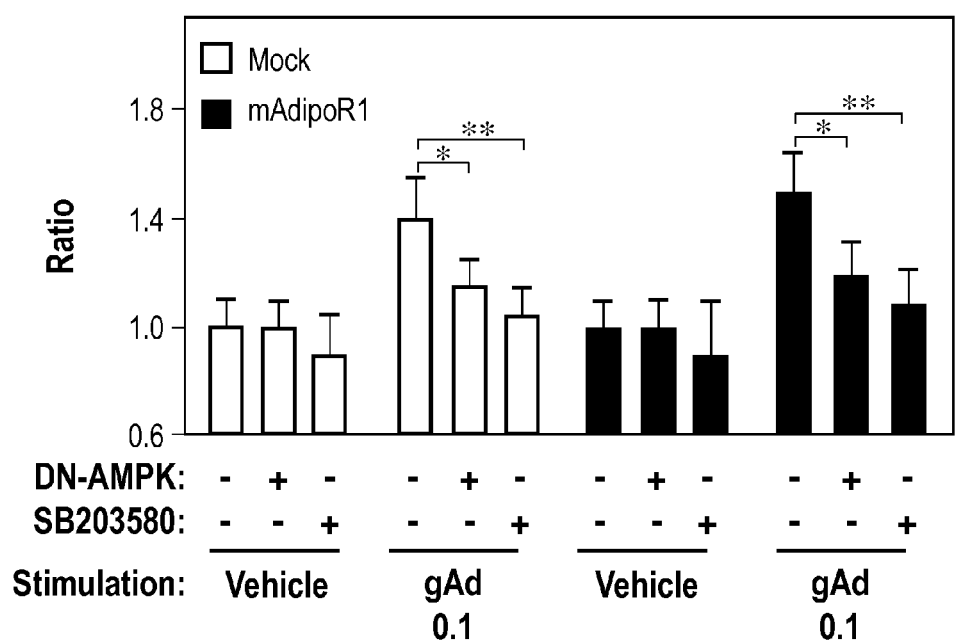
FIG. 8(h) shows glucose intake of C2C12 cells transfected or not transfected with AdipoR1 in the presence of dominant negative AMP kinase (DN-AMPK) or p38 MAPK-specific inhibitor SB203580.

In C2C12 myocytes not transfected with AdipoR1 ("Mock" in FIG. 8), the fatty acid oxidation and glucose uptake stimulated by globular Adipo were partially inhibited by dominant negative (DN) AMPK or the p38 MAPK specific inhibitor SB203580 (Barger, P. M. et al, *J. Biol. Chem.* 276, 44495-44501 (2001); Puigserver, P. et al, *Mol. Cell.* 8, 971-982 (2001); Michael, L. F. et al, *Proc. Natl. Acad. Sci. USA* 98, 3820-3825 (2001)) (see FIGS. 8g and 8h). Expression of AdipoR1 in C2C12 myocytes ("mAdipoR1" in FIG. 8) promoted fatty acid oxidation and glucose uptake by globular Adipo, but this effect was also partially inhibited by DN-AMPK or SB203580 (see FIGS. 8g and 8h). Thus, the stimulation of fatty acid oxidation and glucose uptake by globular Adipo via AdipoR1 appeared to be associated with both AMPK and p38 MAPK pathways in C2C12 myocytes.

From the results above, it appears that the AdipoR1 cDNA (Seq. Nos. 1 & 5) and AdipoR2 cDNA (Seq. Nos. 3 & 7) obtained in these examples encodes AdipoR1 (Seq. Nos. 2 & 6) and AdipoR2 (Seq. Nos. 4 & 8) having biological functions.

Industrial Applicability

The present invention provides a novel protein having adiponectin binding ability, a gene encoding the aforementioned protein, a recombinant vector containing the aforementioned gene, a transformant containing the aforementioned recombinant vector and antibody to the proteins. Moreover, the present invention provides a screening method and screening kit for screening a ligand, agonist and antagonist to an adiponectin receptor using the aforementioned protein, gene, recombinant vector or transformant.

The invention claimed is:

1. An isolated antibody or antigen-binding fragment thereof, which specifically binds to a protein as set forth in (a) or (b) below:
   (a) a protein comprising the amino acid sequence according to SEQ ID NO: 4 or 8; or
   (b) a protein comprising the amino acid sequence according to SEQ ID NO: 4 or 8 with one or more amino acids deleted, replaced or added, and having adiponectin binding ability.

2. The antibody or fragment of claim 1, wherein the antibody is a polyclonal antibody, a monoclonal antibody, a human antibody, a humanized antibody, a single chain antibody, Fab, Fab', F(ab')$_2$, Fv or scFv.

3. An isolated cell expressing the antibody or fragment of claim 1.

4. A pharmaceutical composition comprising the antibody or fragment of claim 1 or 2, and a pharmaceutically acceptable diluent or carrier.

5. An isolated antibody or antigen-binding fragment thereof, which specifically binds to a protein as set forth in (a) or (b) below:
   (a) a protein comprising the amino acid sequence according to SEQ ID NO: 4; or
   (b) a protein comprising the amino acid sequence according to SEQ ID NO: 4 with one or more amino acids deleted, replaced or added, and having adiponectin binding ability.

6. The antibody or fragment of claim 5, wherein the antibody is a polyclonal antibody, a monoclonal antibody, a human antibody, a humanized antibody, a single chain antibody, Fab, Fab', F(ab')$_2$, Fv or scFv.

7. An isolated cell expressing the antibody or fragment of claim 5.

8. A pharmaceutical composition comprising the antibody or fragment of claim 5, and a pharmaceutically acceptable diluent or carrier.

9. An isolated antibody or antigen-binding fragment thereof, which specifically binds to a protein as set forth in (a) or (b) below:
   (a) a protein comprising the amino acid sequence according to SEQ ID NO: 8; or
   (b) a protein comprising the amino acid sequence according to SEQ ID NO: 8 with one or more amino acids deleted, replaced or added, and having adiponectin binding ability.

10. The antibody or fragment of claim 9, wherein the antibody is a polyclonal antibody, a monoclonal antibody, a human antibody, a humanized antibody, a single chain antibody, Fab, Fab', F(ab')$_2$, Fv or scFv.

11. An isolated cell expressing the antibody or fragment of claim 9.

12. A pharmaceutical composition comprising the antibody or fragment of claim 9, and a pharmaceutically acceptable diluent or carrier.

* * * * *